(12) United States Patent
Khrimian et al.

(10) Patent No.: US 9,451,771 B2
(45) Date of Patent: Sep. 27, 2016

(54) COMPOSITIONS AND METHODS TO ATTRACT THE BROWN MARMORATED STINK BUG (BMSB), *HALYOMORPHA HALYS*

(71) Applicant: United States of America as Represented by the Secretary of Agriculture, Washington, DC (US)

(72) Inventors: Ashot Khrimian, Rockville, MD (US); Jeffrey R. Aldrich, Hyattsville, MD (US); Aijun Zhang, Laurel, MD (US); Tracy C. Leskey, Shepherdstown, WV (US); Donald C. Weber, Arlington, VA (US)

(73) Assignee: The United States of America, as Represented By the Secretary of Agriculture, Washington, DC (US)

( * ) Notice: Subject to any disclaimer, the term of this patent is extended or adjusted under 35 U.S.C. 154(b) by 774 days.

(21) Appl. No.: 13/712,284

(22) Filed: Dec. 12, 2012

(65) Prior Publication Data
US 2014/0161764 A1 Jun. 12, 2014

(51) Int. Cl.
*A01N 43/20* (2006.01)
*A01N 49/00* (2006.01)
*C07D 303/14* (2006.01)

(52) U.S. Cl.
CPC ............ *A01N 43/20* (2013.01); *A01N 49/00* (2013.01); *C07D 303/14* (2013.01)

(58) Field of Classification Search
CPC .................................................... A01N 43/20
See application file for complete search history.

(56) References Cited

U.S. PATENT DOCUMENTS 7,151,225 B2 12/2006 Fujikami
7,824,668 B2 11/2010 McKibben
8,663,619 B2 3/2014 Zhang et al.

(Continued)

OTHER PUBLICATIONS

Gill, The brown marmorated stink bug, Growenalks, Pest Management, 2010, http://ballpublishing.com/GrowerTalks/ViewArticle.aspx?articleid=18206.

(Continued)

*Primary Examiner* — Benjamin Packard
(74) *Attorney, Agent, or Firm* — John Fado; G. Byron Stover

(57) ABSTRACT

A composition (useful for attracting *Halyomorpha halys*) containing (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and optionally a carrier material or carrier. The composition may also contain (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol where the composition contains a 3:1 ratio of cis-epoxybisabolenols:trans-epoxybisabolenols produced from (R)-citronellal. These compositions were based on the newly discovered aggregation pheromone components: (3S,6S,7R,10S)-10,11-epoxy-1-bisabolen-3-ol and (3R,6S,7R,10S)-10,11-epoxy-1-bisabolen-3-ol. The composition may also contain methyl(2E,4E,6Z)-decatrieonate. Also a method for attracting *Halyomorpha halys* to an object or area, involving treating said object or area with a *Halyomorpha halys* attracting composition containing a *Halyomorpha halys* attracting effective amount of the composition.

12 Claims, 23 Drawing Sheets
(4 of 23 Drawing Sheet(s) Filed in Color)

(56) References Cited

U.S. PATENT DOCUMENTS

| | | |
|---|---|---|
| 8,663,620 B2 | 3/2014 | Zhang et al. |
| 2008/0044375 A1 | 2/2008 | McKibben |
| 2008/0263938 A1 | 10/2008 | Schneidmiller |
| 2011/0067293 A1 | 3/2011 | Schneidmiller et al. |
| 2012/0294828 A1 | 11/2012 | Zhang |
| 2013/0078211 A1 | 3/2013 | Zhang et al. |

OTHER PUBLICATIONS

Zahn, Q-H et al., "Murgantiol as a Stink Bug Synergistic Attractant for use Outdoors," U.S. Appl. No. 13/410,124, filed Mar. 1, 2014.

Zhang, Q.-H. et al., Essential Oils as Spatial Repellents for the Brown Marmorated stink Bug, *Halyomorpha halys* (Stal) (Hemiptera: Pentatomidae), Journal of Applied Entomology, 2013,10 pages Aldrich, J.R. et al., Identification and Attractiveness of a Major Pheromone Component for Nearctic *Euschistus* spp. Stink Bugs (Heteroptera: Pentatomidae), Environ. Entomol., 1991, vol. 20 (2), pp. 477-483.

Aldrich, J.R. et al., Methyl 2,4,6-decatrienoates Attract Stink Bugs and Tachinid Parasitoids, J. Chem. Ecol., 2007, vol. 33, pp. 801-815.

Aldrich, J.R. et al., Semiochemically Based Monitoring of the Invasion of the Brown Marmorated Stink Bug and Unexpected Attraction of the Native Green Stink Bug (Heteroptera: Pentatomidae) in Maryland, Florida Entomologist, 2009, vol. 92 (3), pp. 483-491.

Aldrich, J.R. et al., Pheromone Strains of the Cosmopolitan Pest, Nezara viridula (Heteroptera: Pentatomidae), Journal of Experimental Zoology, 1987, vol. 244, pp. 171-175.

Bae, S.D. et al., Attractiveness of Conspecific Stink Bugs to Adult Stink Bug-Baited Traps in Soybean Fields, Journal of Asia-Pacific Entomology, 2012, vol. 15, pp. 148-151.

Baker, R. et al., Identificaiton and Synthesis of (Z)-(1'S,3'R,4'S)(-)-2-(3',4'-Epoxy-4'-methylcyclohexyl)-6-methylhepta-2,5-diene, the Sex Pheromone of the Southern Green Stinkbyg, *Nezara viridula* (L.), J. Chem. Soc., Chem. Commun., 1987, pp. 414-416.

Bhonsle, J.B. et al., Zynthesis of (+)-zingiberene, Indian Journal of Chemistry, vol. 33B, 1994, pp. 313-316.

Blair, M. et al., A New Diastereoselective Entry to the (1S,4R)-and (1S,4S)- isomers of 4-isopropyl-1-methyl-2-cyclohexen-1-ol. Aggregatio Pheromones of the Ambrosia Beetle *Platypus quercivorus*, Tetrahedron:Asymmetry, 2009, vol. 20, pp. 2149-2153.

Borges, M. et al., Sex Attractant Pheromone from the Rice Stalk Stink Bug, *Tibraca limbativentris* Stal, J. Chem. Ecol., 2006, vol. 32, pp. 2749-2761.

Flack, H.D., On Enantiomorph-Polarity Estimation, Acta Cryst., 1983, vol. A39, pp. 876-881.

Frater, G. et al., Synthesis of (+)-(4S,8R)-8-Epi- and (−)-(rR,8S)-4-Epi-B-bisabolol, Helvetica Chimica Acta, 1989, vol. 72, pp. 653-658.

Gill, S. et al., Brown Marmorated Stink Bug (*Halyomorpha halys*),IPM Pest Alert, 2010, www.ipmnet.umd.edu.

Gill, S. et al., Brown Marmorated Stink Bug (*Halyomorpha halys*),IPM Garden Center Fact Sheet, 2011, www.ipmnet.umd.edu.

Hooft R.W.W. et al., Determination of Absolute structure Using Bayesian Statistics on Bijvoet Differences, Journal of Applied Crystallography, 2008, vol. 41, pp. 96-103.

Khrimian, A., The Geometric Isomers of Methyl-2,4,6-decatrienoate, Including Pheromones of a Least Two Species of Stink Bugs, Tetrahedron, 2005, vol. 61, pp. 3651-3657.

Khrimian, A. et al., Pheromone of the Banana-Spotting Bug, *Amblypelta lutescens lutescens* Distant (Heteroptera: Coreidae): Identificaiton, Synthesis, and Field Bioassay, Psyche, 2012, vol. 2012, pp. 1-8.

Kreiser, W. et al., Stereospecific Synthesis of (+)-B-Sesquiphellandrene, Helvetica Chimica Acta, 1999, vol. 82, pp. 1427-1433.

Leal, W.S. et al., Male-Released Sex Pheromone of the Stink Bug *Piezodorus hybneri*, Journal of Chemical Ecology, 1998, vol. 24 (11), pp. 1817-1829.

Leskey, T.C. et al., Pest Status of the Brown Marmorated Stink Bug, *Halyomorpha halys* in the USA, Outlooks on Pest Management, 2012, 218-226.

Leskey, T.C. et al., Impact of the Invasive Brown Marmorated Stink Bug, *Halyomorpha halys* (Stal), in Mid-Atlantic Tree Fruit Orchards in the United States: Case Studies of Commercial Management, Psche, 2012, pp. 1-14.

McBrien, H.L. et al., Male-Produced Sex Attractant Pheromone of the Green Stink Bug, *Acrosternum hilare* (Say), Journal of Chemical Ecology, 2001, vol. 27 (9), pp. 1821-1839.

McBrien, H.L. et al., Sex Attractant Pheromone of the Red-Shouldered Stink Bug *Thyanta pallidovirens*: A Pheromone Blend with Multiple Redundant Components, Journal of Chemical Ecology, 2002, vol. 28 (9), pp. 1797-1818.

Millar, J.G. et al., Pentatomid Bug Pheromones in IPM: Possible Applications and Limitations, Use of Pheromones and Other Semiochemicals in Integrated Production, IOBC wprs Bulletin, 2002, vol. 25, pp. 1-11.

Millar, J.G., Methyl (2E.4Z,6Z)-Deca-2,4,6-trienoate, a Thermally Unstable, Sex-Specific Compound from the Stink Bug *Thyanta pallidovirens*, Tetrahedron Letters, 1997, vol. 38 (46), pp. 7971-7972.

Millar, J.G., Rapid and Simple Isolation of Zingiberene from Ginger Essential Oil, J. Nat. Prod., 1998, vol. 61, pp. 1025-1026.

Mitzner, B.M. et al., Infrared Spectra of Monoterpenes and Related Compounds. II. Terpene Alcohols, Applied Spectroscopy, 1968, vol. 22 (1), pp. 34-53.

Moore, C.J. et al., An Asymmetric Dihydroxylation Route to (3R,5E)-2,6-Dimethyl-2,3-epoxyocta-5,7-diene: The Major Volatile Component from Male Fruit-Spotting Bugs, J. Org. Chem., 1999, vol. 64, pp. 9742-9744.

Moraes, M.C.B. et al., Sex Attractant Pheromone from the Neotropical Red-Shouldered Stink Bug, *Thyanta perditor* (F.), Journal of Chemical Ecology, 2005, vol. 31 (6), pp. 1415-1427.

Mori, K., Synthesis of (1S,4R)-4-isopropyl-1-methyl-2cyclohexen-1-ol, the Aggregation Pheromone of the Ambrosia Beetle *Platypus quercivorus*, its Racemate, (1R,4R)- and (1S,4S)-isomers, Tetrahedron: Asymmetry, 2006, vol. 17, pp. 2133-2142.

Sharpless, K.B. et al., The Omium-Catalyzed Asymmetric Dihydroxylation: A New Ligand Class and a Process Improvement, J. Org. Chem., 1992, vol. 57, pp. 2768-2771.

Sheldrick, G.M., A Short History of SHELX, Acta Cryst., 2008, vol. A64, pp. 112-122.

Siewert, J. et al., Rhodium-Catalyzed Enantioselective 1,2-Addition of Aluminum Organyl Compounds to Cyclic Enones, Angew. Chem. Int. Ed., 2007, vol. 46, pp. 7122-7124.

Soffer, M.D. et al., The Total Stereostructure of(−)-Isozingiberene Dihydrochloride, Tetrahedron Letters, 1985, vol. 26 (30), pp. 2543-2546.

Sugie, H. et al., Identification of the Aggregation Pheromone of the Brown-Winged Green Bug, *Plautia stali* Scott (Heteroptera: Pentatomidae), Appl. Entomol. Zool., 1996, vol. 31 (3), pp. 427-431.

Terhune, S.J. et al., Four New Sesquiterpene Analogs of Common Monoterpenes, Can. J. Chem., 1975, vol. 53, pp. 3285-3293.

Tillman, P.G. et al., Pheromone Attracation and Cross-Attraction of *Nezara*, *Acrosternum*, and *Euschistus* spp. Stink Bugs (Heteroptera: Pentatomidae) in the Field, Environ. Entomol. 2010, vol. 39 (2), pp. 610-617.

Yadav, J.S. et al., A Concise Stereoselective Total Synthesis of (+)-Artemisinin, Tetrahedron, 2010, vol. 66, pp. 2005-2009.

Zahn, D.K. et al. Identificaiton, Synthesis, and Bioassay of a Male-Specific Aggregation Pheromone form the Harlequin Bug, *Murgantia histrionica*, J. Chem. Ecol., 2008, vol. 34, pp. 238-251.

Zahn, D.K. et al., Erratum to Identificaiton, Synthesis, and Bioassay of a Male-Specific Aggregation Pheromone from the Harlequin Bug, *Murgantia histrionica*, J. Chem. Ecol., 2012, vol. 38, p. 126.

Zhang, A. et al., Stimulatory Beetle Volatiles for the Asian Longhorned Beetle, *Anoplophora glabripennis* (Motschulsky), Z. Naturforsch, 2002, vol. 57C, pp. 553-558.

*cis*-Epoxybisabolenols (3*S*,6*S*,7*R*,10*S*)-10,11-epoxy-1-bisabolene-3-ol, 1

(3*R*,6*R*,7*R*,10*R*)-10,11-epoxy-1-bisabolen-3-ol, 2

*trans*-Epoxybisabolenol (3*R*,6*S*,7*R*,10*S*)-10,11-epoxy-1-bisabolene-3-ol, 3

10,11-epoxy-1,3(15)-bisaboladiene, 4

10,11-epoxy-1,3-bisaboladiene, 5

10,11-epoxy-1,3,5-bisabolatriene, 6

ORTEP drawing of triol 28

Part A
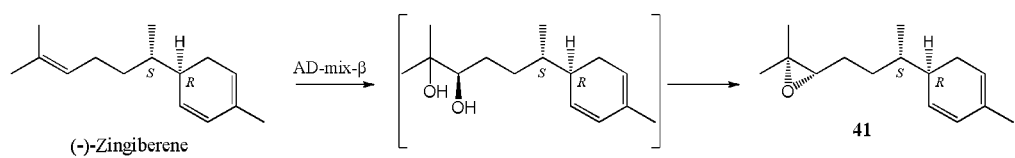
Part B
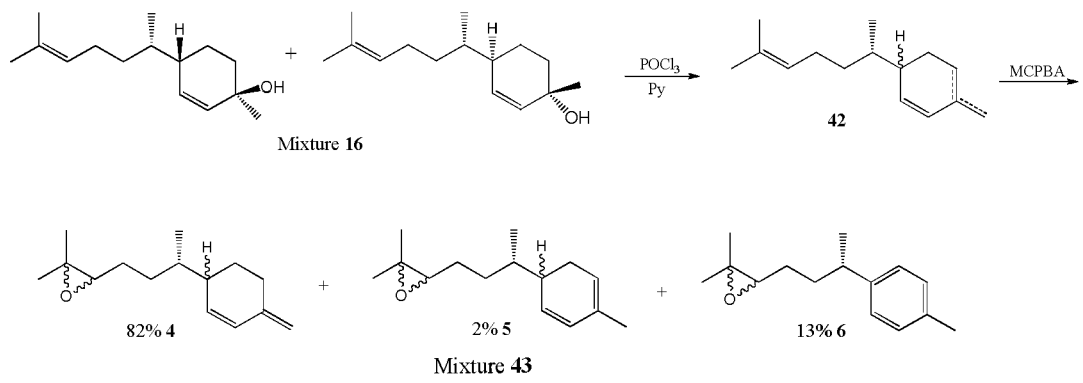
Figure 20
Fig. 20

COMPOSITIONS AND METHODS TO ATTRACT THE BROWN MARMORATED STINK BUG (BMSB), *HALYOMORPHA HALYS*

REFERENCE TO RELATED APPLICATION

This application claims the benefit of U.S. Provisional Application No. 61/576,490, filed 16 Dec. 2011, and U.S. Provisional Application No. 61/724,475, filed 9 Nov. 2012, which are incorporated herein by reference in its entirety.

BACKGROUND OF THE INVENTION

Described herein are compositions useful, for example, to attract the brown marmorated stink bug (BMSB), *Halyomorpha halys*. The compositions may contain various combinations of cis and/or trans stereoisomers of 10,11-epoxy-1-bisabolen-3-ol produced from (R)-citronellal, and/or cis and/or trans stereoisomers of 10,11-epoxy-1-bisabolen-3-ol produced from (S)-citronellal as described herein. These compositions contain two major components of the aggregation pheromone of *Halyomorpha halys*: (3S,6S,7R,10S)-10,11-epoxy-1-bisabolen-3-ol (1) and (3R,6S,7R,10S)-10,11-epoxy-1-bisabolen-3-ol (3) also described herein. Furthermore, also described are methods for attracting *Halyomorpha halys* to an object or area, involving treating the object or area with a *Halyomorpha halys* attracting composition containing a *Halyomorpha halys* attracting effective amount of the compositions described herein. Also described are kits for attracting *Halyomorpha halys* where the kit may contain (a) a first attractant containing the compositions described herein on a first carrier and (b) a second attractant containing methyl (2E,4E,6Z)-decatrieonate on a second carrier or on said first carrier.

The brown marmorated stink bug, *Halyomorpha halys* (Stål) (BMSB), is an invasive pest species from Asia and is now well established throughout the U.S. mid-Atlantic region. BMSB has been officially detected by responsible authorities in 39 states and the District of Columbia. BMSB is considered a polyphagous pest of many specialty crops in Asia and the United States including tree fruit, vegetables, shade trees, and row crops with significant economic damage reported in the United States (Leskey, T. C., et al., Pest Status of the Brown Marmorated Stink Bug, *Halyomorpha halys* (Stål), in the USA, Outlooks on Pest Management, DOI: 10.1564/23oct07 (2012a); Leskey T. C., et al., Impact of the invasive brown marmorated stink bug, *Halyomorpha halys* (Stål) in mid-Atlantic tree fruit orchards in the United States: case studies of commercial management, Psyche, doi: 10.1155/2012/535062 (2012b)).

Stink bugs native to North America have long been managed with broad-spectrum insecticides. However, since the passage of the Food Quality Protection Act in 1996 many broad-spectrum materials have been lost or severely curtailed through regulatory measures, thus allowing populations of native stink bugs, considered to be secondary pests, to become more prevalent. Subsequently, as BMSB has become well established, populations have exerted tremendous season-long and unprecedented pest pressure complicating management for growers and leading to devastating levels of injury in many crops (Leskey et al. 2012 a, b)

Monitoring tools are used to assess the presence, abundance, and seasonal activity of pests and their natural enemies to determine the need for and the timing of insecticide applications. Stink bug species are typically monitored in cropping systems using sweep nets, beating samples, pheromone-baited traps and/or black light traps. Among native stink bugs in tree fruit, baited yellow pyramid traps and baited mullein plants were effective at monitoring native *Euschistus* spp., while *Acrosternum hilare* was monitored in vegetable and row crops using black light traps (Leskey, T. C., and H. W. Hogmire, J. Econ. Entomol., 98: 143-153 (2005); Hogmire, H. W., and T. C. Leskey, J. Entomol. Sci. 41: 9-21 (2006); Krupke, C. H., et al., J. Econ. Entomol., 94: 1500-1505 (2001); Kamming a, K. L., et al., Environ. Entomol., 38: 1716-1723 (2009)). Black light traps have been evaluated for BMSB in Japan and in New Jersey (Moriya, S., et al., Bull. Fruit Tree Res. Stn. 14: 79-84 (1987); Nielsen, A. L., and G. C. Hamilton, Ann. Entomol. Soc. Am., 102: 608-616 (2009)).

The aggregation pheromone of *Plautia stali* Scott, methyl (2E,4E,6Z)-decatrienoate, is cross-attractive to BMSB (Sugie, H., et al., Appl. Entomol. Zool., 31: 427-431 (1996); Lee, K.-C., et al., Korean J. Appl. Entomol. Zool., 41: 233-238 (2002); Tada, N., et al., Ann. Rep. Plant Prot., 52: 224-226 (2001a); Tada, N., et al., Ann. Rep. Plant Prot., 52: 227-229 (2001b); Aldrich, J. R., et al., J. Chem. Ecol., 33: 801-815 (2007); Khrimian, A., et al., J. Ag. and Food Chemistry, 56: 197-203 (2008)). Adults are reliably attracted late in the season but extensive early-season trials revealed this compound was not by itself attractive ((Khrimian et al. 2008; Leskey T. C., et al., Journal of Entomological Science, 47: 76-85 (2012c)). Because of the significant threat posed by BMSB in the absence of monitoring tools to provide them with information regarding BMSB presence and pressure, growers have turned to aggressive calendar-based insecticide programs to combat BMSB populations. Therefore the need for a season-long attractant for BMSB is critical in order for growers to make informed pest management decisions. Furthermore, such an attractant could be used to develop effective attract-and-kill or other management technologies to limit insecticide inputs into agroecosystems.

Thus there is a need for attractants to provide more reliable and accurate monitoring of BMSB infestations and populations.

SUMMARY OF THE INVENTION

There are provided compositions useful, for example, to attract the brown marmorated stink bug, *Halyomorpha halys*. The compositions may contain various combinations of cis and/or trans stereoisomers of 10,11-epoxy-1-bisabolen-3-ol produced from (R)-citronella, and/or trans and/or cis stereoisomers of 10,11-epoxy-1-bisabolen-3-ol produced from (S)-citronella as described herein. These compositions contain two major components of the aggregation pheromone of *Halyomorpha halys*: (3S,6S,7R,10S)-10,11-epoxy-1-bisabolen-3-ol (1) and (3R,6S,7R,10S)-10,11-epoxy-1-bisabolen-3-ol (3). Also, there are provided methods for attracting *Halyomorpha halys* to an object or area, involving treating the object or area with a *Halyomorpha halys* attracting composition containing a *Halyomorpha halys* attracting effective amount of the compositions described herein.

Furthermore there are provided kits for attracting *Halyomorpha halys*, where the kit may contain (a) a first attractant containing the compositions described herein on a first carrier, and (b) a second attractant containing methyl (2E,4E,6Z)-decatrieonate on a second carrier or on the first carrier.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 20 shows synthesis of epoxybisaboladienes, suspected minor components of *H. halys* pheromone 4, 5, and 6, as described below.

DETAILED DESCRIPTION OF THE INVENTION

Figure 1:
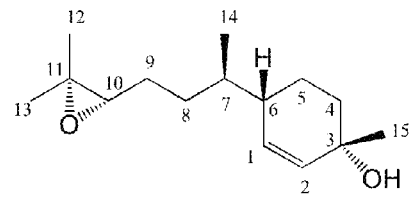
FIG. 1 shows the structures and names of male-specific compounds identified from brown marmorated stinkbug, *Halyomorpha halys*, as described below.
Figure 1:
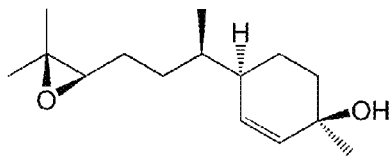
Figure 1:
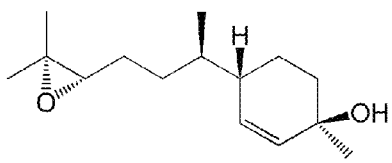
Figure 1:
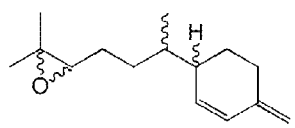
Figure 1:
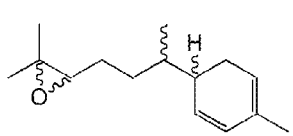
Figure 1:
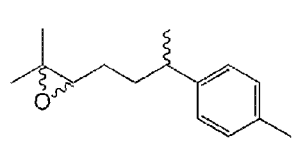

Described herein are compositions useful, for example, to attract the brown marmorated stink bug, *Halyomorpha halys*. The compositions contain various combinations of cis and/or trans stereoisomers of 10,11-epoxy-2-bisabolen-3-ol produced from (R)-citronellal, and/or cis and/or trans stereoisomers of 10,11-epoxy-2-bisabolen-3-ol produced from (S)-citronellal as described herein. These compositions also include single stereoisomers comprising the pheromone of *Halyomorpha halys*: (3S,6S,7R,10S)-10,11-epoxy-1-bisabolen-3-ol (1) and (3R,6S,7R,10S)-10,11-epoxy-1-bisabolen-3-ol (3). Furthermore, there are described methods for attracting *Halyomorpha halys* to an object or area, involving treating the object or area with a *Halyomorpha halys* attracting composition containing a *Halyomorpha halys* attracting effective amount of the compositions described herein.

The compounds described herein (useful, for example, in attracting BMSB) may be applied with a carrier component or carrier (e.g., agronomically or physiologically or pharmaceutically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insect pheromones in general and are well known in the art. Suitable carriers are well-known in the art and are selected in accordance with the ultimate application of interest. Agronomically acceptable substances include aqueous solutions, glycols, alcohols, ketones, esters, hydrocarbons, halogenated hydrocarbons, polyvinyl chloride; in addition, solid carriers such as clays, cellulosic and rubber materials and synthetic polymers. The carrier or carrier material as used herein is defined as not including the body of an insect (e.g., *Halyomorpha halys*).

The amount of the composition for attracting *Halyomorpha halys* used will be at least an effective amount (i.e., 10 mg or more). The term "effective amount," as used herein, means the minimum amount of the composition needed to attract *Halyomorpha halys* to a treated area or object or locus when compared to the same area or object or locus which is untreated. Of course, the precise amount needed will vary in accordance with the particular composition used; the type of area or object to be treated; the number of days of attractiveness needed; and the environment in which the area or object or locus is located. The precise amount of the composition can easily be determined by one skilled in the art given the teaching of this application. For example, one skilled in the art could follow the procedures utilized below; the composition would be statistically significant in comparison to a control (e.g., water). Generally, the concentrations of synthetic chemicals discussed herein on rubber septa would range from about 10 mg to about 250 mg (e.g., 10 to 250 mg), monitoring traps would generally use about 50 mg while attract and kill may use about 250 mg, and release rates could generally be about 0.05 to about 1 mg (e.g., 0.05 to 1 mg) per septum per day. For example, the trap could contain 10 mg to 100 mg per trap of a composition comprising (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and optionally a carrier material or carrier.

The compositions described herein may or may not contain a control agent for *Halyomorpha halys*, such as a biological control agent or an insecticide known in the art to kill *Halyomorpha halys*. Other compounds may be added to the composition provided they do not substantially interfere with the intended activity of the composition; whether or not a compound interferes with attractant activity can be determined, for example, by the procedures utilized below.

The compositions may also be in a kit for attracting *Halyomorpha halys*. The kit may contain (a) a first attractant containing the compositions described herein on a first carrier, and (b) a second attractant containing methyl (2E,4E,6Z)-decatrieonate on a second carrier or on the first carrier. The kit may further contain an insect trap for housing the first and second carriers. The kit may further contain written instructions directed to deploying the attractants at separate seasonal times. The kit may further contain one or more insecticides on the third carrier.

Unless defined otherwise, all technical and scientific terms used herein have the same meaning as commonly understood by one of ordinary skill in the art to which the invention belongs. The term "about" is defined as plus or minus ten percent; for example, about 100° C. means 90° C. to 110° C. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and Methods. Rearing of Insects: The *H. halys* colony was established in 2007 from adults collected in Allentown, Pa., and reared on a diet of organic green beans, water (supplied by two 7 cm×2-cm OD test tube), and seeds (2:1 sunflower:buckwheat seed) in plastic containers (21 cm×21 cm OD). Eggs were collected periodically throughout the study and put into separate containers containing the same diet. After emerging, the five stages of nymphal instars were reared in the same container until they developed into adults. Within 1 or 2 days after they became adults, and male and female were separated and reared in different containers. Insects were maintained in Thermo Forma® chambers (Thermo Fisher Scientific) at 25° C. and 72% relative humidity with 16L:8D photoperiod. The colony was annually replenished with ~20 field-collected bugs collected in Beltsville, Md.

Semiochemical Collection and Isolation: Originally the volatiles were separately collected from two groups of 2-day-old virgin males and females (3 bugs per group). After the semiochemical was confirmed as male-specific, the volatiles were collected from different numbers per container of virgin males only (i.e., 1, 2, 3, 5, 7, 9, and 20 virgin males per group). The males and females were separately put into two 1-liter 4-necked glass containers. Humidified air was drawn into the containers through 6-14 mesh activated charcoal (Fisher Scientific, Pittsburgh, Pa.) and out of the containers through two traps (15 cm×1.5-cm OD) containing Super Q (200 mg each; Alltech Associates, Inc., Deerfield, Ill.) by vacuum (~1 liter/min) (Zhang, A, et al., Zeitschrift für Naturforschung, Section C Biosciences, 57: 553-558 (2002)). Insects were fed with organic green beans (replaced weekly) and water on cotton balls, and aerated continuously for 20 days and up to 90 days depending on insect living conditions at room temperature and 16L:8D photoperiod. The adsorbent traps were changed every day (some of them in 3 days for weekend) and the adsorbents were eluted with methylene chloride (0.5 ml/each sample). The solutions were stored in −30° C. before analyses.

Analytical Methods. Analysis of Semiochemicals: An Agilent 6890 gas chromatograph (GC) equipped with an auto sampler and a 30-m×0.25-mm ID, 0.25-μm film-thickness HP-5 (J&W Scientific Inc., Folsom, Calif.) capillary column in the splitless mode with hydrogen as carrier (1.4 ml/min) was used for quantitative analysis. 1-tetradecene (10 ng/μl and 1 ng/μl in $CH_2Cl_2$) was used as external standard for quantitative analysis. The oven temperature was programmed at 40° C. for 2 minutes, then heated to 280° C. at 15° C./minute and held for 10 minutes. Electron impact mass spectrometry (EI MS) was conducted on an Agilent 6890 GC coupled to an Agilent 5973 Mass Selective Detector using a 60-m×0.25-mm ID, 0.25-μm film-thickness DB-WAXETR (J&W Scientific Inc., Folsom, Calif.) capillary column at 50° C. for 2 minutes, then programmed to 250° C. at 15° C./minute and held for 15 minutes or a 60-m×0.25-mm ID, 0.25-μm film-thickness DB-5MS capillary column (50° C. for 2 minutes, then programmed to 280° C. at 20° C./minute and held for 15 minutes) with helium as carrier gas unless other temperature programs are indicated. A 70 eV electron beam was employed for sample ionization. Chemical ionization mass spectrometry (CI MS) spectra were obtained from an Agilent GC/MS spectrometer with ammonia ($NH_3$) or with deuteroammonia ($ND_3$) as reagent gases using the DB-WAX-etr columns and the same conditions as above. Cold on-column injections were performed on Agilent 7890A GC and Agilent GC/MS spectrometer using HP-5 capillary columns (30-m×0.32-mm ID, 0.25-μm film-thickness HP-5 capillary column (50° C. for 2 minutes, then programmed to 280° C. at 15° C./minute and held for 15 minutes).

Analysis of synthetic samples: Routine GC analyses were performed on a Shimadzu 17A (Shimadzu Scientific Instruments, Inc., Columbia, Md.) gas chromatograph equipped with a flame ionization detector, an auto-sampler AOC-20s and auto-injector AOC-20i, and a HP-5 capillary column (30 m×0.25 mm×0.25 μm film). Hydrogen was used as carrier gas at 1 ml/minute. Column temperature was maintained at 80° C. for 5 minutes and then raised to 280° C. at 10° C./minute. Chiral GC analyses were performed on 25 m×0.25 mm HYDRODEX® β-6TBDM (heptakis-(2,3-di-O-methyl-6-O-t-butyldimethylsilyl)-β-cyclodextrin, Macherey-Nagel GmbH & Co. KG, Düren, Germany) in isothermal mode at 85° C. Hydrogen was used as carrier gas at 1.5 ml/minute. Electron-ionization (EI) mass spectra were obtained at 70 eV with an Agilent Technologies 5973 mass selective detector interfaced with 6890 N GC system equipped with a 30 m×0.25 mm i.d.×0.25 μm film HP-5MS column. Column temperature was maintained at 50° C. for 2 minutes and then raised to 270° C. at 10° C./minute. Helium was used as a carrier gas at 1 ml/minute. Thin layer chromatography (TLC) analyses were conducted on Whatman AL SIL G/UV plates using 20% ethanol solution of phosphomolybdic acid and/or UV for visualization of spots. Flash chromatography was carried out with 230-400 mesh silica gel (Fisher Scientific, Fair Lawn, N.J.). $^1$H NMR spectra were obtained at 600 MHz and $^{13}$C spectra at 151 MHz on a Bruker AVIII-600 MHz spectrometer. Chemical shifts are reported in δ units and referenced to the residual $CD_2Cl_2$ solvent signal; coupling constants are reported in Hz. $^1$H-$^1$H COSY, $^{13}$C-DEPT 135, HMBC, and HSQC spectra were also recorded to assign protons and carbons in the synthetic molecules. Optical rotations were obtained on a Perkin-Elmer 241 polarimeter with a 1.0 mL cell.

GC-HRMS analyses were performed on TOF EI mode on a Waters GCT Premier instrument equipped with a DB5-MS column. All reagents and solvents were purchased from Aldrich Chemical Co. unless otherwise specified. (S)-(−)-Citronellal (97% ee) was purchased from Sigma-Aldrich (Milwaukee, Wis.) and (R)-(+)-Citronellal (98% ee) was purchased from Takasago International (Tokyo, Japan).

Identification and Synthesis. Preparation of cis and trans bisaboladienols 11 and 12 (FIG. 6): (R)-Citronellal was converted to α,β-unsaturated aldehyde 9 which was further cyclized to cyclohexenone 10 following Hagiwara et al. 2002 (Hagiwara, H., et al., J. Chem. Soc., Perkin Trans., 1: 895-900). For further conversion of 10, a procedure of Zahn et al., (2008) was followed with some modifications presented below (Zahn, D. K., et al., J. Chem. Ecol., 34: 238-251).

A dry three-neck round-bottom flask, fitted with a dropping funnel, magnetic stirrer, thermometer, and $N_2$ inlet, was charged with ketone 10 (3.006 g, 14.57 mmol) and 90 mL dry ether. The flask was cooled to −20° C. and methyl lithium (12 ml of 1.6 M in ether; 19.2 mmol) was slowly added to the solution while maintaining the reaction temperature between −15° and −20° C. After the addition was completed (about 30 minutes), the reaction mixture was allowed to warm to room temperature within 2 hours and stirred for another 2 hours or until TLC showed very little starting ketone 10 present. The reaction mixture was cooled to 0° to −5° C., then treated with a saturated ammonium chloride solution until pH reached ~7, and the layers were separated. The aqueous layer was extracted with hexane:ether, 1:1; the combined organic extracts were washed with brine and dried with sodium sulfate. After evaporation of the solvent, the crude mixture was flash chromatographed on silica gel using hexane:ethyl acetate, 8:1 to 5:1. A fraction (1.02 g, 32%) with Rf 0.25 (hexane:ethyl acetate, 5:1) was identified as a diastereomeric mixture of cis-bisaboladienols 11, and the more polar fraction (1.25 g, 38%) with Rf 0.17 (hexane/ethyl acetate, 5:1) was found to be a mixture of two trans-bisaboladienols 12. Bisaboladienols 11 and 12 were well separated on HP-5MS capillary column in GC-MS analysis. However, two cis stereoisomers in mixture 11 and two trans-stereoisomers in 12 were not separated from each other. Mass spectra of 11 and 12 were identical with those previously published (Zhan, et al., 2008).

Preparation of cis- and trans-epoxybisabolenols 7 and 8 (FIG. 6): A mixture of cis-bisaboladienols 11 (two diastereomers, 148 mg, 0.67 mmol) was stirred with meta-chloroperbenzoic acid (MCPBA, 159 mg of 80-85%-pure, Aldrich Chem. Co., 0.74 mmol) in the presence of anhydrous sodium acetate (61 mg) in dichloromethane (DCM, 4 ml, dried over $CaH_2$) at 0° to 5° C. for 3.5 hours. Water (5 ml) was added and the layers were separated. The aqueous layer was extracted with DCM (3×5 ml), and combined organic extracts were washed with a sodium bicarbonate solution (to remove m-chlorobenzoic acid that had formed), washed with brine, and then dried with sodium sulfate. After evaporation of the solvent, the residue was flash-chromatographed on silica (hexane:ethyl acetate, 2:1) to give the cis-epoxybisabolenols 7 (four stereoisomers, 131 mg, 82%). Rf 0.25 (hexane/ethyl acetate, 2:1). GC-EIMS (m/z, relative abundance): 220 (2, $M^+$−18), 205 (6), 202 (3), 187 (5), 165 (26), 159 (9), 147 (18), 145 (10), 138 (30), 134 (50), 132 (39), 121 (39), 119 (43), 109 (40), 105 (31), 93 (72), 91 (50), 79 (45), 77 (36), 71 (59), 69 (26), 67 (27), 59 (29), 55 (33), 43 (100), 41 (42). The data are in agreement with those previously published (Zahn et al. 2008) and matched those obtained for main male-specific compound found in H. halys extract.

Analogously, a mixture of trans-bisaboladienols 12 (two diastereomers, 348 mg, 1.57 mmol) was epoxidized with MCPBA (374 mg) in the presence of NaOAc (143 mg) in DCM (10 ml) to provide trans-epoxybisabolenols 8 (four stereoisomers, 204 mg, 55%). Rf 0.28 (hexane/ethyl acetate, 4:3). GC-EIMS (m/z, relative abundance): 220 (2, $M^+$−18), 205 (5), 202 (2), 187 (5), 165 (28), 159 (10), 147 (16), 145 (14), 138 (16), 134 (48), 132 (61), 121 (37), 119 (52), 109 (40), 105 (34), 93 (72), 91 (50), 79 (33), 77 (35), 71 (54), 69 (25), 67 (25), 59 (27), 55 (32), 43 (100), 41 (43).

Preparation of mixtures of cis and trans epoxybisabolenols 7 and 8 without purification of intermediates 11 and 12: A crude mixture of 11 and 12 from the reaction of 10 with MeLi (3.30 g) was epoxidized with MCPBA (3.44 g) as described above to yield a crude mixture (3.10 g) containing 21% cis-epoxybisabolenols 7, 41% trans epoxybisabolenols 8, and 37% of 1,2,10,11-diepoxybisabolan-3-ol represented by sixteen stereoisomers. GC analysis revealed three broad peaks related to isomeric 1,2,10,11-diepoxybisabolan-3-ols that had similar mass spectra. GC-EIMS of 1,2,10,11-diepoxybisabolan-3-ols (m/z, relative abundance): 175 (2), 165 (3), 163 (3), 151 (5), 147 (6), 138 (19), 125 (31), 109 (51), 95 (53), 81 (49), 71 (44), 69 (25), 55 (30), 43 (100), 41 (40). GC-CIMS ($NH_3$, m/z): 272 ($M^+$+18), 254 ($M^+$), 237, 221, 219, 203. The crude mixture was tested in field trials as lure #20 with a loading of 38 mg (or 8 mg cis epoxybisabolenols 7) per rubber septum. A part of this crude mixture (2.30 g) was purified by flash chromatography (hexane:ethyl acetate, 5:4) to give three fractions: No. 1, 333 mg 7 of 91% purity; No. 2, 230 mg containing 32% 7, 65% 8, and 3% unknowns; No. 3, 600 mg containing 8. By mixing No. 1 with 126 mg of No. 2 we obtained 459 mg of mixture of 7 and 8 in a 3:1 ratio. The latest product (mixture of 7 and 8 in a 3:1 ratio) was tested in the field as lure #21 with the loading of 10.67 mg (or 8 mg of 7) per lure.

Figure 7:
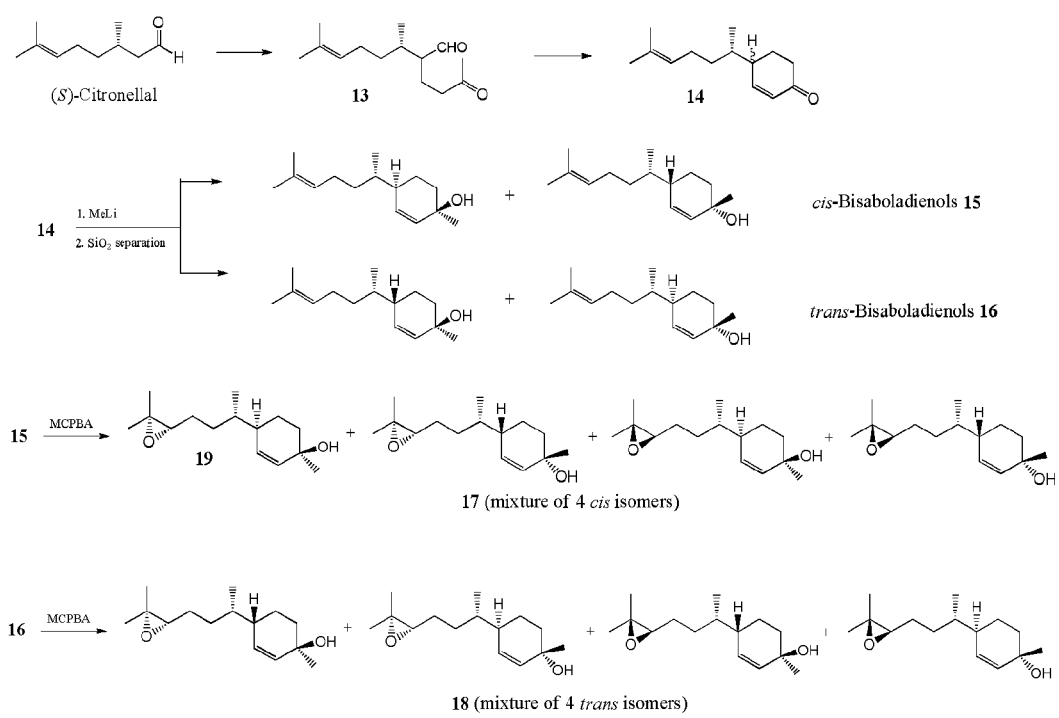
FIG. 7 shows a non-stereoselective syntheses of four-component mixtures of cis and trans-epoxybisabolenols 17 and 18 from (S)-citronellal as described below.

Preparation of cis and trans bisabolenadienols 15 and 16 (FIG. 7): (S)-Citronellal was converted to aldehyde 13 which was further cyclized to cyclohexenone 14 following Hagiwara et al. 2002 (FIG. 7). Analogously to the procedure described for 10, aldehyde 14 (13.52 g, 65.52 mmol) was dissolved in 800 mL dry ether and allowed to react with methyl lithium (53 ml of 1.6 M in ether; 84.80 mmol) at −15° and −20° C. After regular work-up and flash chromatography on silica gel using hexane:ethyl acetate, 8:1 to 5:1, alcohol 15 (4.14 g, 28%), Rf 0.25, hexane:ethyl acetate, 5:1, and 16 (4.75 g, 33%), Rf=0.17, hexane:ethyl acetate, 5:1, were separated. Bisaboladienols 15 and 16 were well separated on HP-5MS capillary column. However, two trans diastereomers of 15 provided no separation on HP-5MS, and two cis-bisaboladienols of 16 were only partially separated from each other. Mass spectra of 15 and 16 matched those previously described in literature (Zhan, et al., 2008).

Figure 9:
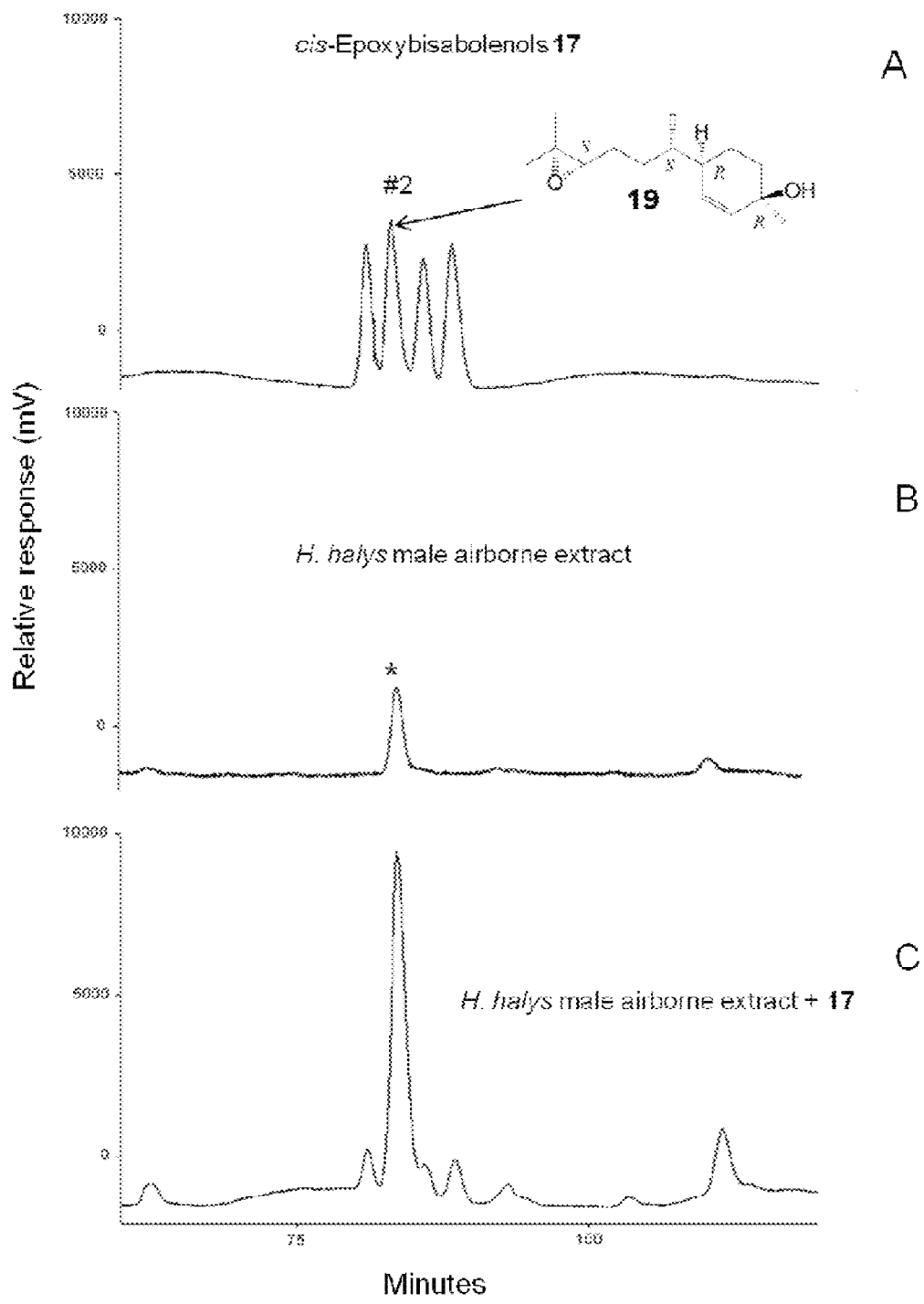
FIG. 9 shows GC-FID (gas chromatography coupled with flame ionization detection) analyses on HYDRODEX-β-6TBDM as described below. Part A: four-component cis-epoxybisabolenols 17; Part B: *H. halys* male airborne extract with the main constituent marked with an asterisk (*); Part C: cis-Epoxybisabolenols 17 plus *H. halys* male airborne extract.

Preparation of cis epoxybisabolenols 17 (FIG. 7): A diastereomeric mixture 15 (1.157 g, 5.21 mmol) was added to the stirred suspension of dry sodium acetate (471 mg, 5.74 mmol) in dry DCM (35 ml), and the flask was cooled to 0° C. MCPBA (1.237 g) was added in small portions at 0° C. and the stirring was continued at that temperature for 4.5 hours. The mixture was poured into ice-water (20 ml) and extracted with DCM (3×20 ml). The combined organic extract was washed with a sodium bicarbonate solution and dried with sodium sulfate. After evaporation of the solvent, the remainder was flash-chromatographed on $SiO_2$ with hexane:ethyl acetate, 2:1, to provide cis epoxybisabolenols 17 (994 g, 80%) as a mixture of four stereoisomers. Stereoisomers 17 were not separated on HP-5MS column but were almost baseline-separated by GC-FID analysis on a chiral HYDRO-DEX-6TBDM column (FIG. 9, part A).

GC-EIMS (m/z, relative abundance): 220 (3, $M^+$−18), 205 (3), 202 (3), 187 (4), 165 (10), 159 (9), 145 (10), 147 (14), 138 (13), 134 (38), 132 (42), 121 (35), 119 (52), 109 (27), 105 (35), 93 (87), 91 (66), 79 (42), 77 (44), 71 (53), 69 (25), 67 (22), 59 (26), 55 (33), 43 (100), 41 (48). The data are in agreement with those previously published (Zahn et al. 2008) and matched those obtained for compound 1 found in *H. halys* male extract. GC-CIMS ($MH_3$, m/z, relative abundance): 256 ($M^+$+18, 1), 238 ($M^+$, 13), 221 ($M^+$+1−18,100), 203 (41), 163 (18), 127 (26).

Preparation of trans epoxybisabolenols 18 (FIG. 7): A diastereomeric mixture of cis-bisaboladienols 16 (815 mg, 3.67 mmol) was epoxidized with m-chloroperbenzoic acid (871 mg) in the presence of sodium acetate (331 mg, 4.04 mmol) in DCM (25 ml) analogously to described above to yield after flash chromatography cis-epoxybisabolenols 18 (682 mg, 78%) as a mixture of four stereoisomers (FIG. 7).

GC-EIMS (m/z, relative abundance): 220 (3, $M^+$−18), 205 (3), 202 (3), 187 (4), 165 (14), 159 (10), 145 (14), 147 (13), 138 (9), 134 (40), 132 (58), 121 (36), 119 (61), 109 (28), 105 (40), 93 (93), 91 (68), 79 (35), 77 (46), 71 (51), 69 (24), 67 (22), 59 (25), 55 (33), 43 (100), 41 (49). GC-CIMS ($MH_3$, m/z, relative abundance): 238 ($M^+$, 16), 221 ($M^+$+1−18,100), 203 (42), 163 (16), 127 (24).

Preparation of (3S,6S,7R)-1,10-bisaboladien-3-ol (20) and (3S,6R,7R)-1,10-bisaboladien-3-ol (21) (FIG. 11): Chloro(1,5-cyclooctadiene)rhodium(I)dimer, ([Rh(cod)Cl]$_2$, 77 mg, 0.16 mmol) and (R)-(−)-2,2'-bis(diphenylphosphino)-1,1'-binaphthalene ((R)-BINAP, 191 mg, 0.31 mmol) were placed under $N_2$ in a round-bottom three-neck flask. Dry tetrahydrofuran (30 ml) was added to the mixture and the resulting solution was stirred at room temperature for 30 minutes and then cooled to 0° C. A solution of ketone 10 (613 mg, 2.96 mmol) was added to the mixture followed by trimethylaluminum (3 ml of 2.0 M in heptane; 6.0 mmol) maintaining the temperature 0° to −5° C. After stirring for 4 hours at 0° C., the flask was left in a refrigerator at 0° to 2° C. for 20 hours. The mixture was poured into $NH_4Cl$ solution, acidified with 10% HCl to pH 3-4, and extracted with hexane:ether, 5:1. Combined organic extracts were washed with water, washed with brine, and dried with $Na_2SO_4$. After evaporation of the solvent, the residue was flash chromatographed on $SiO_2$ with hexane:ethyl acetate, 6:1 to 3:1, to provide two main fractions.

The less polar fraction (258 mg) was further purified on $SiO_2$ with DCM:ethyl acetate 40:1 to remove remnants of unreacted ketone and provide 20 (156 mg, 24%) of 96% chemical purity by GC-MS. GC retention time and Rf (0.45, hexane/ethyl acetate 3:1) of 20 matched those of mixture 11 thus indicating that 20 is a cis bisaboladienol. GC-MS (m/z, %): 222 ($M^+$, 4), 207 (17), 204 (13), 189 (10), 161 (18), 148 (10), 137 (24), 119 (69), 109 (33), 93 (41), 69 (100), 55 (29), 43 (38), 41 (50). $[\alpha]_D^{20}$=−1.24 (c 4.27, DCM).

$^1$H NMR (500 MHz, $CD_2Cl_2$): 0.87 (d, J=6.9 Hz, H-14), 1.22 (m, H-8a), 1.26 (s, H-15), 1.42 (m, H-8b), 1.46 (m, H-5a), 1.54 (m, H-4a), 1.56 (m, H-7), 1.56 (m, H-5b), 1.64 (s, H-12), 1.71 (s, H-13), 1.82 (d, J=11.5 Hz, H-4-b), 1.98 (m, H-9a), 2.05 (m, H-9b), 2.05 (m, H-6), 5.14 (tt, J=7.2, 1.4 Hz, H-10), 5.63 (dt, J=10.1, 1.5, H-1), 5.67 (dt, J=10.1, 1.9, H-2).

$^{13}$C NMR (126 MHz, $CD_2Cl_2$): 15.5 (C-14), 17.3 (C-12), 20.1 (C-5), 25.4 (C-13), 26.0 (C-9), 29.5 (C-15), 34.2 (C-8), 36.3 (C-7), 37.3 (C-4), 40.5 (C-6), 67.0 (C-3), 124.7 (C-10), 131.2 (C-11), 133.6 (C-2), 133.9 (C-1). HREIMS m/z 222.2001 (calculated for $C_{15}H_{26}O$, 222.1984).

The more polar fraction (75 mg) was further purified on $SiO_2$ with DCM:ethyl acetate 30:1 to furnish 94% pure trans bisaboladienol 21 (35 mg, 5%), GC retention time and Rf (0.32, hexane/ethyl acetate 3:1) of which matched those of 12. $[\alpha]_D^{20}$=−58.82 (c 0.70, DCM). GC-MS (m/z, %): 222 ($M^+$, 4), 207 (26), 204 (25), 189 (7), 161 (21), 148 (6), 137 (34), 119 (91), 109 (30), 93 (53), 69 (100), 55 (29), 43 (37), 41 (49).

$^1$H NMR (500 MHz, $CD_2Cl_2$): 0.89 (d, J=6.8 Hz, H-14), 1.19 (m, H-8a), 1.26 (s, H-15), 1.40 (m, H-8b), 1.43 (m, H-5a), 1.48 (m, H-7), 1.64 (m, H-4a), 1.64 (s, H-12), 1.71 (s, H-13), 1.72 (m, H-5b), 1.87 (d, J=12.2 Hz, H-4-b), 1.96 (m, H-9a), 2.05 (m, H-9b), 2.12 (m, H-6), 5.13 (t, J=7.2 Hz, H-10), 5.57 (ddd, J=10.1, 2.1, 1.1, H-1), 5.61 (ddd, J=10.1, 2.5, 1.6, H-2).

$^{13}$C NMR (126 MHz, $CD_2Cl_2$): 16.2 (C-14), 17.3 (C-12), 24.2 (C-5), 25.4 (C-13), 26.0 (C-9), 28.3 (C-15), 33.8 (C-8), 36.4 (C-7), 38.4 (C-4), 40.7 (C-6), 69.4 (C-3), 124.7 (C-10), 130.5 (C-1), 131.1 (C-11), 135.1 (C-2). HREIMS $M^+$ 222.2007 (calculated for $C_{15}H_{26}O$, 222.1984).

Preparation of (3R,6R,7R)-1,10-bisaboladien-3-ol (22) and (3R,6S,7R)-1,10-bisaboladien-3-ol (23) (FIG. 11): Analogously to the above experiment, the reaction of ketone 10 (1.620 g, 7.86 mmol) with trimethylaluminum (7.9 ml of 2.0 M in heptane; 15.80 mmol) in the presence of [Rh(cod)Cl]$_2$ (194 mg, 0.39 mmol) and (S)-BINAP (588 mg, 0.94 mmol) in dry THF (80 ml) and subsequent purification of crude mixture on $SiO_2$ with hexane:ethyl acetate, 6:1 to 3:1, yielded unreacted ketone (107 mg) and two fractions corresponding to cis and trans bisaboladienols. The first fraction (660 mg) was further purified with hexane:ethyl acetate: MeOH, 10:1:0.2 to 10:1:0.4, to provide 22 (531 mg, 30%) of 96% purity. $[\alpha]_D^{20}$=−15.43 (c 1.27, DCM). GC-MS (m/z, %): 222 (M+, 5), 207 (19), 204 (19), 189 (8), 161 (19), 148 (13), 137 (26), 119 (82), 109 (36), 93 (50), 69 (100), 55 (32), 43 (33), 41 (48).

$^1$H NMR (500 MHz, $CD_2Cl_2$): 0.91 (d, J=6.8 Hz, H-14), 1.22 (m, H-8a), 1.26 (s, H-15), 1.41 (m, H-8b), 1.51 (m, H-5a), 1.53 (m, H-7), 1.55 (m, H-4a), 1.60 (m, H-5b), 1.63 (s, H-12), 1.71 (s, H-13), 1.82 (m, H-4-b), 1.97 (m, H-9a), 2.03 (m, H-6), 2.06 (m, H-9b), 5.14 (t, J=7.0 Hz, H-10), 5.67 (s, H-1), 5.67 (s, H-2).

$^{13}$C NMR (126 MHz, $CD_2Cl_2$): 16.2 (C-14), 17.3 (C-12), 22.1 (C-5), 25.4 (C-13), 26.0 (C-9), 29.5 (C-15), 33.6 (C-8), 36.3 (C-7), 37.5 (C-4), 41.1 (C-6), 67.1 (C-3), 124.7 (C-10), 131.1 (C-11), 132.7 (C-1 or C-2), 133.9 (C-2 or C-1). HREIMS M+ 222.2000 (calculated for $C_{15}H_{26}O$, 222.1984).

The second more polar fraction (143 mg) was purified with hexane:ethyl acetate, 4:1 to 3:1, to provide 23 (78 mg, 5%) of 95% purity. $[\alpha]_D^{20}$=+32.52 (c 3.05, $CH_2Cl_2$). GC-MS (m/z, %): 222 (M+, 5), 207 (28), 204 (30), 189 (8), 161 (28), 148 (6), 137 (36), 119 (100), 109 (34), 93 (61), 69 (100), 55 (29), 43 (33), 41 (45).

$^1$H NMR (500 MHz, $CD_2Cl_2$): 0.85 (d, J=6.9 Hz, H-14), 1.20 (m, H-8a), 1.26 (s, H-15), 1.40 (m, H-8b), 1.41 (m, H-5a), 1.53 (m, H-7), 1.63 (m, H-4a), 1.63 (s, H-12), 1.69 (m, H-5b), 1.71 (s, H-13), 1.87 (d, J=11.9 Hz, H-4-b), 1.97 (m, H-9a), 2.05 (m, H-9b), 2.14 (m, H-6), 5.14 (t, J=7.1 Hz, H-10), 5.53 (d7, J=10.1, 1.1, H-1), 5.61 (dt, J=10.1, 2.0, H-2).

$^{13}$C NMR (126 MHz, $CD_2Cl_2$): 15.4 (C-14), 17.3 (C-12), 22.3 (C-5), 25.4 (C-13), 25.9 (C-9), 28.2 (C-15), 34.1 (C-8), 36.3 (C-7), 38.3 (C-4), 40.2 (C-6), 69.4 (C-3), 124.7 (C-10), 130.5 (C-1), 131.1 (C-11), 134.8 (C-2). HREIMS M+ 222.1992 (calculated for $C_{15}H_{26}O$, 222.1984).

Preparation of (3R,6R,7S)-1,10-bisaboladien-3-ol (24) and (3R,6S,7S)-1,10-bisaboladien-3-ol (25) (FIG. 11): Analogously to experiment described above, ketone 14 (3.090 g, 15.0 mmol) was reacted with trimethylaluminum (15 ml of 2.0 M in heptane; 30.0 mmol) in the presence of [Rh(cod)$Cl_2$], 370 mg, 0.75 mmol) and (S)-BINAP (1.121 g, 1.80 mmol) in dry THF (190 ml). Crude reaction products were purified by flash-chromatographed on $SiO_2$ with hexane:ethyl acetate:MeOH, 10:0.5:0.4, to provide a material (1.620 g) that was further chromatographed with hexane:ethyl acetate, 6:1 to 4:1, to furnish two fractions.

The less polar fraction was identified as compound 24 (860 mg, 26%). $[\alpha]_D^{20}$=+1.1 (c 2.05, DCM). GC-MS (m/z, %)?] 222 (M+, 5), 207 (17), 204 (11), 189 (10), 161 (16), 148 (11), 137 (27), 119 (68), 109 (34), 93 (34), 69 (100), 55 (27), 43 (35), 41 (42).

$^1$H NMR (500 MHz, $CD_2Cl_2$): 0.87 (d, J=6.9 Hz, H-14), 1.23 (m, H-8a), 1.26 (s, H-15), 1.42 (m, H-8b), 1.46 (m, H-5a), 1.54 (m, H-4a), 1.56 (m, H-7), 1.56 (m, H-5b), 1.64 (s, H-12), 1.71 (s, H-13), 1.82 (m, H-4-b), 1.98 (m, H-9a), 2.06 (m, H-9b), 2.05 (m, H-6), 5.15 (tt, J=7.2, 1.4 Hz, H-10), 5.63 (dt, J=10.1, 1.5, H-1), 5.66 (dt, J=10.1, 1.9, H-2).

$^{13}$C NMR (126 MHz, $CD_2Cl_2$): 15.5 (C-14), 17.3 (C-12), 20.1 (C-5), 25.4 (C-13), 26.0 (C-9), 29.5 (C-15), 34.2 (C-8), 36.3 (C-7), 37.3 (C-4), 40.5 (C-6), 67.0 (C-3), 124.7 (C-10), 131.2 (C-11), 133.6 (C-2), 133.9 (C-1). NMR data are identical to those obtained for 20. HREIMS M+ 222.2009 (calcd for $C_{15}H_{26}O$, 222.1984).

The more polar fraction (100 mg, 3%) was identified as bisabolaadienol 25. $[\alpha]_D^{20}$=+53.40 (c 0.5, DCM). GC-MS (m/z, %): 222 (M+, 3), 207 (19), 204 (15), 189 (5), 161 (15), 148 (4), 137 (30), 119 (70), 109 (27), 93 (36), 69 (100), 55 (30), 43 (40), 41 (46).

$^1$H NMR (500 MHz, $CD_2Cl_2$): 0.89 (d, J=6.8 Hz, H-14), 1.19 (m, H-8a), 1.26 (s, H-15), 1.39 (m, H-8b), 1.43 (m, H-5a), 1.48 (m, H-7), 1.63 (s, H-12), 1.64 (m, H-4a), 1.71 (s, H-13), 1.72 (m, H-5b), 1.87 (d, J=12.4 Hz, H-4-b), 1.96 (m, H-9a), 2.05 (m, H-9b), 2.12 (m, H-6), 5.13 (t, J=7.2 Hz, H-10), 5.57 (ddd, J=10.1, 2.1, 1.1, H-1), 5.61 (ddd, J=10.1, 2.4, 1.6, H-2).

$^{13}$C NMR (126 MHz, $CD_2Cl_2$): 16.2 (C-14), 17.3 (C-12), 24.2 (C-5), 25.4 (C-13), 26.0 (C-9), 28.3 (C-15), 33.8 (C-8), 36.4 (C-7), 38.4 (C-4), 40.7 (C-6), 69.4 (C-3), 124.7 (C-10), 130.5 (C-1), 131.1 (C-11), 135.1 (C-2). NMR data are identical to those obtained for 21. HREIMS M+ 222.2006 (calculated for $C_{15}H_{26}O$, 222.1984).

Preparation of (3S,6S,7S)-1,10-bisaboladien-3-ol (26) and (3S,6R,7S)-1,10-bisaboladien-3-ol (27) (FIG. 11): Analogously to experiment described above, ketone 14 (1.483 g, 7.2 mmol) reacted with trimethylaluminum (7 ml of 2.0 M in heptane; 14.0 mmol) in the presence of [Rh(cod)$Cl_2$], 177 mg, 0.36 mmol) and (R)-BINAP (537 mg, 0.86 mmol) in dry THF (100 ml). Crude reaction products were purified by flash-chromatographed on $SiO_2$ with hexane:ethyl acetate, 5:1 to provide two fractions.

The less polar fraction was identified as compound 26 (503 mg, 31%). $[\alpha]_D^{20}$=+14.2 (c 1.1, DCM). GC-MS (m/z, %): 222 (M+, 5), 207 (16), 204 (17), 189 (8), 161 (17), 148 (11), 137 (23), 119 (75), 109 (31), 93 (47), 69 (100), 55 (28), 43 (34), 41 (49).

$^1$H NMR (500 MHz, $CD_2Cl_2$): 0.91 (d, J=6.8 Hz, H-14), 1.22 (m, H-8a), 1.26 (s, H-15), 1.40 (m, H-8b), 1.51 (m, H-5a), 1.52 (m, H-7), 1.55 (m, H-4a), 1.59 (m, H-5b), 1.63 (s, H-12), 1.71 (s, H-13), 1.82 (m, H-4-b), 1.96 (m, H-9a), 2.06 (m, H-9b), 2.03 (m, H-6), 5.14 (t, J=7.1 Hz, H-10), 5.67 (s, H-1), 5.67 (s, H-2).

$^{13}$C NMR (126 MHz, $CD_2Cl_2$): 16.2 (C-14), 17.3 (C-12), 22.1 (C-5), 25.4 (C-13), 26.0 (C-9), 29.5 (C-15), 36.6 (C-8), 36.3 (C-7), 37.5 (C-4), 41.1 (C-6), 67.1 (C-3), 124.7 (C-10), 131.1 (C-11), 132.7 (C-2/C-1), 133.9 (C-1/C-2). NMR data are identical to those obtained for 22. HREIMS M+ 222.2008 (calculated for $C_{15}H_{26}O$, 222.1984).

The more polar fraction (124 mg) was purified again with DCM: ethyl acetate, 30:1 to 10:1, to furnish compound 27 (88 mg, 6%). $[\alpha]_D^{20}$=−37.7 (c 2.0, DCM). GC-MS (m/z, %): 222 (M+, 4), 207 (23), 204 (21), 189 (6), 161 (21), 148 (5), 137 (32), 119 (86), 109 (31), 93 (53), 69 (100), 55 (30), 43 (37), 41 (51).

$^1$H NMR (500 MHz, $CD_2Cl_2$): 0.85 (d, J=6.9 Hz, H-14), 1.20 (m, H-8a), 1.26 (s, H-15), 1.40 (m, H-8b), 1.41 (m, H-5a), 1.53 (m, H-7), 1.63 (s, H-12), 1.64 (m, H-4a), 1.71 (s, H-13), 1.69 (m, H-5b), 1.87 (m, H-4-b), 1.97 (m, H-9a), 2.05 (m, H-9b), 2.14 (m, H-6), 5.14 (t, J=7.1 Hz, H-10), 5.53 (ddd, J=10.2, 2.2, 1.1, H-1), 5.61 (ddd, J=10.1, 2.4, 1.6, H-2).

$^{13}$C NMR (126 MHz, $CD_2Cl_2$): 15.4 (C-14), 17.3 (C-12), 22.3 (C-5), 25.4 (C-13), 25.9 (C-9), 28.2 (C-15), 34.2 (C-8), 36.3 (C-7), 38.3 (C-4), 40.2 (C-6), 69.4 (C-3), 124.7 (C-10), 130.5 (C-1), 131.1 (C-11), 134.8 (C-2). NMR data are identical to those obtained for 23. HREIMS M+ 222.2005 (calcd for $C_{15}H_{26}O$, 222.1984).

(3R,6S,7R,10S)-1-bisabolen-3,10,11-triol (28) (FIG. 12): A solution of alcohol 23 (150 mg, 0.68 mmol) in tert-butanol (3.2 ml) was added to a mixture of AD-mix-α (940 mg) and methanesulfonamide (62 mg) in water (3.2 ml) at 0° C. The mixture was stirred at 0° to 2° C. for 24 hours, then sodium sulfite (1 g) was added and the temperature was allowed to rise to 20° to 25° C. within 30 minutes. The mixture was extracted with methylene chloride (4×30 ml), the combined organic extracts were washed with 2N KOH, washed with brine and dried with $Na_2SO_4$. After evaporation of the solvent the residue was chromatographed on SiO$_2$ with ethyl acetate to yield triol 28 (121 mg, 70%). M.p. 125° C. (tert-butyl methyl ether). [α]$_D^{20}$=+16.7 (c 1.0, DCM). GC-MS (m/z, %): 238 (M$^+$–18), 3), 223 (4), 220 (3), 205 (7), 180 (10), 159 (14), 147 (16), 145 (15), 134 (67), 132 (85), 121 (80), 119 (52), 105 (37), 93 (72), 91 (50), 79 (33), 71 (54), 59 (100), 43 (92).

$^1$H NMR (500 MHz, CD$_2$Cl$_2$): 0.86 (d, J=6.8 Hz, H-14), 1.15 (s, H-12), 1.20 (m, H-8a), 1.21 (s, H-13), 1.23 (m, H-9a), 1.27 (s, H-15), 1.41 (m, H-5a), 1.55 (m, H-7), 1.56 (m, H-9b), 1.64 (m, H-4a), 1.68 (m, H-8b), 1.70 (m, H-5b), 1.87 (d, J=12.3 Hz, H-4-b), 2.17 (m, H-6), 3.32 (dd, J=9.8, 1.7 Hz, H-10), 5.53 (ddd, J=10.2, 2.3, 1.1, H-1), 5.62 (ddd, J=10.2, 2.5, 1.5, H-2).

$^{13}$C NMR (126 MHz, CD$_2$Cl$_2$): 15.6 (C-14), 22.1 (C-5), 23.0 (C-12), 26.3 (C-13), 28.2 (C-15), 29.7 (C-9), 31.3 (C-8), 36.9 (C-7), 38.2 (C-4), 39.9 (C-6), 69.4 (C-3), 72.9 (C-11), 79.0 (C-10), 131.7 (C-1), 134.9 (C-2). HRESIMS m/z 279.1932 (calculated for C$_{15}$H$_{28}$O$_3$Na, 279.1936).

X-ray analysis of triol 28: After re-crystallizing 28 from tert-butyl methyl ether a sample for X-ray analysis was prepared as follows: 2 mg of 28 was dissolved in 120 µl DCM, then 110 µl of hexane was added letting needle-like crystals to gradually precipitate.

All reflection intensities were measured at 110(2) K using a KM4/Xcalibur (detector: Sapphire3) with enhance graphite-monochromated Mo Kα radiation (λ=0.71073 Å) under the program CrysAlisPro (Version 1.171.35.11 Oxford Diffraction Ltd., 2011). The program CrysAlisPro (Version 1.171.35.11, Oxford Diffraction Ltd., 2011) was used to refine the cell dimensions. Data reduction was done using the program CrysAlisPro (Version 1.171.35.11, Oxford Diffraction Ltd., 2011). The structure was solved with the program SHELXS-97 (Sheldrick, 2008) and was refined on F$^2$ with SHELXL-97 (Sheldrick, G. M., Acta Cryst., A64, 112-122 (2008)). Analytical numeric absorption corrections based on a multifaceted crystal model were applied using CrysAlisPro (Version 1.171.35.11, Oxford Diffraction Ltd., 2011). The temperature of the data collection was controlled using the system Cryojet (manufactured by Oxford Instruments). The H atoms (except when specified) were placed at calculated positions using the instructions AFIX 13, AFIX 23, AFIX 43, or AFIX 137 with isotropic displacement parameters having values 1.2 or 1.5 times Ueq of the attached C atoms. The H atoms attached to O1, O2 and O3 were found from difference Fourier maps, and the O—H distances were restrained to be 0.84(3) Å using the DFIX instruction. The relative 3R,6S,7R,10R/3S,6R,7S,10S configuration was established (see FIG. 12, ORTEP drawing). The absolute configuration has not been found by anomalous dispersion effects in diffraction measurements on the crystal. The RSRS enantiomer has been assigned by reference to an unchanged chiral center at C-7 in the synthetic procedure and also by chemical correlations.

Figure 13:
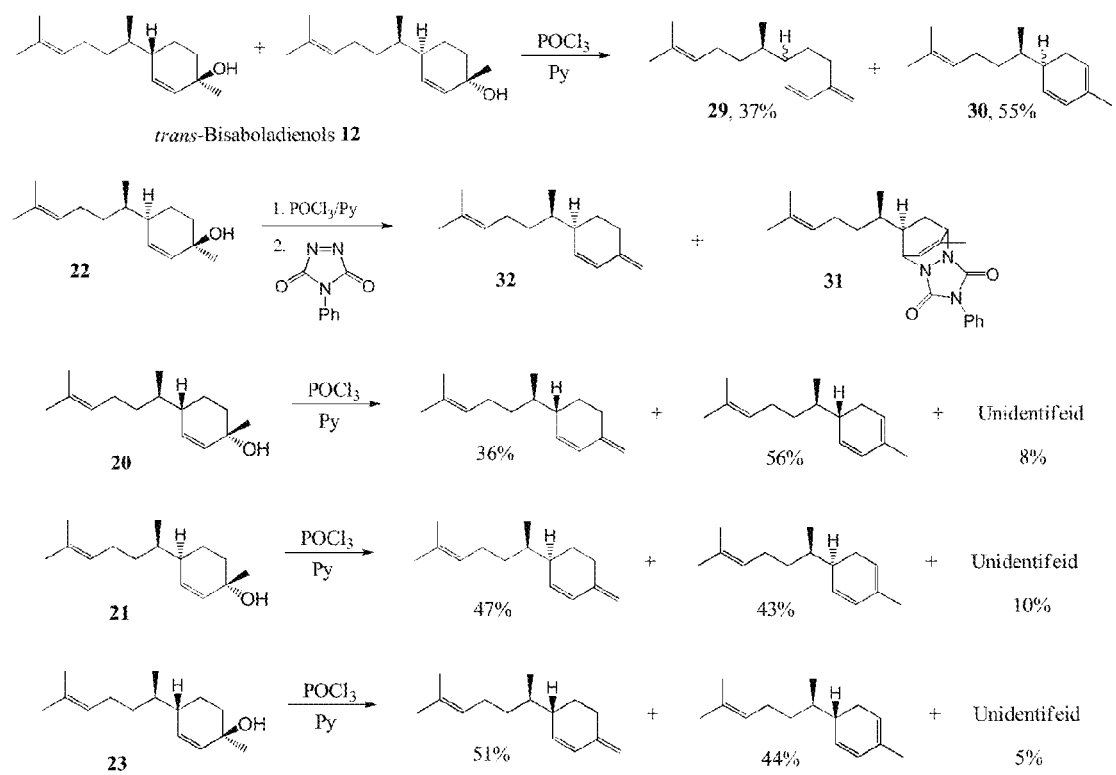
FIG. 13 shows dehydrations of selected (7R)-bisaboladi-enols to β-sesquiphellandrene and zingiberene diastereomers as described below.
Figure 14:
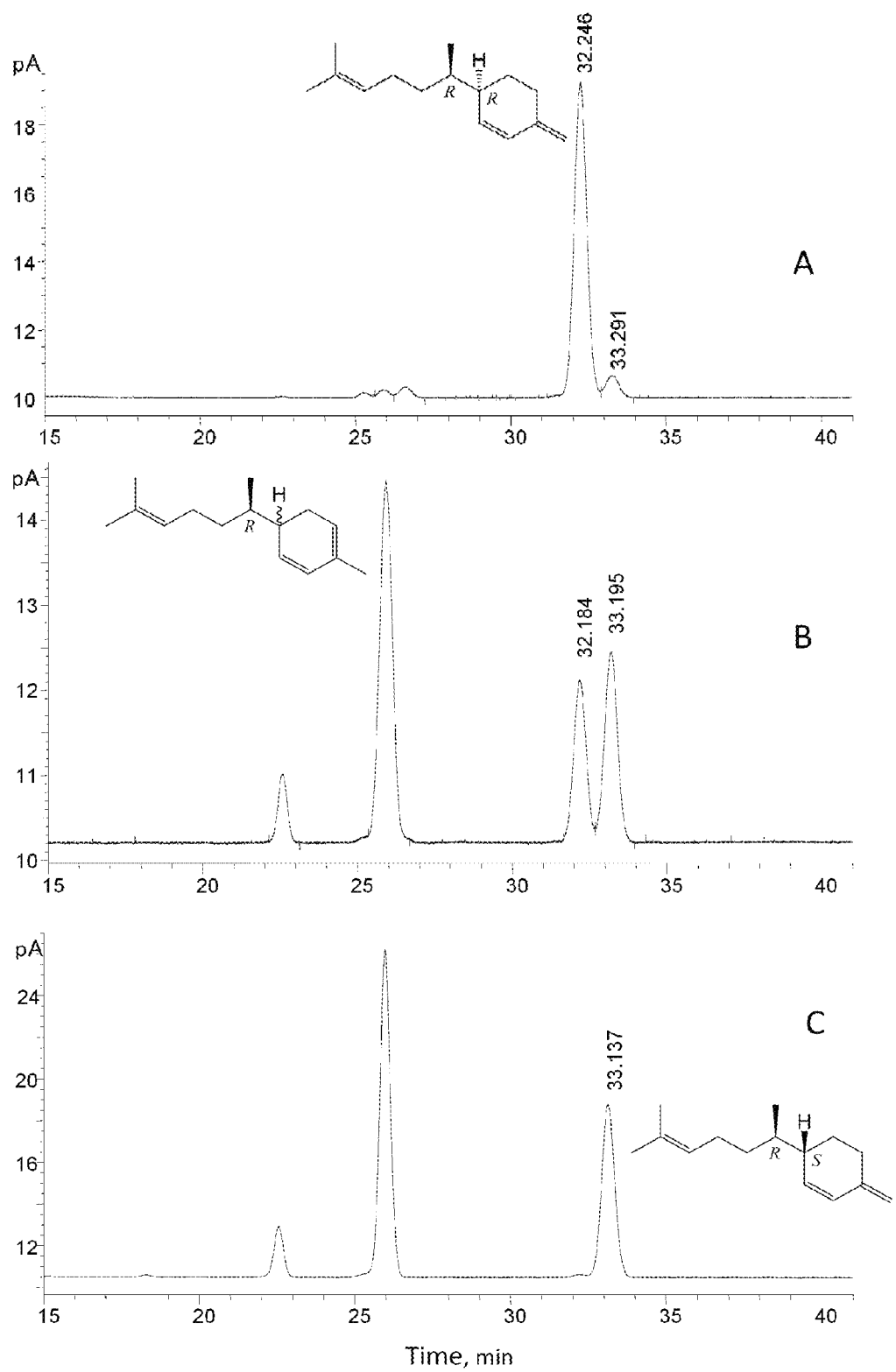
FIG. 14 shows GC-FID analyses of (7R)-bisabolatrienes (formed by dehydrations of cis-bisaboladienols) on HYDRODEX-β-6TBDM as described below. Part A: (6R,7R)-β-sesquiphellandrene (32) from alcohol 22 after removal of zingiberene and other byproducts (see Material and Methods below); Part B: dehydration products from 12; Part C: dehydration products from alcohol 20.
Figure 15:
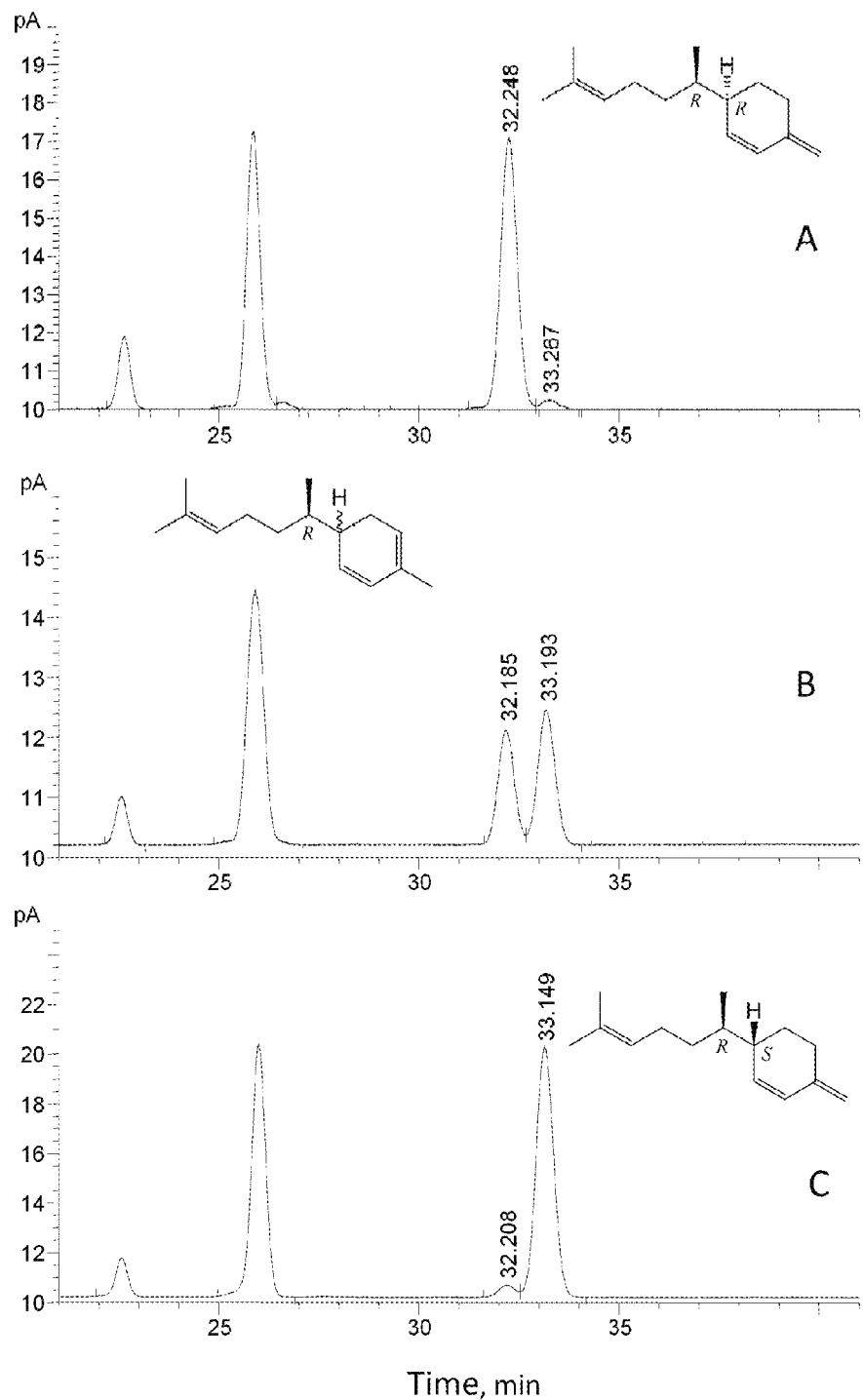
FIG. 15 shows GC-FID analyses of (7R)-bisabolatrienes (formed by dehydrations of trans-bisaboladienols) on HYDRODEX-β-6TBDM as described below. Part A: dehydration products from alcohol 21; Part B: dehydration products from 12; Part C: dehydration products from alcohol 23.

Dehydrations of 1,10-bisaboladien-3-ols (FIGS. 13 and 16): (a) A solution of trans-1,10-bisaboladien-3-ols 12 (70 mg, 0.32 mmol) in dry pyridine (3 ml) was cooled to 0° C. and treated with POCl$_3$ (58 ul, 0.58 mmol). The mixture was warmed to room temperature, stirred for 18 hours, then poured into ice-water (5 ml) and extracted with hexane (4×5 ml). The combined hexane extracts were washed with 1M HCL, washed with brine, and dried with Na$_2$SO$_4$. After evaporation of the solvent, the residue was chromatograhyed with hexane to provide a mixture of hydrocarbons (55 mg) consisting of 5% unknown sesquiterpene, 43% 1,3(15), 10-bisabolatriene 29, and 52% 1,3,10-bisabolatriene 30. The last two compounds had GC retention times on HP-5MS column and mass-spectra identical with those of authentic samples of β-sesquiphellandrene and zingiberene. GC-FID analysis of the mixture was also conducted on HYDRODEX-6TBDM column (FIG. 14, part B).

(b) Alcohol 22 (222 mg, 2 mmol) was treated with POCl$_3$ (193 ul, 1.93 mmol) in dry pyridine (3 ml) at 0° C., then the mixture was stirred 2 hours at room temperature. After the work-up described above, the products were extracted with dichloromethane and purified by chromatography with hexane to provide a mixture of hydrocarbons (53 mg) consisting of 56% 1,3,10-bisabolatriene, 31% 1,3(15),10-bisabolatriene, and 13% of unidentified sesquiterpene. This was taken into dry THF (2.5 ml) and 4-phenyl-1,2,4-triazoline-3,5-dione (31 mg) was added at room temperature. After 30 minutes, the mixture was concentrated with a gentle stream of N$_2$ and chromatographed with pentane: methyl acetate, 99:1. (6R,7R)-(−)-1,3(15),10-Bisabolatriene (diastereomer of β-sesquiphellandrene 32, 9 mg) of 97% of chemical purity (by GC-MS) was isolated in the first fraction. [α]$_D^{20}$=54.17 (c 0.58, CHCl$_3$). Lit. (Kreiser, W., and F. Korner, Helvetica Chimica Acta., 82: 1427-1433 (1999)) for (6S,7S)-β-sesquiphellandrene [α]$_D$=+39.58 (c 0.43, CHCl$_3$). GC-MS (m/z, %): 204 (30, M$^+$), 161 (40), 133 (40), 120 (36), 119 (15), 109 (25), 105 (21), 93 (64), 92 (36), 91 (55), 79 (21), 77 (38), 69 (100), 55 (22), 41 (47). $^1$H NMR (600 MHz, CDCl$_3$): 0.87 (d, J=6.5 Hz, 3H), 1.14-1.22 (m, 1H), 1.36-1.46 (m, 2H), 1.47-1.53 (m, 1H), 1.59 (s, 3H), 1.68 (br.s, 3H), 1.69-1.75 (m, 1H), 1.89-1.95 (m, 1H), 1.99-2.05 (m, 1H), 2.16-2.23 (m, 1H), 2.25-2.32 (m, 1H), 2.42 (dt, J=12.0, 6.0 Hz, 1H), 4.72 (br.s, 1H), 4.74 (br.s, 1H), 5.09 (br.t, J=7.0 Hz, 1H), 5.70 (br.d, J=11.0 Hz, 1H), 6.15 (dm, J=11.0 Hz, 1H).

$^{13}$C NMR (151 MHz, CDCl$_3$): 16.46, 17.68, 25.73, 26.06, 26.26, 30.50, 33.90, 36.51, 41.02, 109.94, 124.80, 129.79, 131.29, 134.02, 143.80. Mass spectral and NMR data were in good agreement with those reported for (6S,7S)-β-sesquiphellandrene (Kreiser and Korner, 1999). A Diels-Alder adduct of zingiberene with 4-phenyl-1,2,4-triazoline-3,5-dione (42 mg) was also isolated in the second fraction.

(c) In separate experiments, alcohols 20, 21, 23, 24, and 25 (4 mg each) in pyridine (50 µl) were treated with POCl$_3$ (4 µl) and hydrocarbon mixtures were separated as described in experiment (a) above. The mixtures were analyzed by GC-MS on HP-5MS and by GC-FID on HYDRODEX-6TBDM columns. Results are presented in FIGS. 13-18.

Figure 19:
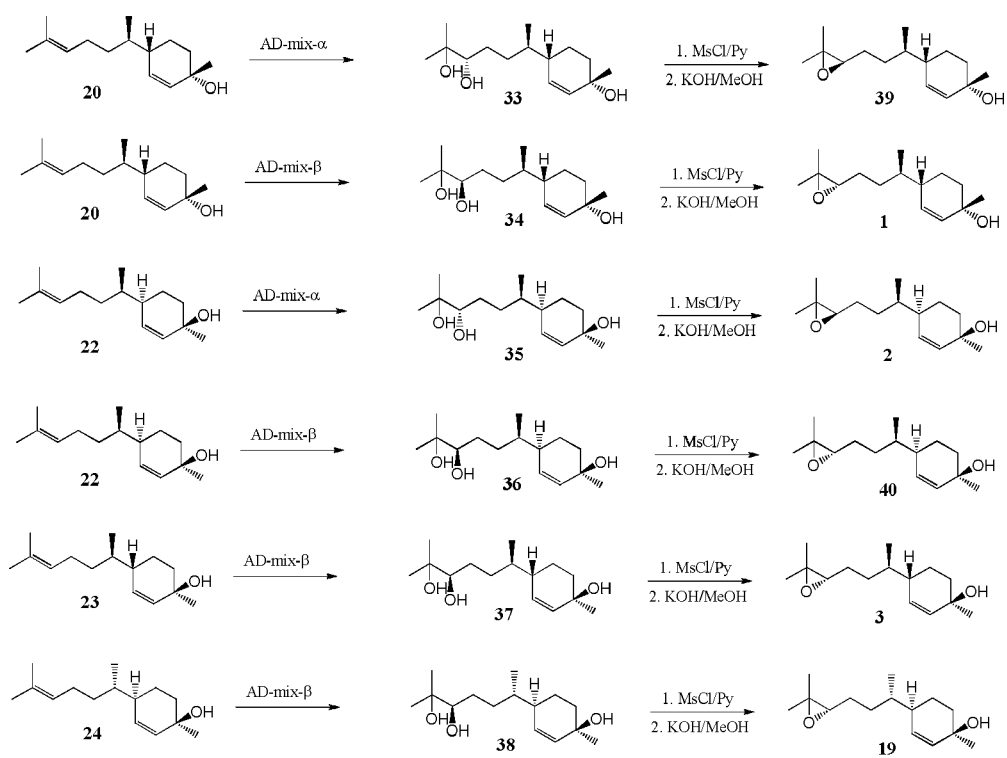
FIG. 19 shows syntheses of individual triols and epoxybisabolenols including *H. halys* suspected pheromone components 1 and 3 as described below.

Enantioselective dihydroxylations of 1,10-bisaboladien-3-ols 20, 22, 23, and 24 (FIG. 19): Solutions of alcohols (1 mmol) in tert-butanol (4.7 ml) were added to a mixture of AD-mix-α or AD-mix-β (1.38 g), depending on stereoisomer being synthesized (FIG. 19), and methanesulfonamide (91 mg) in water (4.7 ml) at 0° C. Mixtures were stirred at 0-2° C. for 24 hours, then treated with sodium sulfite (1.47 g) and the triols 33, 34, 35, 36, 37, and 38 were isolated as described in preparation of 28 and characterized in Table 12. $^1$H and $^{13}$C NMR spectra of triols are presented in Tables 13 and 14, respectively.

10,11-epoxy-1-bisabolen-3-ols 1, 2, 3, 19, 39, and 40 (FIG. 19): Methanesulfonyl chloride (77 µl, 1.14 mmol) was added to a stirred solution of a triol (1.0 mmol) in dry pyridine (1.5 ml) at 0° to 5° C., then the mixture was allowed to warm to room temperature and stirred for 1 hour. The reaction mixture was poured into ice-water (4 ml) and extracted with CH$_2$Cl$_2$ (3×10 ml). Combined organic extracts were washed with ice-water, dried (with Na$_2$SO$_4$) and concentrated to yield a crude mesylate. This was taken in methanol (5 ml), cooled to 0° C. and treated with a solution of KOH (112 mg, 2 mmol) in MeOH (1.3 ml), which resulted in an instantaneous precipitation of inorganic salts. The reaction mixture was warmed to room temperature, stirred for 30 minutes and concentrated to remove most of the MeOH. The residue was taken into NH$_4$Cl solution (pH 7-8) and extracted with ether (3×10 ml). Combined organic extracts were washed with ice-water, washed with brine, then dried with $Na_2SO_4$ and concentrated. Flash chromatography (hexane/ethyl acetate, 3:2) yielded epoxybisabolenols (Table 12). $^1H$ and $^{13}C$ NMR spectra of epoxybisabolenols are presented in Tables 13 and 14, respectively.

(6R,7S,10S)-10,11-epoxy-1,3-bisaboladiene (Zigiberene epoxide, 41), (FIG. 20): Zingiberene (isolated from ginger oil, 103 mg, 0.5 mmol) was dihydroxylated with AD-Mix-β (700 mg) in the presence of methanesulfonamide (46 mg) in the mixture of tert-butanol (2.4 ml) and water (2.4 ml) as described above to provide a diol (25 mg, 0.11 mmol). The diol was converted to a mesylate with methanesulfonyl chloride (10 µl, 0.12 mmol) in pyridine (130 µl), and the crude mesylate was treated with a solution of KOH (12 mg) in MeOH (630 µl) to provide oxide 41 (11 mg) containing 8% curcumene epoxide after chromatography.

Mixture of epoxides 4, 5, and 6 (FIG. 20): A solution of cis-alcohols 16 (888 mg, 4 mmol) and dry pyridine (1.956 ml, 24 mmol) in anhydrous methylene chloride (25 ml) was treated with $POCl_3$ (724 µl, 7.2 mmol) at 0° C. The mixture was slowly warmed to room temperature, stirred for 5 hours, then poured into ice-water and extracted with methylene chloride (3×15 ml). The combined organic extracts were washed with water, washed with a sodium bicarbonate solution, washed with brine, and then dried with sodium sulfate. After evaporation of the solvent, the remainder was flash chromatographed with hexane to give a mixture of hydrocarbons 42 (256 mg, ~1.25 mmol). This was epoxidized with MCPBA (240 mg of 80-85%-pure, 1.39 mmol) in the presence of sodium acetate (115 mg, 1.39 mmol) in a $CH_2Cl_2$ solution (8 ml) at 0° C. for 3 hours. After the work-up described above and flash chromatography with hexane/ethyl acetate, 30:1, a mixture of epoxides 43 (47 mg) was isolated. It consisted of 82% 4, 2% 5, and 13% 6.

Mixture of epoxides 44 (FIG. 11): Alcohol 26 (75 mg, 0.34 mmol) was epoxidized with MCPBA (81 mg) in the presence sodium acetate (30 mg, 0.37 mmol) in DCM (5 ml) at 0° to 5° C. for 3 hours to yield after regular work-up and flash chromatography epoxide 44 as a mixture of 10S and 10R diastereomers. Mass-spectrum of 44 matched that of 17.

Field Bioassays. Field Trials of Experimental Pheromone Constituents: Pyramid traps based on dimensions previously used for native stink bugs (Leskey and Hogmire 2005, Hogmire and Leskey 2006) and for brown marmorated stink bugs (Leskey et al. 2012c) were used for all trials. Panels were constructed from Sintra® (partially extruded PVC) sheets (Laird Plastics, Pittsburgh, Pa.) or plywood, and painted with flat black latex exterior paint based on previous results indicating that adult and nymphal BMSB responded in greater numbers to this particular visual stimulus compared with other visual stimuli (Leskey et al. 2012c). Each panel was 1.22 m high, 52 cm wide at the base, and 7 cm wide at the top. Collection jars were constructed based on previously published dimensions (Hogmire and Leskey 2006) with internal cone opening of 1.6 cm with trimmed wire edging to reduce escape. In addition, a Hercon Vaportape™ II (Hercon Environmental, Emigsville, Pa.) was added as a killing agent to prevent escape from traps. In a preliminary study, addition of a killing agent increased trap captures ~250%. Traps were deployed ~5 meters from the border of apple and pear orchards at the Appalachian Fruit Research Station or in the border area between wood lots and row crops in Kearneysville, W. Va., Shepherdstown, W. Va., Keedysville, Md., and Beltsville, Md. Traps were spaced ~50 meters apart. Traps were baited with compounds identified from headspace collections of male BMSB, synthesized and formulated into gray rubber septa or left unbaited. Treatments evaluated are listed in Table 2.

Fourteen trials were conducted between 19 Apr. to 20 Oct. 2011 (Table 3) and four trials between 20 Mar. to 10 Oct. 2012 (Table 4). Traps were checked a minimum of twice weekly and the treatments were re-randomized at each collection.

All adults and nymphs were removed from traps and recorded. Hercon Vaportape™ strips were changed at four week intervals and lures were changed at two week intervals. Comparisons of adult and nymphal captures used the SAS GLM procedure to evaluate effect of treatment and replicate followed by Tukey's HSD if the model was significant. Appropriate transformations were used to stabilize normality if needed. The effect of sex was dropped from all models because it was never a significant factor.

Purity Trial of #10: Trials were conducted mid-May to early June 2012 in Kearneysville, W. Va., and 8 May to 5 Jun. 2012 in Beltsville, Md., to determine if #10 required purification to ensure optimal attractiveness to BMSB adults and nymphs. Black pyramid traps were baited with septa formulated with #10 (highly purified), #20 (crude), and #21 (semipurified) material. Loading of active ingredients was identical for each lure. Traps were checked and collected twice-weekly as described previously, and the treatments were re-randomized at each collection.

Dose-Dependent Responsiveness to #10: We conducted a dose response trial using #10 formulated into rubber septa. Black pyramid traps were baited with single rubber septa containing 0.1, 1.0, or 10 mg rubber septa containing #10, or ten 10 mg rubber septa (100 mg equivalent) or left unbaited (control). Traps were checked and collected twice-weekly and the treatments were re-randomized at each collection. Trials were conducted in three locations (Shepherdstown, W. Va., Keedysville, Md., and Beltsville, Md.) to establish if BMSB exhibit a dose-dependent response. Trials were conducted from 14 Jun. to 19 Jul. 2012.

Synergy trials for attraction of BMSB to #10 and methyl (2E,4E,6Z)-decatrieonate (MDT): From 6 Apr. to 23 Oct. 2012 in BARC North Farm (4 replicates) in Beltsville, Md., and from 16 May to 23 Oct. 2012 in a commercial tree fruit orchard in Arden, W. Va. (3 replicates), we tested the following four treatments for attraction of BMSB adults and nymphs, using a full-sized black pyramid trap adapted for BMSB (see above): (1) #10 lure (Table 4) replaced every 2 weeks; (2) #3 lure, MDT, (Sterling International, Spokane, Wash.; ~119 mg loading; see text below), replaced every 4 weeks; (3) #14 lure, in which #10 and MDT lures hung together in trap, replaced as above for each lure; and (4) no lure (control).

The MDT lure obtained from Sterling International was extracted with pentane which yielded 420 mg of crude product. According to TLC analysis on silica using dichloromethane, the extracted material contained MTD (Rf 0.46) plus unknown chemical(s) with Rf 0.20. This material was flash chromatographed on silica with hexane:dichloromethane, 1:1, to obtain 119 mg of pure MDT. The identity of MDT was re-confirmed by comparison of the gas chromatographic retention time and mass-spectrum with those of a standard prepared according to Khrimian (Khrimian, A., Tetrahedron, 61: 3651-3657 (2005)).

Traps were checked and collected twice-weekly in Beltsville, and weekly in Arden, as described previously, and the treatments were re-randomized at each collection. Field trapping results were summed by approximately two-week intervals, and the totals for each replicate analyzed by ANOVA and additionally with Tukey's HSD multiple comparisons at α=0.05 if the overall 1-way ANOVA F-test was significant at α=0.05. In addition, a two-way ANOVA with interaction was tested to determine if the combined lure provoked a different level of attractiveness (a significant interaction) than would be expected from a combination of the attractiveness of each separate lure type. Such an interaction, with numbers exceeding the expected attraction for the combined lure, represents a true synergy of the two lures.

Figure 2:
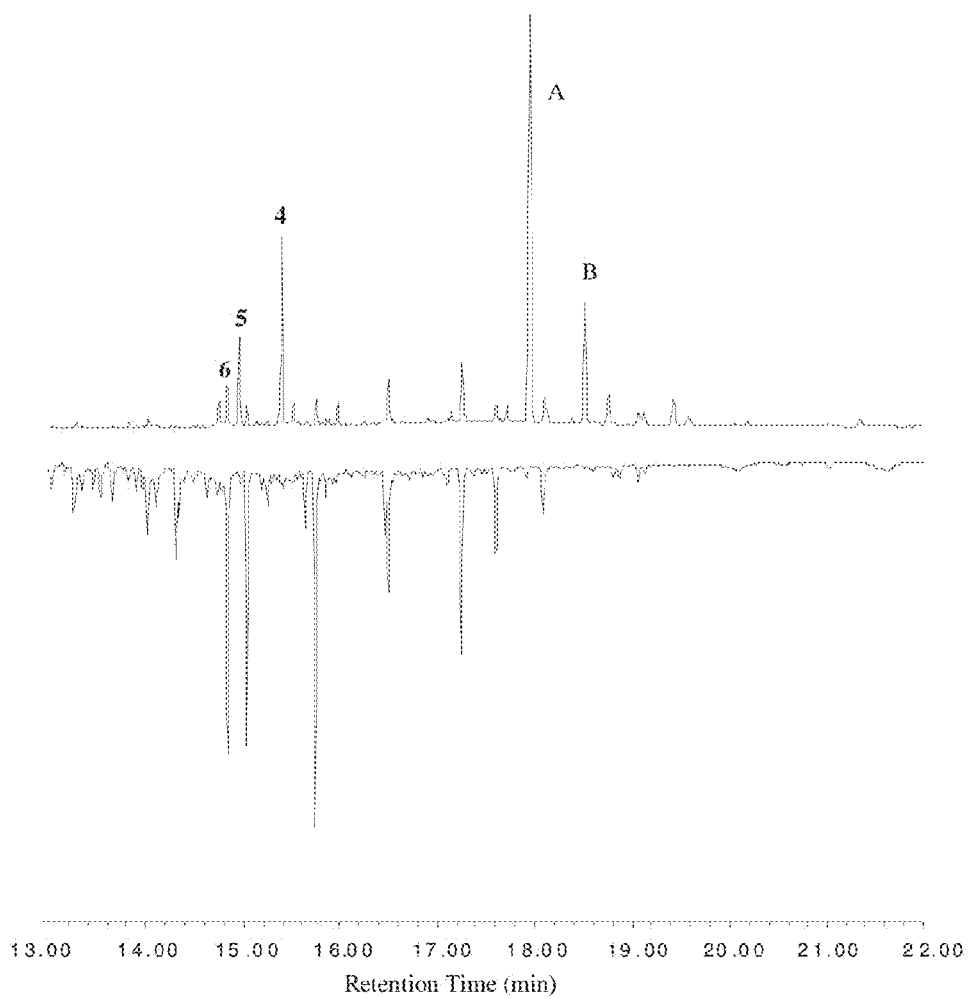
FIG. 2 shows GC/MS (gas chromatography coupled with mass spectrometry) total ion traces of aeration extracts from virgin male *H. halys* (top) versus female (bottom) on a DB-5MS column as described below. The aerations were conducted on October 19 for 24 hours (13 days old adults, 3 bugs of each sex). Five male-specific compounds are indicated: cis-10,11-epoxy-1-bisabolen-3-ol (A), trans-10,11-epoxy-1-bisabolen-3-ol (B), 10,11-epoxy-1,3(15)-bisabola-diene, (4) 10,11-epoxy-1,3-bisaboladiene (5) and 10,11-epoxy-1,3,5-bisabolatriene (6).
Figure 3:
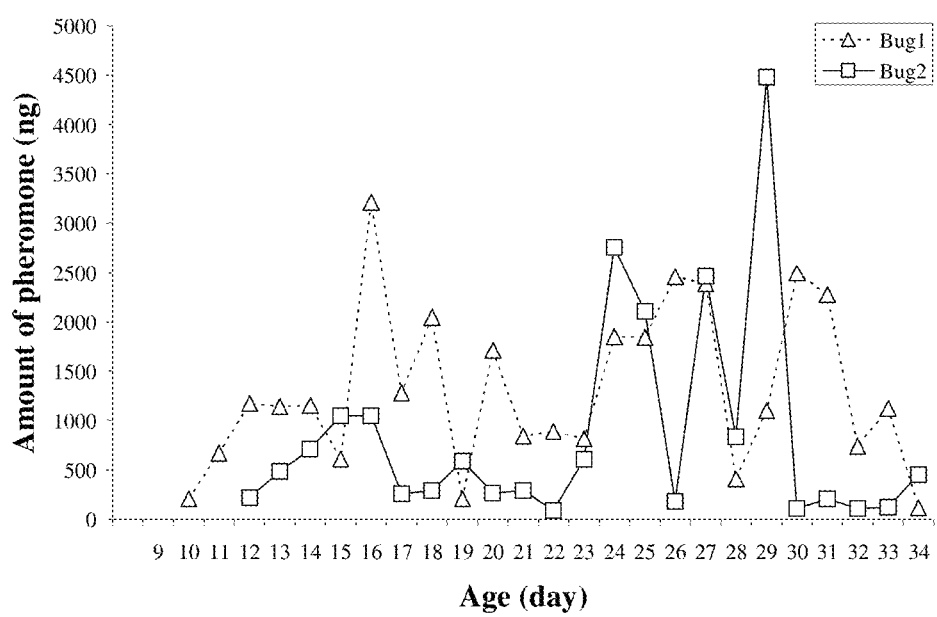
FIG. 3 shows male-specific semiochemical production from two individual virgin male *H. halys* during a 35 days period as described below. The aerations were conducted from 11 Feb. to 17 Mar. 2011 starting with 1 day old male adults. The male-specific compounds were not be detected from males younger than ~10 days.
Figure 4:
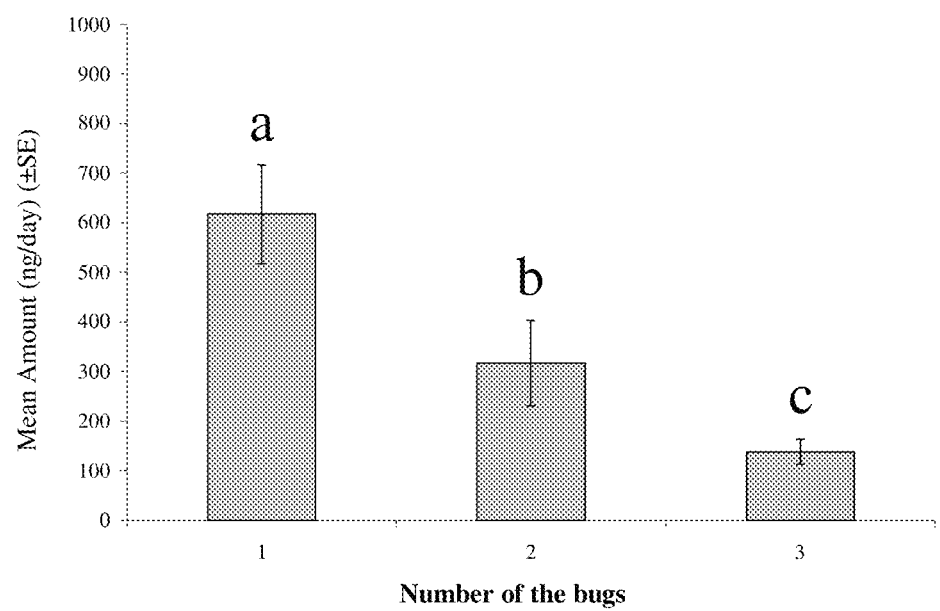
FIG. 4 shows male-specific semiochemical production from virgin male *H. halys* by different group sizes as described below. The aerations were conducted from 17 Jan. to 31 Jan. 2011 using 12 to 26 days old male adults during a 14 days period (square root transformed, N=14, df=2.39, F=13.61, P<0.05).

Results. Identification and Synthesis: The GC/MS total ion traces of airborne extracts demonstrated that male *H. halys* consistently produced at least five specific compounds (A, B, 4-6) that were not in the female's airborne extracts (FIG. 2). These male-specific compounds could not be detected from males younger than around 10 days (FIG. 3). In addition, quantitative analysis of male-specific compounds indicated that the number of the male bugs in the collection affected the amount they produced; in other words, the more bugs then the less male-specific compounds could be obtained per bug (FIG. 4). Interestingly, no semiochemicals could be detected from the airborne extracts if the number of male bugs was, for example, from seven to nine. However, a single male could produce a significant amount of semiochemical if it was separated from that group. Cold on-column injections were performed on the GC and GC/MS, and the same male-specific compounds were detected, indicating that the minor components were not the result of decomposition or isomerization of the major component in the GC and/or GC/MS injection inlets.

Figure 5:
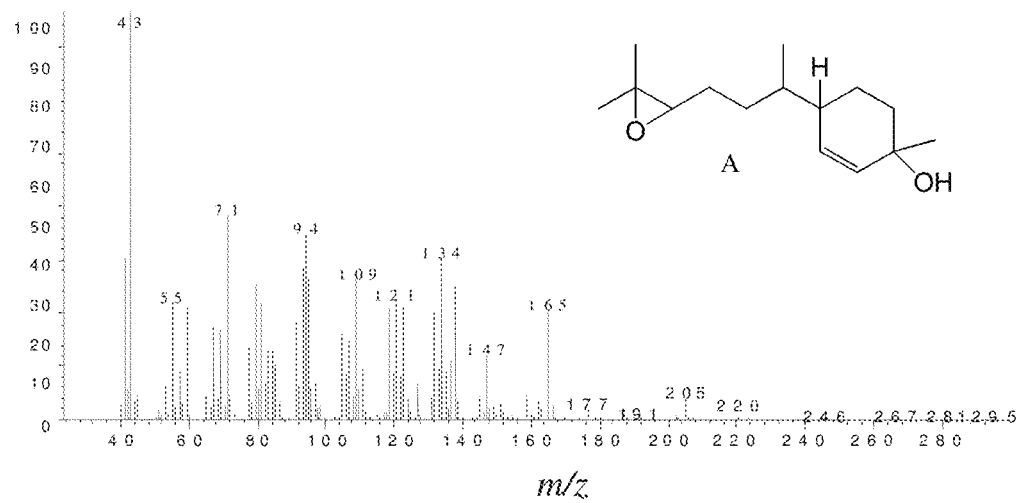
FIG. 5 shows EI (electron impact) mass spectra of natural semiochemicals from *H. halys* and the corresponding chemical structures (as described below): cis-10,11-epoxy-1-bisabolen-3-ol (A), trans-10,11-epoxy-1-bisabolen-3-ol (B), 10,11-epoxy-1,3(15)-bisaboladiene, (4) 10,11-epoxy-1,3-bisaboladiene (5), and 10,11-epoxy-1,3,5-bisabolatriene (6).
Figure 5:
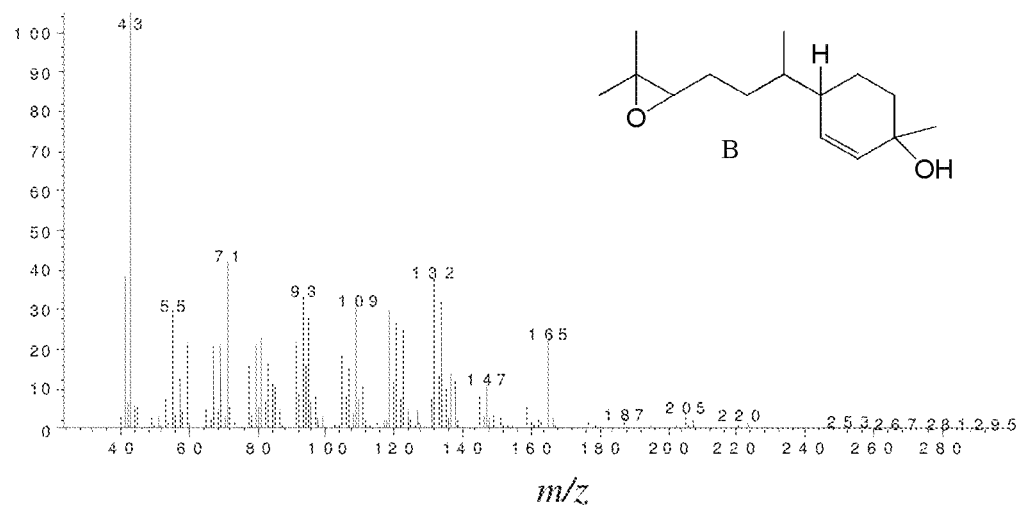
Figure 5:
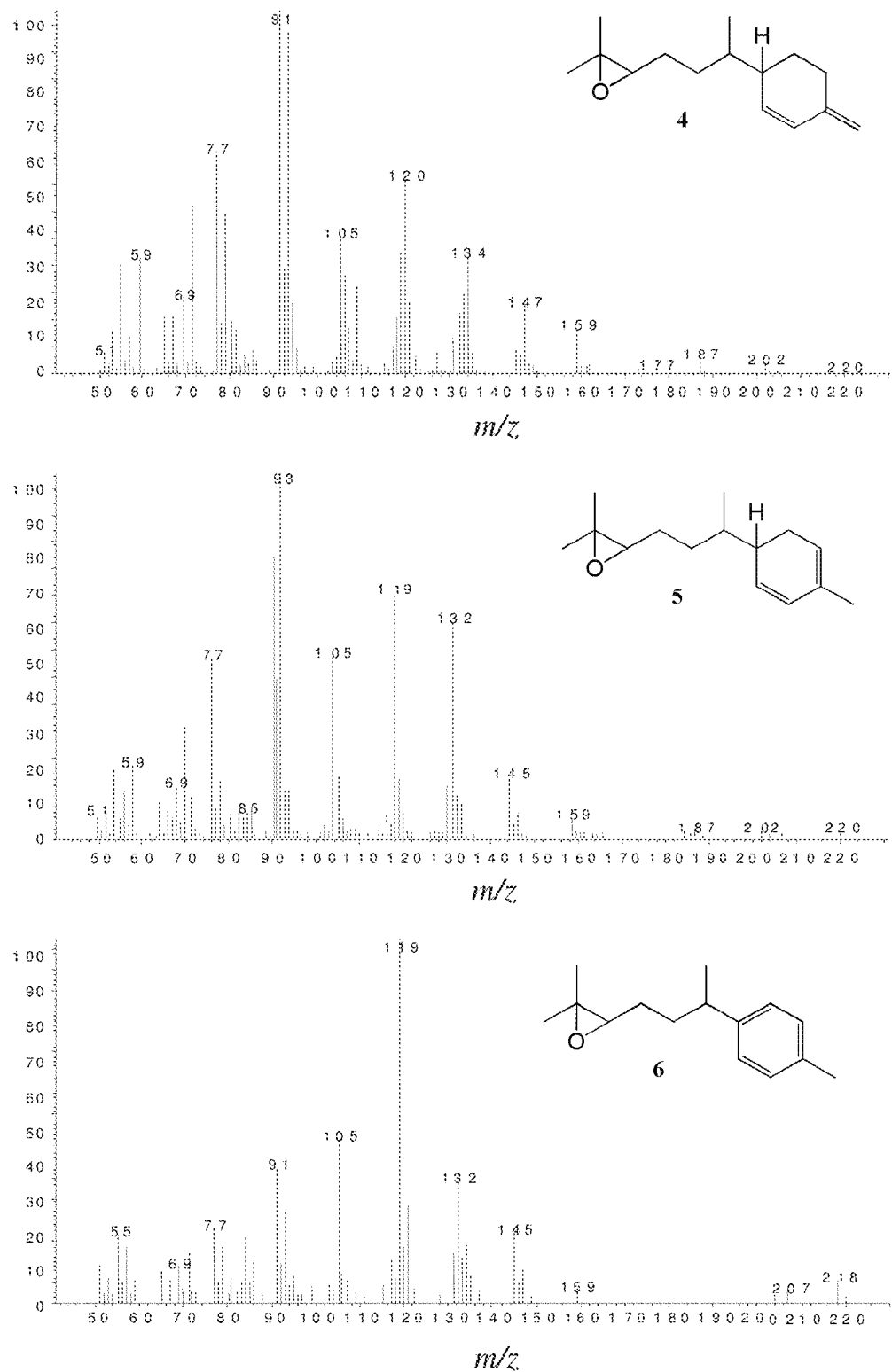

The EI mass spectra of male-specific semiochemicals are shown in FIG. 5. The spectra were similar to certain published sesquiterpenoids but no close match could be obtained from GC/MS NIST/Wiley mass spectral database libraries; in other words, libraries would not reveal the structure.

However, we found striking similarities between mass spectra of compounds A and B with that of recently published (Zahn et al., 2008; Zahn, D., et al., Journal of Chemical Ecology 38:126 (2012)) aggregation pheromone of harlequin bug, *Murgantia histrionica*, dubbed murgantiol but not characterized stereochemically. Having synthesized both murgantiol and its stereoisomer, we identified by retention times and mass-spectra compound A as murgantiol and compound B as its stereoisomer. Synthetic A and B used in these identifications were mixtures of four stereoisomers each, not separated on HP-5MS column. The relative and absolute configurations of murgantiol remained undetermined and there were no published syntheses of single stereoisomers of epoxybisabolenol. Thus in order to determine which stereoisomer(s) of epoxybisabolenol (of total sixteen possible) are produced by BMSB and whether or not identified compounds bear any biological significance, we had to develop stereo- and enantioselective syntheses. At the same time, we planned to bioassay stereoisomeric mixtures A and B, both developed from (S)- and (R)-citronellal, to determine whether these mixtures were attractive for BMSB.

The ions at m/z 220 present in mass spectra of compounds 4 and 5 (FIG. 5) were apparently molecular ions, corresponding to a molecular formula $C_{15}H_{24}O$, and ion at m/z 202 suggested that a water molecule (18 amu) was lost from molecules during fragmentations. This assumption was confirmed by CI mass spectra (Table 1) by the ions at m/z 221 (M+1) and m/z 238 (M+18) when ammonia ($NH_3$) was used as a reagent gas. In addition, the corresponding m/z 222 (M+2) and m/z 242 (M+22) ions were obtained with deuterated ammonia ($ND_3$), indicating that neither compound contained exchangeable protons. The confirmation of m/z 218 as a molecular ion for compounds 6 failed due to insufficient amount of natural material and low sensitivity of CI mass spectra. However, the structure of 6, 4 and 5 were confirmed by synthesis (see below).

Figure 6:
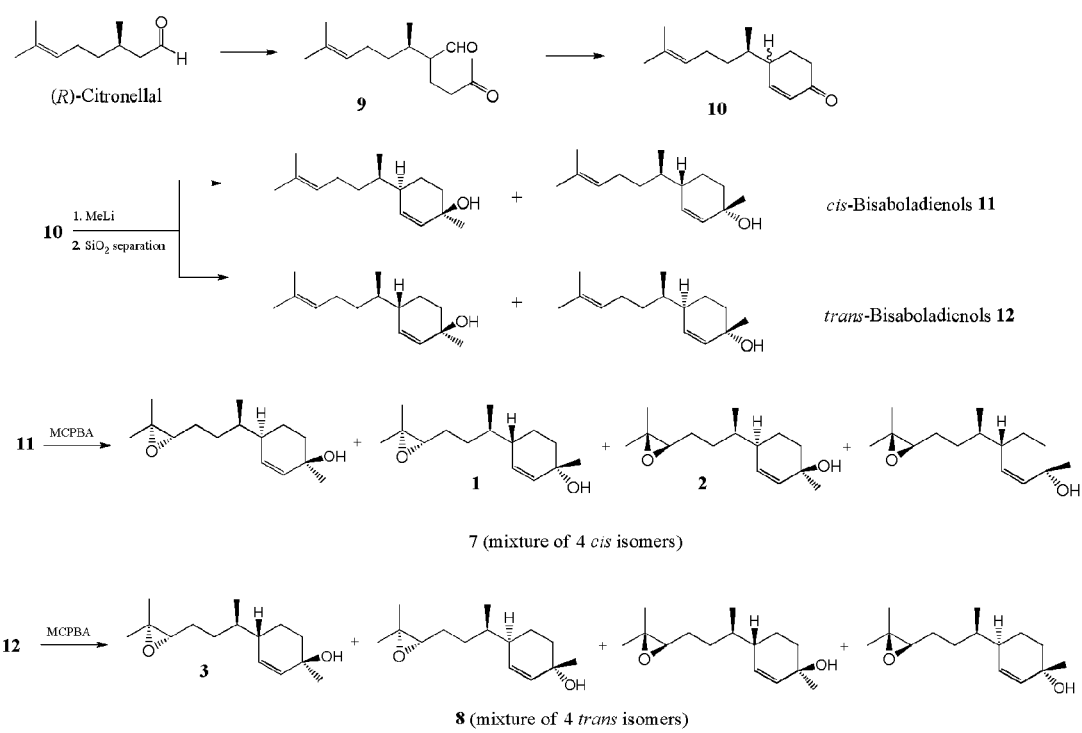
FIG. 6 shows a non-stereoselective syntheses of four-component mixtures of cis and trans-epoxybisabolenols 7 and 8 from (R)-citronellal as described below.

Syntheses of stereoisomeric mixtures of epoxybisabolenols: FIG. 6 shows a non-stereoselective route that we used to make epoxybisabolenol mixtures, essentially following Zahn et al., 2008, with some modifications. (R)-Citronellal was converted in two steps to a diastereomeric mixture of cyclohexenones 10, which then reacted with methyl lithium to yield two fractions after column chromatography of the resulting alcohols on $SiO_2$. The first (least polar) fraction we identified as a mixture of two cis-bisaboladienols 11, and the second (more polar) fraction as trans-bisaboladienols 12. The assignment of relative (trans and cis) configurations was done by comparison of the order of elution of these fractions from $SiO_2$ column with the one of monoterpene analogs (Mori, K., Tetrahedron: Asymmetry, 17: 2133-2142 (2006)). More precisely, relative configurations were determined by X-ray analysis of a crystalline 3R,6S,7R,10S triol (see below). Epoxydations of bisaboladienols 11 and 12 with m-chloroperbenzoic acid (MCPBA) produced cis- and trans-epoxybisabolenols 7 and 8 respectively, each as a mixture of four stereoisomers. Mixtures 7 and 8 were tested in the field separately and also as a 3:1 mixture. To simplify the synthesis, a 3:1 mixture of 7 and 8 was developed without isolation of pure 11 and 12 (see Material and Methods). Moreover, a crude mixture containing 7 and 8 in a 1:2 ratio and also 1,2,10,11-diepoxybisabolan-3-ol by-products (they were not found in the aerations of bugs) was developed by combining the two chemical processes and circumventing column chromatography. These mixtures were tested in the field against BMSB alongside with 3:1 mixture of 7 and 8. Synthesis of epoxybisabolenols 17 and 18 from (S)-citronellal was conducted in an analogous manner and is depicted in FIG. 7.

Figure 8:
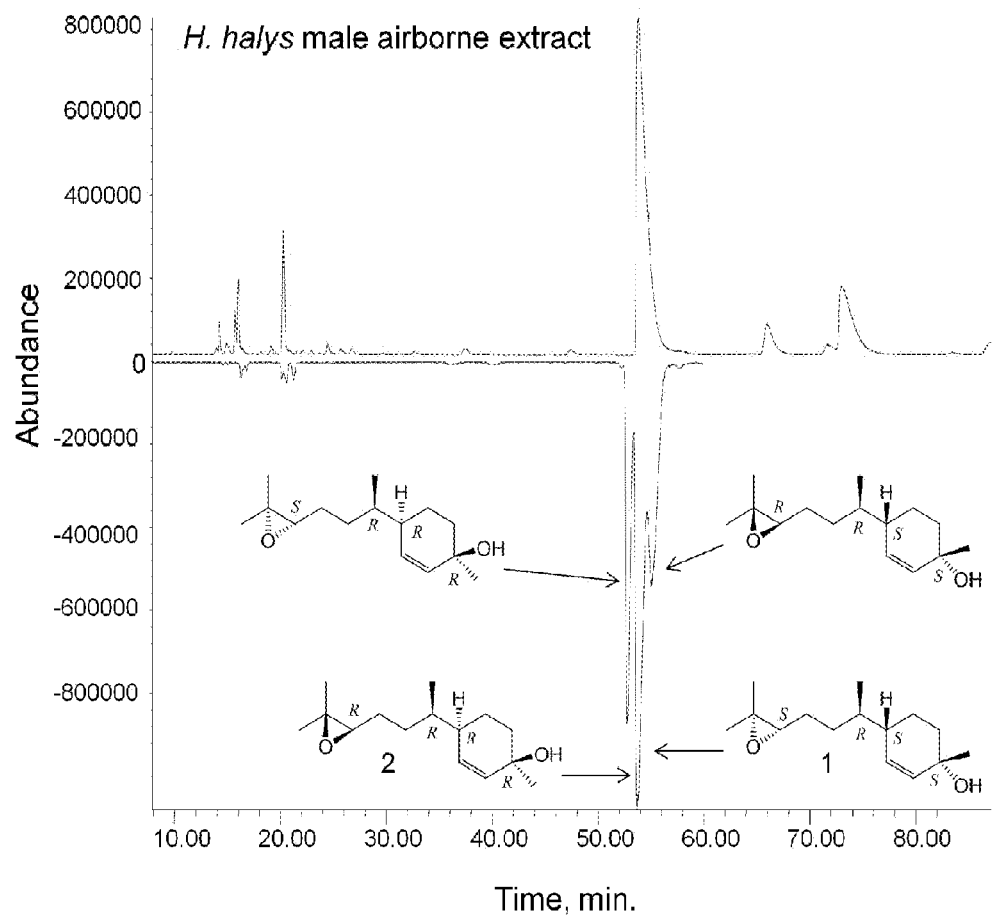
FIG. 8 shows total ion chromatograms of GC-MS analysis of *H. halys* male airborne extract (top) and four-component mixture of cis-10,11-epoxy-1-bisabolen-3-ols 7 (bottom) on HYDRODEX-β-6TBDM column as described below.

Chiral GC analyses of epoxybisabolenol mixtures vs. natural BMSB male collection: To narrow down the number of stereoisomers for identification of BMBS male-specific compounds, we conducted GC analyses of stereoisomeric mixtures and the male airborne extract from BMSB on several chiral GC columns. FIG. 8 demonstrates total ion chromatograms of *H. halys* male collection (upper trace) and the mixture 7 on a HYDRODEX-β-6TBDM column. As the lower trace showed, the column did not provide a complete separation of all four stereoisomers present in 7, with the middle peak (represented by two compounds) matching the main male-specific compound by the retention time and mass-spectrum. Having synthesized most of the stereoisomers of epoxybisabolenol, we later identified the two compounds of interest as (3S,6S,7R,10S)-10,11-epoxy-1-bisabolen-3-ol (1) and (3R,6R,7R,10R)-10,11-epoxy-1-bisabolen-3-ol (2).

Figure 10:
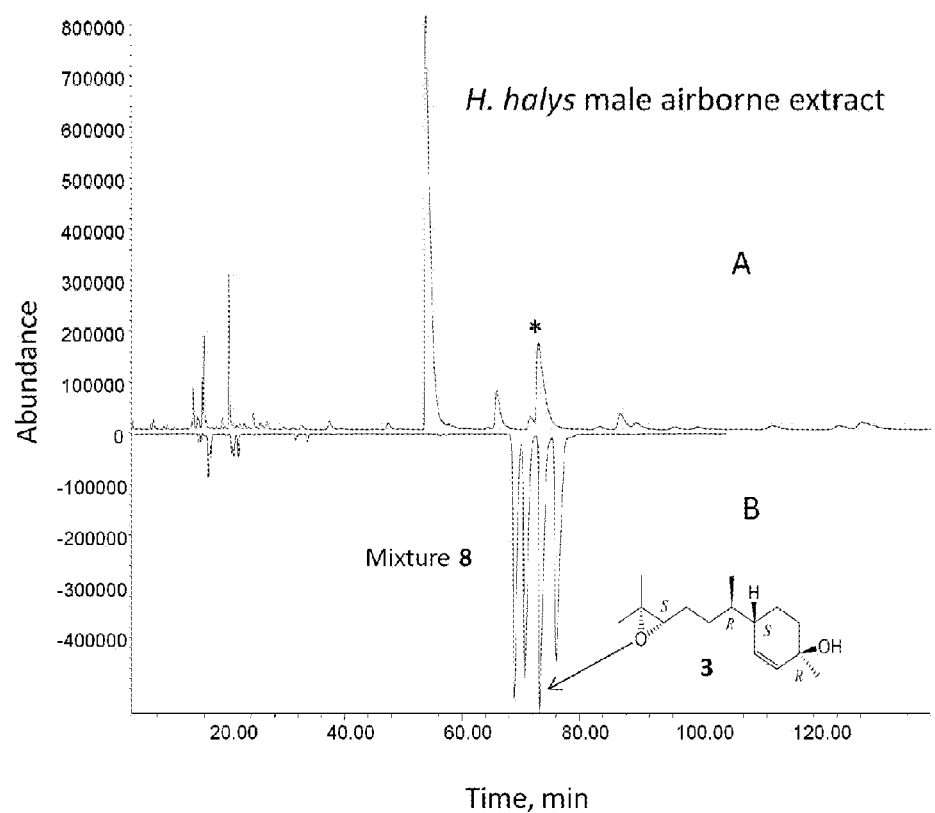
FIG. 10 shows GC-FID analyses on HYDRODEX-β-6TBDM as described below. Part A: *H. halys* male airborne extract; Part B: Four-component trans-epoxybisabolenols 8.

Next we discovered that four cis stereoisomers originated from (S)-citronellal (17) were well separated on a chiral HYDRODEX-β-6TBDM GC column (FIG. 9, Part A), and peak #2 of that mixture matched the main male-specific compound present in the *H. halys* airborne extract (FIG. 9, Parts B and C). This stereoisomer co-eluted with (3R,6R,7S,10S)-10, 11-epoxy-1-bisabolen-3-ol (19; FIG. 7). Finally, we found that four trans stereoisomers based on (R)-citronellal were almost baseline separated on HYDRODEX-β-6TBDM (FIG. 10, part B) and peak #3 of that mixture matched the second most abundant male-specific compound from *H. halys*. This stereoisomer was identified as (3R,6S,7R,10S)-10,11-epoxy-1-bisabolen-3-ol (3). Thus, in a pursuit of male-specific compounds that could constitute an aggregation pheromone, we concentrated on four single stereoisomers: 1, 2, 3, and 19.

Figure 11:
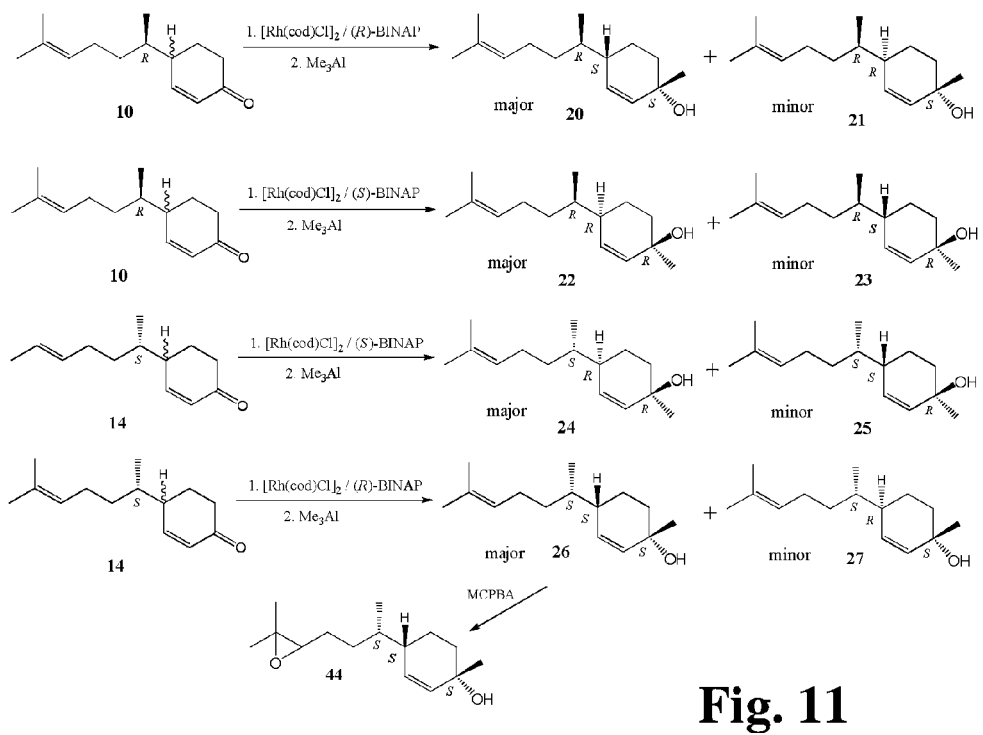
FIG. 11 shows synthesis of bisaboladienols 20-27 using enantioselective Rh-catalyzed addition of $Me_3Al$ to enones 10 and 14 and synthesis of epoxide mixture 44 from 26 as described below.

Asymmetric syntheses of selected epoxybisabolenols. Rhodium-catalyzed diastereoselective addition of trimethylaluminum to enones 10 and 14: We used a rhodium-catalyzed asymmetric 1,2-addition of aluminum organyl compounds to enones (Siewert, J., et al., Angew. Chem. Int. Ed., 46: 7122-7124 (2007)) to synthesize bisaboladienols intermediates (FIG. 11). We found that the reaction of cyclohexenone 10, which was a mixture of two diastereoisomers in about 1:1 ratio, with trimethylaluminum in the presence of chloro(1,5-cyclooctadiene)rhodium(I)dimer and (R)-BINAP yielded two individual stereoisomers, as judged from their $^{13}$C NMR spectra each composed of fifteen signals. The reaction was sluggish compared to the one with cyclohex-2-enone (Siewert et al., 2007) and required 2 eq. of trimethylaluminum and much longer reaction time to complete (24 hours vs. 30 minutes in the literature). The major stereoisomer formed had higher Rf on TLC but lower retention time in GC analysis as compared to the minor stereoisomer. Based on X-ray crystallography analysis and chemical correlations (section see below), the major and minor stereoisomers were assigned structures 20 and 21, respectively (FIG. 11). By substituting the chiral ligand with its enantiomer, (S)-BINAP, we obtained two other stereoisomers from cyclohexenone 10, with the major reaction product assigned structure 22 and the minor structure 23. Changing the chirality at C-7 did not alter the reaction course, as cyclohexenone 14 (also ~1:1 mixture of diastereomers) provided four more stereoisomers (FIG. 11). Reaction of 14 with trimethylaluminum in the presence of chloro(1,5-cyclooctadiene)rhodium(I)dimer and (S)-BINAP gave a major diastereoisomer 24 and a minor 25. Analogous reaction in the presence of (R)-BINAP yielded diastereomers 26 and 27.

Assignment of relative (cis/trans) configurations: 1,10-Bisaboladien-3-ols can exist in two relative configurations: cis if the hydroxy group at C-3 and the alkyl group at C-6 are on the same side, and trans if these groups are on the opposite sides of a plane formed by C-6, C-1, C-2, and C-3. The assignment of relative configurations of 1,10-bisaboladien-3-ols has been largely missing from the literature except for Terhune et al. (Terhune, S. J., et al., Canadian Journal of Chemistry, 53: 3287-3293 (1974)) who used IR but their depiction of trans was incorrect. As we mentioned above, the relative and absolute configurations of murgantiol (Zahn et al., 2008) remained undetermined despite successful $^1$H and $^{13}$C NMR recordings including 1H-1H COSY, HMBS, HSQC and NOESY correlations. Two male-produced sex pheromones identified from rice stalk stink bug, *Tibraca limbativentris*, also bear 1,10-bisaboladien-3-ol structural motif but neither relative nor absolute configurations of these compounds were determined (Borges, M., et al., J. Chem. Ecol., 32: 2749-2764 (2006)). Terhune et al. (2008) isolated several new compounds from the plant *Zingiber officinale*, among them a 1,10-bisaboladoien-3-ol, dubbed zingiberenol. The latter was assigned a trans-configuration based on similarities of its IR spectrum with that of trans-p-menth-2-en-1-ol, but the structure was presented incorrectly (see http://www-.pherobase.com/database/floral-compounds/floral-taxa-compounds-detail-cis-2-menthenol.php for correct structure of trans-p-menth-2-en-1-ol). Because the original source of IR spectra presented only names and not structures (Mitzner, B. M., et al., Applied Spectroscopy, 22: 34-53 (1968)), and the ambiguity of cis/trans definitions in 3,6-disubstituted cyclohexenes, IR data were deemed unreliable in the assignment of relative configurations of 1,10-bisaboladien-3-ols.

When analyzing differences between individual stereoisomers and mixtures of p-menth-2-en-1-ol (Mori, 2006), we noticed that cis-isomers eluted faster during the chromatography on $SiO_2$ using hexane/ethyl acetate than corresponding trans-isomers. Thus cis-p-menth-2-en-1-ols had higher retention factors (Rf)) than trans-p-menth-2-en-1-ol. We hypothesized that 1,10-bisaboladoien-3-ols, as sesquiterpene analogs of p-menth-2-en-1-ols, would have the same behavior on $SiO_2$: cis alcohols would have higher Rfs than trans alcohols. Regardless of absolute configuration at C-7, all eight stereoisomers of 1,10-bisaboladien-3-ols could be divided into two groups, cis and trans, with four compounds in each. There are significant differences across groups but almost no differences within members of each group. Four stereoisomers shown in mixtures 11 and 15 (FIGS. 6 and 7) had retention factors that were higher than those of four other stereoisomers presented in 12 and 16. In addition, GC retention times of stereoisomers in 11 and 15 were lower than those of stereoisomers in 12 and 16. Thus assigning a relative configuration on a single stereoisomer would suffice to assign relative configurations of all eight stereoisomers of 1,10-bisaboladien-3-ols.

Figure 12:
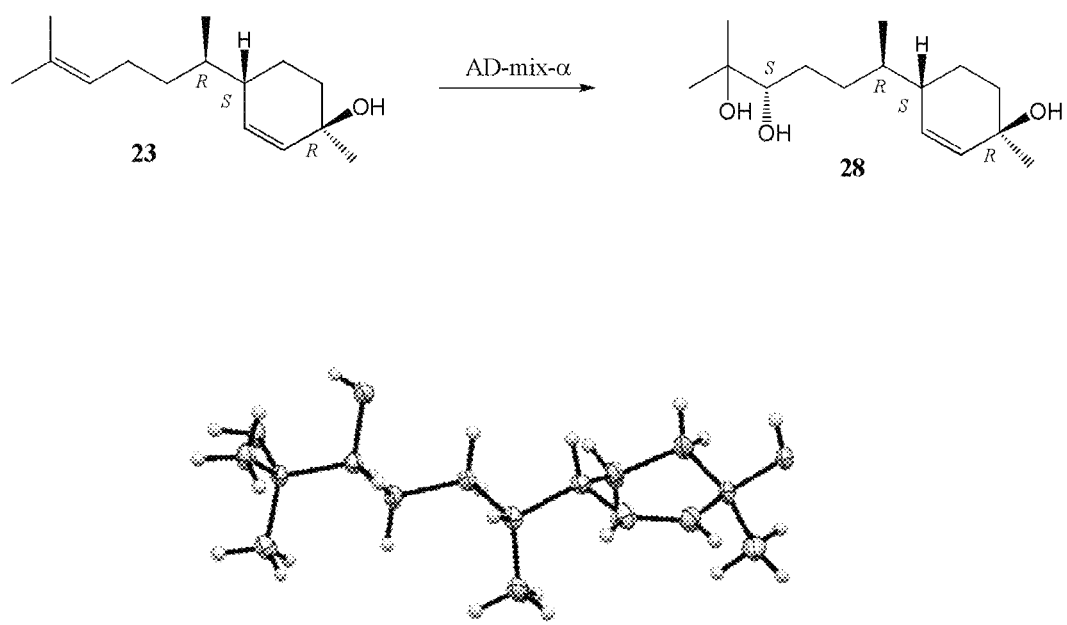
FIG. 12 shows synthesis and X-ray ORTEP (Oak Ridge thermal ellipsoid plot) drawing of 3R,6S,7R,10S triol 28 as described below.

We found that the Sharpless asymmetric dihydroxylation (Sharpless et al., 1992) of stereoisomer 23 with AD-mix-α proceeded smoothly and provided a crystalline triol 28 (FIG. 12). After crystallization of 28 using liquid-liquid diffusion technique (see Material and Methods) we obtained crystals that were studied by X-ray using Mo Kα radiation. The ORTEP drawing of crystalline 28 presented in FIG. 12 clearly shows relative 3R*,6S*,7R*,10R* configuration, which means that hydroxy group at C-3 and alkyl group at C-6 are in trans position. This provided direct evidence that a lower Rf, higher RT stereoisomer 23 had trans relative configuration and this rule should apply to other compounds presented in mixtures 12 and 16. Conversely, higher Rf, lower RT stereoisomers comprising mixtures 11 and 15 must have cis configurations. Thus only X-ray gave an unambiguous answer regarding what is trans and what is cis.

The 3R,6S,7R,10S absolute configuration was assigned to 28 by reference to an unchanged chiral center at C-7 in the synthetic procedures and also by chemical correlations (see below).

Absolute configurations of 1,10-bisaboladien-3-ols: Absolute configurations of compounds presented in FIG. 11 were established based on the knowledge of their relative configurations and chemical correlations. We used the dehydration reaction of bisaboladienols with phosphorus(V)oxychloride ($POCl_3$; Bhonsle, J. B., et al., Indian Journal of Chemistry, 33B: 313-316 (1994)) to correlate them with β-sesquiphellandrene and zingiberene of established absolute configurations. The reaction of mixture 12 with $POCl_3$ provided expected 1,3(15),10-bisabolatriene 29 and 1,3,10-bisabolatriene 30 (both as mixtures of two diastereomers) plus an unknown sesquiterpene hydrocarbon in a 43:52:5 ratio (FIG. 13). Two major compounds were identified by GC-MS with authentic samples as zingiberene (Millar, J. G., Journal of Natural Products, 61: 1025-1026 (1998)) and β-sesquiphellandrene (McBrien, H. L., et al., J. Chem. Ecol., 28: 1797-1817 (2002)). Diastereomeric sesquiphellandrenes and zingiberenes were not separated on HP-5MS column but sesquiphellandrenes were almost baseline separated on HYDRODEX-6TBDM column (FIG. 14, part B). Because β-sesquiphellandrenes derived from 12 had 7R configuration, and the natural (−)-β-sesquiphellandrenes had 6R,7S configuration (Kreiser and Korner, 1999), the latter could not be used for the identification of these GC peaks. Hence, we have made a concerted effort to isolate an individual 1,3(15),10-bisabolatriene from a dehydration reaction. Stereoisomer 22 was dehydrated with $POCl_3$ analogously to 12 and a mixture of hydrocarbons formed (FIG. 13; see also Material and Methods) was subjected to the reaction with 4-phenyl-1,2,4-triazoline-3,5-dione, whereupon zingiberene acted as a dienolphile to form a Diels-Alder adduct 31 (Millar, 1998). Compound 32, which did not undergo a Diels-Alder reaction (Millar, 1998), was isolated by chromatography in a surprisingly pure (97%) form, considering the presence in the original hydrocarbon mixture of 13% of unidentified sesquiterpene that apparently also reacted with 4-phenyl-1,2,4-triazoline-3,5-dione. $^1$H and $^{13}$C NMR spectra of 32 were in good agreement with those of (6S,7S)-β-sesquiphellandrene but 32 was dextrorotatory and, hence, was assigned 6R,7R configuration that was also attributed to 22 from which 32 was originated. And, because alcohol 22 belonged to the pool of higher Rf, lower retention time cis-1,10-bisaboladienols, it was assigned 3R,6R,7R absolute configuration.

With the absolute configuration of compound 32 established, we assigned the faster-eluting peak on GC-MS (FIG. 14, part B) 6R,7R configuration and slower-eluting diastereomer 6S,7R configuration. Thus, for the determination of absolute configurations of three other alcohols with 7R configuration (FIG. 11) we used the GC method. Reaction of alcohol 20 with POCl$_3$ produced a mixture of sesquiterpene hydrocarbons, GC trace of which on HYDRODEX-6TBDM column is presented on FIG. 14, part C. It is evident that β-sesquiphellandrene present in that mixture matched the slower-eluting peak and, hence, has 6S,7R configuration. Because alcohol 20 has cis relative configuration (higher Rf, lower RT), its absolute configuration had to be 3S,6S,7R. Dehydrations of two trans (lower Rf, higher RT) alcohols 21 and 23 produced mixtures of hydrocarbons (FIG. 13), GC of which are shown on FIG. 15, part A and part C, correspondingly. Because 21 produced primarily (6R,7R)—O-sesquiphellandrene and 23 yielded (6S,7R)-β-sesquiphellandrene, they were assigned 3S,6R,7R and 3R,6S,7R configurations, respectively.

Figure 16:
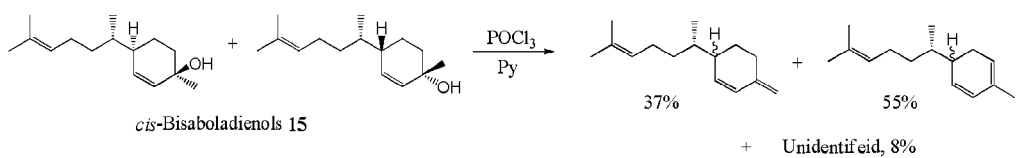
FIG. 16 shows dehydrations of selected (7S)-bisaboladi-enols to β-sesquiphellandrene and zingiberene diastereomers as described below.
Figure 16:
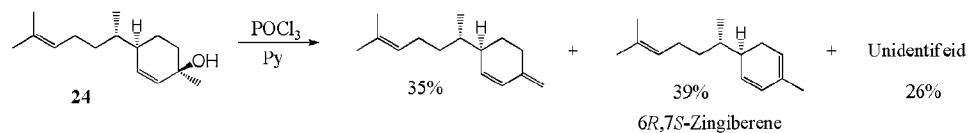
Figure 16:
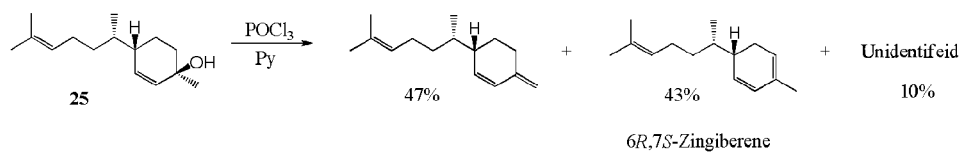
Figure 17:
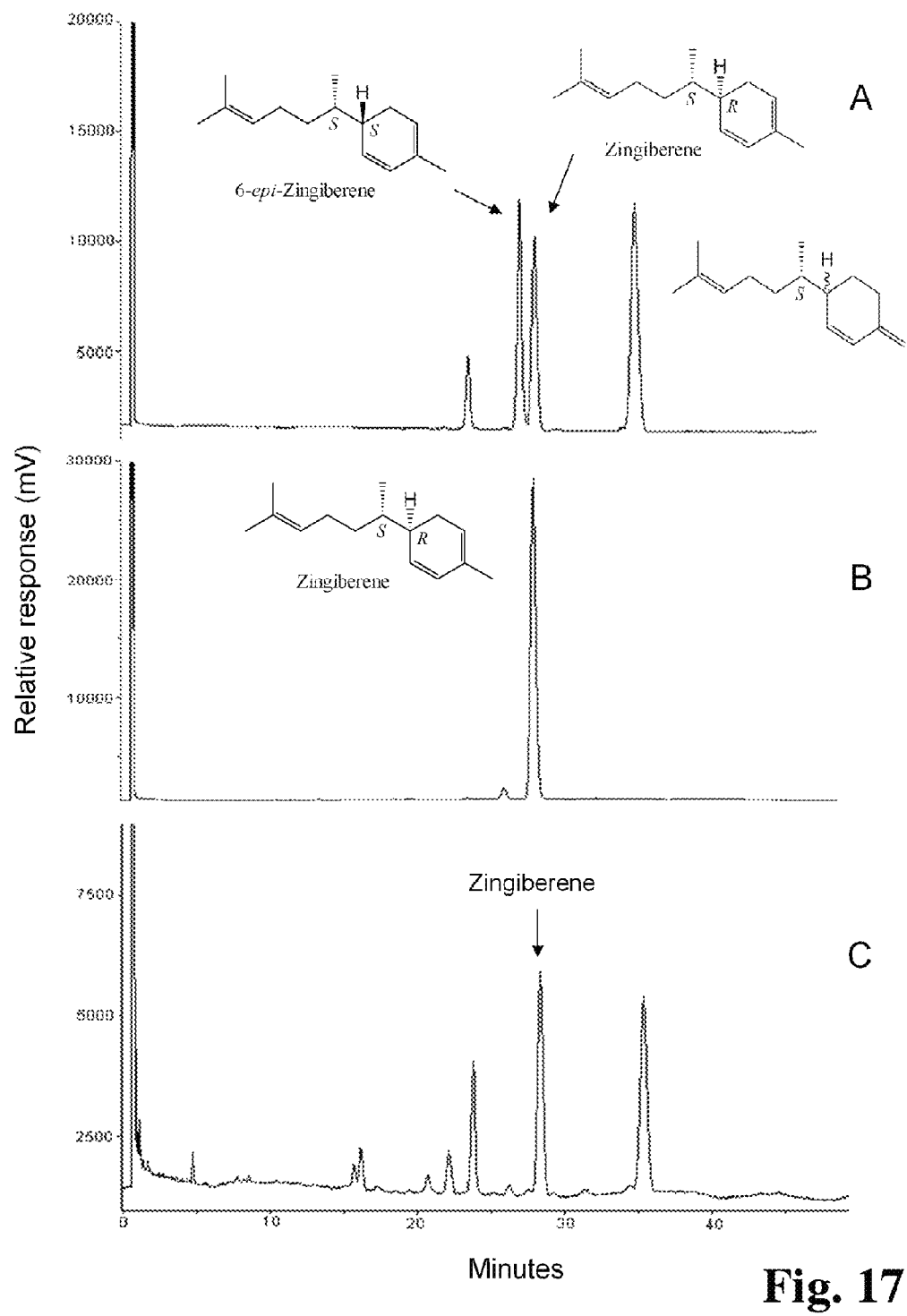
FIG. 17 shows GC-FID analyses of (7S)-bisabolatrienes on HYDRODEX-β-6TBDM as described below. Part A: dehydration products from mixture 15; Part B: Natural (−)-(6R, 7S)-zingiberene; Part C: dehydration products from alcohol 24.
Figure 18:
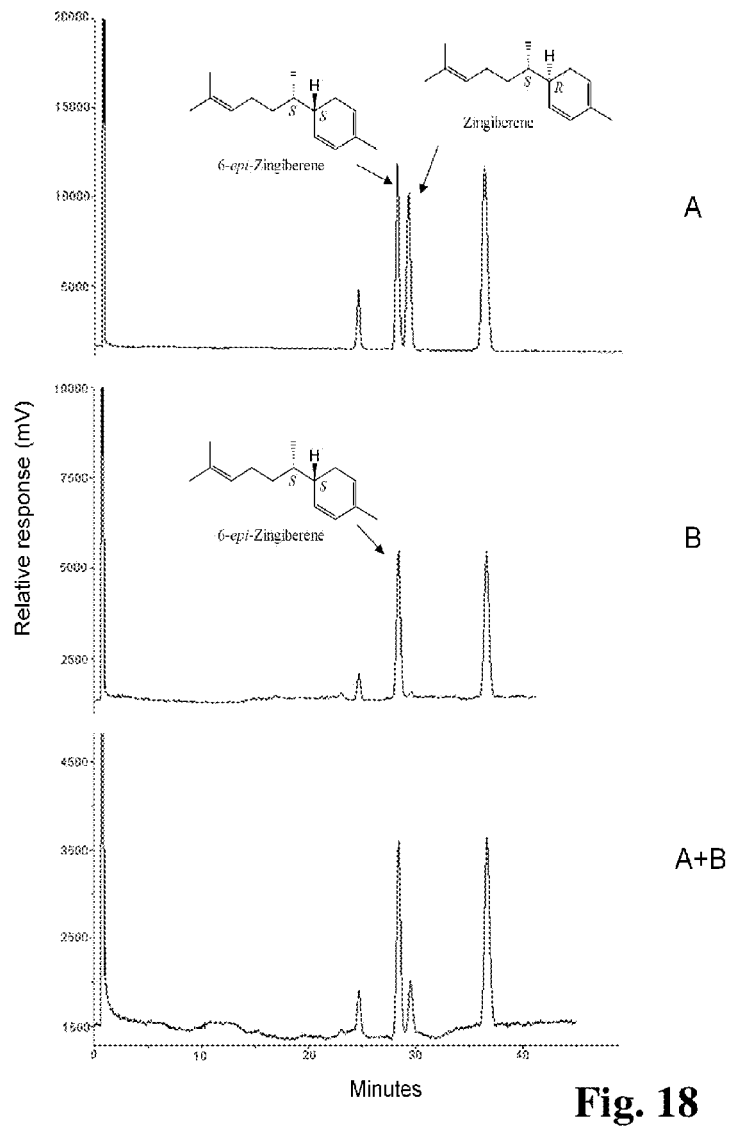
FIG. 18 shows GC-FID analyses of (7S)-bisabolatrienes on HYDRODEX-β-6TBDM as described below. Part A: dehydration products from mixture 15; Part B: dehydration products from alcohol 25; Part C: mixture of dehydration products from 15 and 25.

Dehydration of a mixture 15 with 7S configurations provided expected hydrocarbon mixtures (FIG. 16). Interestingly, in this case diastereomeric zingiberenes but not β-sesquiphellandrenes were separated on HYDRODEX-β-6TBDM column (FIG. 17, Part A). This simplified our task of assigning their absolute configurations since natural (−)-zingiberene has 6R,7S configuration (Soffer, M. D., and L. A. Burk, Tetrahedron Lett., 26: 3543-3546 (1985); Bhonsle et al. 1994) and it matched (FIG. 17, part B) the slower-eluting peak of the two stereoisomeric zingiberenes. Hence, the faster-eluting peak was assigned 6S,7S configuration.

Dehydration of alcohol 24 provided 6R,7S-zingiberene (FIG. 16, FIG. 17, part C), and because 24 is a cis-alcohol, its absolute configuration had to be 3R,6R,7S. Conversely, alcohol 25 furnished 6S,7S-zingiberene upon dehydration (FIG. 14, FIG. 15, part B) and because it has a trans relative configuration, its absolute configuration should be 3R,6S,7S.

Syntheses of chiral 10,11-epoxy-1-bisabolen-3-ols from 1,10-bisaboladien-3-ols: For enantioselective epoxidation of a carbon-carbon double bond in the side chain of 1,10-bisaboladien-3-ols, we used a sequence of a Sharpless asymmetric dihydroxylation (Sharpless, K. B., et al., J. Org. Chem., 57: 2768-2771 (1992)) and stereoselective cyclization of intermediate diols through intermediate mesylates (Frater, G., and U. Müller, Helvetica Chimica Acta, 72: 653-658 (1989); Moore, 1999). Dihydroxylation of alcohol 23 with AD-mix-α has already been shown in FIG. 12, and analogous reaction of alcohols 20, 22, 23, and 24 and further conversions of diols to epoxides is demonstrated in FIG. 19. Dihydroxylations of all 1,10-bisaboladien-3-ols were highly regio selective in that reactions occurred primarily at the trisubstituted double bonds and provided triols 33-38 in good yields. Absolute configuration of triol 28, confirmed by X-ray analysis, showed that C-10 has S configuration (FIG. 12), as it was expected from original Sharpless asymmetric dihydroxylation conditions and other sources (Moore, 1999; Khrimian et al., 2012). Thus we assigned other triols (33, 35) originated from AD-mix-α dihydroxylations 10S configurations, and triols obtained from AD-mix-β dihydroxylations (34, 36, 37, and 38) 10R configurations. In the last step, triols were converted to mesylates via secondary hydroxy groups (FIG. 19), and the mesylates were cyclized to epoxides with KOH in MeOH (Frater and Müller, 1989; Moore, 1999; Khrimian et al., 2012). Since this intramolecular cyclization was shown to proceed with inversion of configuration (Frater and Müller, 1989; Moore, 1999; Khrimian et al., 2012), carbon atoms at position 10 in the epoxybisabolenols 2 and 39 were assigned R configuration and those in compounds 1, 3, 19, and 40 S configurations.

Synthesis of zingiberene epoxide 41 and mixture of epoxides 4, 5, and 6: Natural zingiberene isolated from ginger oil (Millar, 1998) was dihydroxylated with AD-mix-β to a diol that was converted to (6R,7S,10S)-10,11-epoxy-1,3-bisaboladiene (41), or zingiberene epoxide, as described above (FIG. 20, part A). The epoxide 41 contained about 8% of aromatic curcumene epoxide. These two matched minor compounds 5 and 6 (FIGS. 1 and 2) present in the *H. halys* male aeration. The mixture of trans-bisaboladienols 16 was dehydrated with POCl$_3$ in dry pyridine to provide a mixture of bisabolatrienes 42, which were further epoxidized with MCPBA to mixture 43 that contained 82% 4, 2% 5, and 13% 6 (FIG. 20).

Synthesis of epoxide mixture 44 from alcohol 26 (FIG. 11): The epoxidation was conducted using MCPBA analogously previously described.

Field Bioassays. Chemicals tested in field trials are presented in Table 2. 2011 Results:

Trial 1: At AFRS, wild captures were very low and the GLM for adult captures was not significant (F=0.77; df=7, 12; P=0.6170) (Table 3). At Beltsville, the GLM for adult captures was significant (F=1.98; df=12, 227; P=0.0270); significantly more adults were captured in traps baited with Lure #2 compared with Lure #1 or the unbaited control (#4) (Table 4).

Trial 2: At AFRS (F=1.59; df=7, 72; P=0.1521) and Beltsville (F=0.92; df=12, 147; P=0.5288) the GLMs for adult captures were not significant. Numerically higher captures were recorded for #2 and #6 (Tables 3 and 4).

Trial 3: The GLM for adult captures was significant (F=3.77; df=7, 172; P<0.0001) at AFRS; significantly greater numbers of adults were captured in traps baited with #6 compared with #4 and #7, with #2 being intermediate (Table 3). At Beltsville, the model for adult captures also was significant (F=3.90; df=12, 307; P<0.0001); significantly greater captures were recorded in traps baited with #2 and #6 compared with #4 (unbaited control) (Table 4). For nymphal captures, the model was not significant at AFRS (F=0.95; df=7, 172; P=0.4711). Nymphal captures were significant at Beltsville (F=2.29; df=12, 307, P=0.0083), however, there were no differences in captures among lure types (Tables 3 and 4).

Trial 4: At AFRS, the model for adult captures (F=0.29; df=3, 56; P=0.8359) and nymphal captures F=0.64; df=3, 56; P=0.5929) were not significant (Table 3). At Beltsville, the model was significant (F=4.78; df=12, 147; P<0.0001) with significantly greater captures recorded in traps baited with #6 compared with #4 (unbaited control) and with captures in traps baited with #2 and #7 being intermediate. Similarly, the model for nymphal captures also was significant (F=7.66; df=12, 147; P<0.0001) with traps baited with #6 capturing significantly more than unbaited traps (Table 4).

Trial 5: The GLM for adult captures was significant (F=4.34; df=7, 152, P=0.0002) at AFRS with significantly greater captures in traps baited with #6 compared with #8 and #4 (unbaited control) (Table 3). At Beltsville, the model for adult captures was significant as well (F=9.20; df=12, 387; P<0.001) with a similar pattern of captures as traps baited with #6 had significantly greater captures than #8 and #4 (unbaited control) (Table 4). At AFRS (F=4.93; df=7, 152; P<0.0001) and Beltsville (F=12.47; df=12, 387; P<0.0001) the models for nymphal captures were significant but the effect of lure type was not (Tables 3 and 4).

Trial 6: At AFRS, the GLM for adult captures was significant (F=2.70; df=6, 89; P=0.0187). Similarly the ANOVA for nymphal captures was significant (F=18.25; df=6, 89; P<0.0001) (Table 4). This trial was not conducted in Beltsville.

Trial 7: The GLM for adult captures comparing a 50 mg load of #6 with commercially available methyl (2E,4E,6Z)-decatrieonate or unbaited traps was significant (F=4.02; df=7, 208; P<0.0004). Significantly more adults were captured in traps baited with #6 or with MDT compared with unbaited traps. Among nymphs the model was also significant (F=5.70; df=7, 208 P<0.0001) (Table 3).

Trial 8: The GLM for adult captures at AFRS was significant (F=6.65; df=8, 191; P<0.0001) with captures in traps baited with #9, #6, and #2 being significantly greater than traps baited with #1 or unbaited control traps (#4) (Table 3). At Beltsville the model also was significant (F=6.18; df=13, 361; P<0.0001) with captures in traps baited with #6 and #9 being significantly greater than traps baited with #1 and unbaited traps (#4) (Table 4). At both locations the models for nymphal captures were significant (AFRS; F=9.15; df=8, 181; P<0.0001; Beltsville; F=4.17; df=13, 361; P<0.0001) but not the effect of lure type (Tables 3 and 4).

Trial 9: The GLM for adult captures was statistically significant at AFRS (F=17.29; df=8, 166, P<0.0001) with traps baited with #10 capturing significantly more adults than all other treatments (Table 3). Similarly, adult captures at Beltsville (F=8.82; df=13, 261; P<0.0001) were significantly greater than in traps baited with #10 (Table 4). For nymphal captures at AFRS (F=2.21; df=8, 166; P<0.0001) and Beltsville (F=2.88; df=13, 261; P=0.0007) the models were significant but there were no significant differences among lure types. (Tables 3 and 4).

Trial 10: The model for adult captures was significant (F=4.77; df=8, 116; P<0.0001) with significantly greater captures in traps baited with #10 compared with #6, #11, and unbaited traps (#4). Captures in traps baited with #3 (MDT) were significantly greater than the control (#4). The model for nymphal captures also was significant (F=4.55; df=8, 116; P<0.0001) with more nymphs captured in traps baited with #3 (MDT) compared with all other treatments except #10 (Table 3).

Trial 11: A trial evaluating dose-dependent response of #6 revealed no significant differences among treatments for adults and nymphs, although the models were significant (adult; F=2.41; df=6, 41; P=0.0437, nymph: F=2.44; df=6, 41; P=0.0415) (Table 3).

Trial 12: The GLM for adult captures was significant (F=4.24; df=8, 141; P<0.0001) at AFRS and Beltsville (F=3.51; df=13, 386; P<0.0001) with significantly greater captures recorded for traps baited with #14 compared with all other treatments (Tables 3 and 4). For nymphs, the model at AFRS (F=0.79; df=8, 141; P=0.6116) and Beltsville (F=0.69; df=13, 386; P<0.0001) were not significant but very few nymphs were present in the field at that time (Tables 3 and 4).

Trial 13: Although the model for dose-dependent response to #10 was not significant at AFRS for adults (F=1.16; df=7, 92; P=0.3314), numerically greatest captures were recorded with the highest dose (48 mg of material). The model for nymphal captures also was not significant (F=1.47; df=7, 92; P=0.1885) but nymphal populations were very low at the time (Table 3).

Trial 14: A final trial conducted late in the season resulted in models for adult captures (F=0.92; df=5, 54; P=0.4778) that was not significant. The model for nymhal captures was significant (F=3.22; df=5, 54: P=0.0128) but there was no significant difference in captures across treatments (Table 3).

2012 Results. Trial 1: The GLM for adult captures was significant (F=5.67; df=1, 78; P=0.0197) but no nymphs were captured because it was very early in the season and nymphs were not yet present. Mean adult captures for #10 was 1.93±0.71 SE per trap per sample and for #4 (unbaited) was 0.20±0.10 SE (Table 5).

Trial 2: The model for trial two was significant for adult captures at AFRS (F=7.33; df=6, 129; P<0.0001) and Beltsville (F=2.71; df=6, 129; P=0.0165). At AFRS, significantly more adults were captured in #12 compared with all other treatments (including unbaited control) except #10 and #19 (Table 5). At Beltsville, #12 captured significantly more than #4 (unbaited control) with all other treatments being intermediate (Table 6). The model for nymphal captures was significant at AFRS (F=4.25; df=6, 129; P<0.001) but not at Beltsville likely because nymphs can be more localized in their distributions (F=1.49; df=6, 129; P=0.1880). At AFRS, significantly more adults were captured in traps baited with #10 compared with #13, #19 and the unbaited control (Tables 5 and 6).

Trial 3: The model for adult captures was significant at AFRS (F=36.46; df=6, 269; P<0.001) and Beltsville (F=16.53; df=6, 269; P<0.0001). At AFRS, significantly more adults were captured in traps baited with #10 compared with all other treatments except #12 (Table 5). At Beltsville, traps baited with #10 captured numerically more than all other treatments and statistically more than #23 and the unbaited control #4 (Table 6). Importantly, #22 was more attractive than #23 at both locations, thus indicating that stereoisomer 2 is not attractive to BMSB. The model for nymphal captures was significant at AFRS (F=12.73 df=6, 269; P<0.001) and Beltsville (F=5.59; df=6, 269; P<0.0001). At AFRS, significantly more adults were captured in traps baited with #10 and #12 compared with all #22, #23 and #4 (control) (Table 5). At Beltsville, traps baited with #12 captured significantly more than traps baited with #23 and the unbaited control #4 (Table 6).

Trial 4: The model for trial four was significant at AFRS (F=5.10; df=6, 164; P<0.001) and Beltsville (F=8.47; df=6, 164; P<0.001). At AFRS, significantly more adults were captured in #24H compared with all other treatments except #12, #18, and #25 (Table 5). At Beltsville, all baited traps captured significantly more than the unbaited control #4 (Table 6). The model for nymphal captures was not significant at AFRS (F=1.14; f=6, 164; P=0.3422) or Beltsville (F=1.45; df=6, 129; P=0.2104) again because of localized distribution of nymphs across experimental sites.

Purity Trial: The model for the purity trial was significant at AFRS (F=4.21; df=3, 136; P<0.001) and Beltsville (F=9.07; df=3, 112, P<0.001). Statistically identical adult captures were recorded for #10, #20 and #21, all of which were significantly greater than the unbaited control (Table 7). Nymphal populations were not present at the time this trial was conducted.

Dose-Dependent Response: The model for dose-dependent responses from adults was significant at Shepherdstown (F=6.03; df=4, 155; P<0.001), Keedysville (F=20.71; df=4, 155; P<0.001), and Beltsville (F=20.55; df=4, 152; P<0.001). At Keedysville and Beltsville, significantly more adults were captured in traps baited with lures containing 100 mg #10 compared with all other treatments. At Shepherdstown, traps baited with 100 mg lures captured significantly more adults compared with all other treatments except 10 mg lures (Table 8). For nymphal populations, the models were again significant at Shepherdstown (F=10.79; df=4, 155; P<0.001), Keedysville (F=7.94; df=4, 155; P<0.001), and Beltsville (F=5.32; df=4, 152; P<0.001). Significantly more nymphs were captured in traps baited with 100 mg of #10 compared with all other treatments at Shepherdstown and Keedysville sites, and at Beltsville the greatest captures were also recorded from traps baited with 100 mg lures (Table 8).

Synergy Trial: At Beltsville and Arden, the combined lure proved superior to either the #10 or the MDT lure, or the unbaited treatment, for season-long total captures of both adults and nymphs (Beltsville adults, $F_{(3,12)}$=22.12, p<0.0001; Arden adults, $F_{(3,8)}$=22.57, p=0.0003; Beltsville nymphs, $F_{(3,12)}$=18.00, p<0.0001; Arden nymphs, $F_{(3,8)}$=7.54, p=0.0102) (Table 9). In addition, for adults at both locations, there was a significant two-way interaction between the two lures (indicated by * in Table 9; Beltsville adults, $F_{(1,12)}$=7.36, p=0.0189; Arden adults, $F_{(1,8)}$=13.26, p=0.0066; Beltsville nymphs, $F_{(1,12)}$=3.47, p=0.0870; Arden nymphs, $F_{(1,8)}$=4.81, p=0.0597) such that the effect of combining the lures exceeded the additive effect of the two separate lures. This surprisingly represented a synergistic effect between the two lure types in capture of BMSB. The magnitude of the effect was such that the combined lure captures exceeded the next most attractive lure (in all four cases for season-long totals, the MDT lure) by a multiple of 2.02 to 4.24 times (aggregate 2.97 times), constituting from 57.3% to 75.9% of total captures (aggregate 65.5% of all captures).

Figure 21:
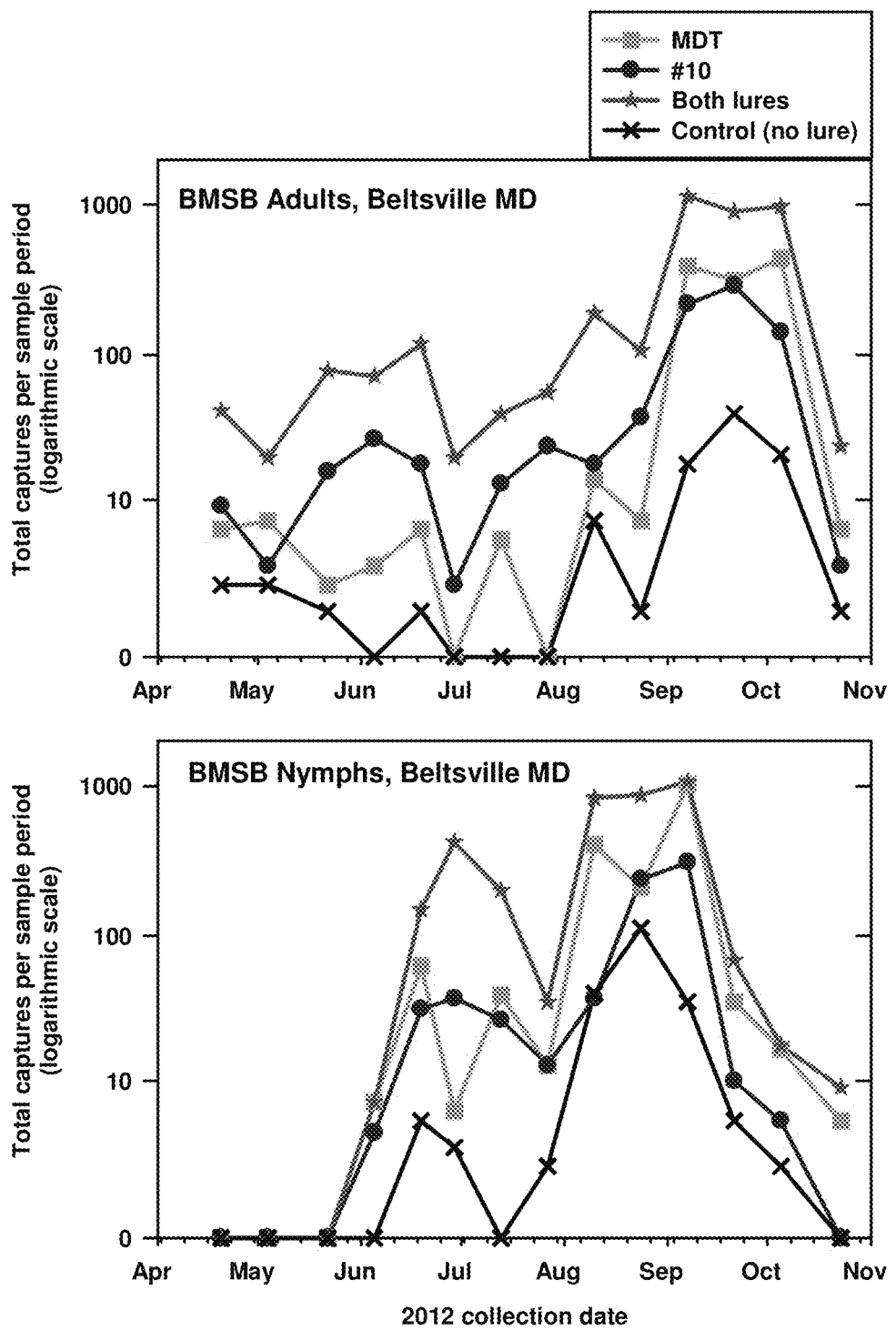
FIG. 21 shows season-long captures of BMSB at Beltsville, Md., with MDT, #10 lure, and combination of MDT and #10 as described below.

The combined lure ranked highest for all 14 periods in Beltsville for both adults and nymphs; there were significant differences in lure treatments for 12 of 14 periods for adults and 6 of 11 periods for nymphs (for 3 periods, zero nymphs were captured, Table 10; FIG. 21). In five time periods for Beltsville adults, and one for nymphs, there was a significant interaction representing synergistic effect for the combined lure (indicated by * at end of row in Table 10). For the Arden site, the combined lure ranked highest for adult captures for 11 time periods (tied in $3^{rd}$ period), and for 6 of 9 time periods for nymphs, there being significant differences in treatments only for those periods in which the combined lure was most attractive (3 periods for adults and 2 for nymphs, Table 11 and FIG. 22). In 2 time periods each for adults and for nymphs at the Arden site, there was a significant interaction representing synergistic effect for the combined lure (indicated by * at end of row in Table 11).

Figure 22:
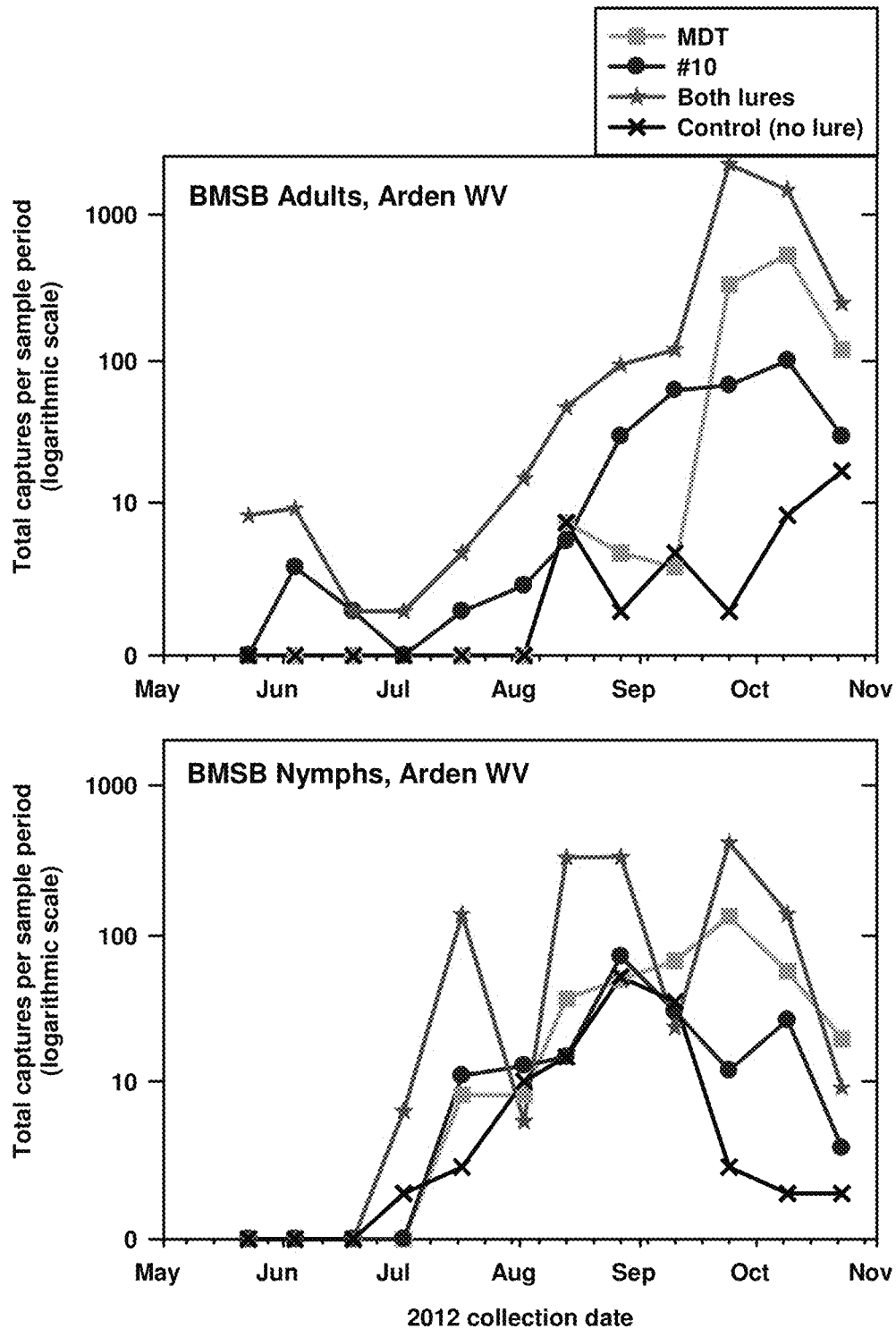
FIG. 22 shows season-long captures of BMSB at Arden, W. Va., with MDT, #10 lure, and combination of MDT and #10 as described below.

FIGS. 21 and 22 show that the early-season detection of adult BMSB, which is considered critical by pest managers in crops such as stone fruit orchards, was highest for the combined lure even with low overall numbers.

Discussion: Gas-chromatographic analyses of BMSB male airborne extract and synthetic mixtures on a HYDRO-DEX-β-6TBDM column helped tremendously reduce the number of stereoisomers that could potentially constitute an aggregation pheromone to only four compounds, 1, 2, 3, and 19. However, some other stereoisomers were also of importance for assignment of absolute configurations of target molecules. Given that no single stereoisomer of 10,11-epoxy-1-bisabolen-3-ol has ever been synthesized, we faced a formidable task of developing a general synthetic methodology for construction of these valuable entities. In development of such an approach, our attention focused on a recently discovered rhodium-catalyzed asymmetric 1,2-addition of aluminum organyl compounds to enones (Siewert et al., 2007); this reaction provided an excellent enantioselectivity (>96%) when cyclohex-2-enone was used as a substrate. By introducing a stereogenic center at position 7, we had an opportunity to test the diastereoselectivity of this reaction as well. We found that ketones 10 and 14, each represented by two diastereomers, principally complied with the stereochemistry of the original reaction. Despite differences in reactivities, diastereomers furnished (R) alcohols when using (S)-BINAP as a chiral ligand and (S) alcohols when (R)-BINAP was used (FIG. 11).

What was surprising and remarkable from our extensive synthetic studies was that a pair of easily separable stereoisomers (one cis and another trans) could be synthesized from a single reaction of diasteromeric mixtures 10 or 14 with trimethylaluminum in rhodium-catalyzed asymmetric 1,2-addition conditions. Because both (S)— and (R)-BINAP were readily available, all eight possible stereoisomers of 1,10-bisaboladien-3-ol have been synthesized. We have herein described seven stereoisomers of 10,11-epoxy-1-bisabolen-3-ol but preparations of all sixteen are underway and will be reported elsewhere. This will help greatly in resolving stereochemical issues of pheromones of other true bugs such as *Murgantia histrionica* and *Tibraca limbativentris*, and finally in determining the stereostructure of zingiberenol.

The Sharpless asymmetric dihydroxylation of 1,10-bisaboladien-3-ols offered a simple two-step route to make chiral 10,11-epoxy-1-bisabolen-3-ols with predictable stereochemistry. In addition, one intermediate triol (28) turned out to be crystalline which allowed us to apply X-ray crystallography to determined its stereostructure. The fact that 28 and its precursor 23 had trans configuration enabled us to assign relative configurations to all synthesized compounds.

The selection of dehydration reactions served the purpose of chemically correlating 1,10-bisaboladien-3-ols with zingiberene and β-sesquiphellandrene and thus determine their absolute configurations.

In early 2011, we assessed field attractiveness of treatments originating from (S)-citronellal to BMSB. Trapping studies revealed that mixture 17 (Lure #2), which consisted of four cis-10,11-epoxy-1-bisabolen-3-ols, was surprisingly moderately active. The only stereoisomer in mixture 17 that matched the main male-specific compound collected from *H. halys* was stereoisomer 19, while three other stereoisomers did not have any relevance to BMSB. However, 19 was inactive (Lure #1) in trapping BMSB (Trial 8, Trial 1, Beltsville), and at this point we do not have any explanation on why 17 was active. Without being bound by theory, we speculate that there are certain stereoisomers in 17 that are structurally close to the true pheromone (see below) and thus enter receptor sites of BMSB and elicit behavioral responses from them. Addition of a mixture of four trans-10,11-epoxy-1-bisabolen-3-ols 18 to 17 (Lure #6) surprisingly somewhat increased the field attractiveness (but not significantly) which might have practical implications if one considers manufacturing the attractant for the BMSB starting from racemic citronellal (see below). Lure #9, consisting of lure #6 and 43 (containing epoxides 4, 5, and 6), was not statistically significantly different from lure #6 in field trials.

In late 2011, we evaluated field attractiveness of 10,11-epoxy-1-bisabolen-3-ols originating from (R)-citronellal. BMSB trapping studies revealed that a mixture of 7 and 8 in a 3:1 ratio (Lure #10) was surprisingly a very attractive stimulus for BMSB; significantly more adults were captured in traps baited with this mixture compared with all other lure formulations (Tables 3 and 4). This trial, however, occurred late in the season, thus leading to two key questions that were addressed during 2012. First, we determined that BMSB was surprisingly attracted to this lure treatment in the early-season, a key consideration for successful season-long monitoring as well as development of attract and kill strategies. In this case, we found that BMSB will surprisingly respond to #10 after leaving overwintering sites in the early-season. These results were based on trials conducted in late March and early April in 2012. Significantly more adults were attracted to traps baited with #10 compared with unbaited traps.

Second, another key experiment included the level of purity required for optimal attraction of BMSB to #10. In trials conducted at AFRS and Beltsville, septa loaded with 10.7 mg of #10, as well as a crude mixture loaded at 38 mg (Lure #20; and containing the same amount of cis-epoxybisabolenols 7 (8 mg) as in #10) and a mixture produced by using only one chromatographic purification (Lure #21, loading 10.7 mg) were surprisingly equally attractive to BMSB adults in the field. These results surprisingly indicated that byproducts and nonessential compounds from the synthesis process did not lead to any inhibition of attraction to the primary stimuli. Thus the commercialization will not require extensive and costly purification for optimal attraction, thereby reducing overall costs. Because of the high attractiveness of #10 and moderate attractiveness of #6, it is also reasonable to anticipate that mixtures attractive to BMSB could also be prepared starting from racemic citronellal.

In dose-dependent trials with #10 conducted at three locations in MD and WV, captures of both adults and nymphs increased with increasing amounts of #10, importantly confirming the quantitative response of both life stages. These results indicated that sensitivity of monitoring tools can be increased with increasing dose. These results also indicated that the potential of attract and kill or mass trapping strategies holds promise for all mobile stages of this invasive species.

Methyl (2E,4E,6Z)-decatrieonate (MDT), the aggregation pheromone of *Plautia stali* in Asia (Sugie et al., 1996), is attractive to BMSB in its native range (Tada et al., 2001a, b). When it was deployed in Maryland, it also proved attractive to the recently invasive BMSB (Khrimian 2008; Aldrich et al. 2007). However, the basis for BMSB attraction to MDT is unknown because BMSB does not produce or contain MDT or related compounds. Adults are reliably attracted only late in the season (Khrimian et al. 2008, Leskey et al. 2012b). Due to this attraction and that of Lure #10 as discussed above, we deployed MDT and #10 together, as well as separately, to determine if any interference would make their simultaneous deployment inferior to either material alone. Surprisingly however, MDT (~120 mg lure) with #10 (10.7 mg lure) showed superior attractiveness in field trials (for both nymphs and adults of BMSB (Tables 11-13 and FIGS. 18-19)) to either #10 or the MDT lure alone. This finding indicates that the combined lure (MDT plus #10) will be superior for season-long attraction for monitoring and/or trapping and management of BMSB adults and nymphs.

In order to find an explanation for why Lure #10 was active, we separately tested two components of it: cis-10,11-epoxy-1-bisabolen-3-ols (mixture 7, Lure #12) and trans-10,11-epoxy-1-bisabolen-3-ols (mixture 8, Lure #13). Trapping results in 2012 revealed that mixture 7 surprisingly had about the same level of attractiveness as #10 while 8 was only moderately active. As we showed earlier (FIG. 8), two stereoisomers present in mixture 7, (3S,6S,7R,10S)-10,11-epoxy-1-bisabolen-3-ol (1) and (3R,6R,7R,10R)-10,11-epoxy-1-bisabolen-3-ol (2), matched the main *H. halys* male-produced compound on chiral GC analysis. Field trapping in 2012 showed that stereoisomer 1 (Lure #22) attracted BMSB females, males, and nymphs. Stereoisomer 2 was not attractive to BMSB (Lure #23) and in three out of four trials did not increase attractiveness of 1 when added in an equal amount (Lure #24L). Even though doubling the concentrations of 1 and 2 resulted in a better attractant (Lure #24H) than 1 alone, we believe compound 1 was primarily responsible for the increased attractiveness because 2 was not attractive by itself. Therefore, we concluded that the main compound of the BMSB male-produced aggregation pheromone was (3S,6S,7R,10S)-10,11-epoxy-1-bisabolen-3-ol (1) and that it is doubtful that stereoisomer 2 is also a part of the pheromone. The second most abundant compound in the *H. halys* male aeration closely matched (3R,6S,7R,10S)-10,11-epoxy-1-bisabolen-3-ol (3) by GC analysis on a chiral column (FIG. 10) and synthetic 3 was moderately attractive to BMSB (Lure #18). Thus the behavior of single isomers 1 and 3 in field trapping resembled the attractiveness of mixtures 7 and 8 containing these compounds.

In conclusion, we have discovered a male-produced aggregation pheromone of the brown marmorated stink bug which attracted males, females and nymphs. We also discovered a synergistic relationship between this pheromone and the aggregation pheromone of *Plautia stali*, which surprisingly indicated that a combination of these two pheromones is the superior season-long attractant for monitoring and management of brown marmorated stink bug adults and nymphs. Furthermore, we developed a novel synthesis of the brown marmorated stink bug pheromone, amenable to scale-up, and successfully synthesized an experimental batch through a private-sector contract laboratory under a Confidentiality Agreement; this process is economical due to circumventing labor-intensive chromatographic separations.

All of the references cited herein, including U.S. patents, are incorporated by reference in their entirety. Also incorporated by reference in their entirety are the following references: Bae, S. D., et al., Journal of Asia-Pacific Entomology, 15: 148-151 (2012); Zahn, D. K., et al., J. Chem. Ecol., 38: 126 (2012).

Thus, in view of the above, there is described (in part) the following:

(1) A composition comprising (or consisting essentially of or consisting of) at least one member selected from the group consisting of (3R,6R,7R,10S)-10,11-epoxyl-bisabolen-3-ol (3R,6R,7R,10R)-10,11-epoxyl-bisabolen-3-ol, (3S,6S,7R,10S)-10,11-epoxyl-bisabolen-3-ol, (3S,6S,7R,10R)-10,11-epoxyl-bisabolen-3-ol, and mixtures thereof, and optionally a carrier material or carrier. The above composition, comprising (or consisting essentially of or consisting of) at least two members selected from the group consisting of (3R,6R,7R,10S)-10,11-epoxyl-bisabolen-3-ol, (3R,6R,7R,10R)-10,11-epoxyl-bisabolen-3-ol, (3S,6S,7R,10S)-10,11-epoxyl-bisabolen-3-ol, (3S,6S,7R,10R)-10,11-epoxyl-bisabolen-3-ol, and mixtures thereof. The above composition, comprising (or consisting essentially of or consisting of) at least three members selected from the group consisting of (3R,6R,7R,10S)-10,11-epoxyl-bisabolen-3-ol, (3R,6R,7R,10R)-10,11-epoxyl-bisabolen-3-ol, (3S,6S,7R,10S)-10,11-epoxyl-bisabolen-3-ol, (3S,6S,7R,10R)-10,11-epoxyl-bisabolen-3-ol, and mixtures thereof. The above composition, comprising (or consisting essentially of or consisting of) (3R,6R,7R,10S)-10,11-epoxyl-bisabolen-3-ol, (3R,6R,7R,10R)-10,11-epoxyl-bisabolen-3-ol, (3S,6S,7R,10S)-10,11-epoxy-1-bisabolen-3-ol, and (3S,6S,7R,10R)-10,11-epoxy-1-bisabolen-3-ol.

The above composition, further comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition according to claim 1, further comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) at least one member of the group consisting of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof.

The above composition, further comprising (or consisting essentially of or consisting of) methyl (2E,4E,6Z)-decatrieonate.

The above composition, further comprising (or consisting essentially of or consisting of) at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising a *Halyomorpha halys* attracting effective amount of the above composition.

A kit for attracting *Halyomorpha halys*, comprising (or consisting essentially of or consisting of):

a. first attractant comprised of the above composition on a first carrier, and b. a second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(17) A composition comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof, and optionally a carrier material or carrier. The above composition, comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least two members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least three members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, and (3S,6S,7R,10R)-10,11-epoxy-1-bisabolen-3-ol.

The above composition, further comprising (or consisting essentially of or consisting of) at least one member of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, further comprising (or consisting essentially of or consisting of) at least two members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, further comprising (or consisting essentially of or consisting of) at least three members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, further comprising (or consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, and (3S,6S,7S,10R)-10,11-epoxy-1-bisabolen-3-ol.

The above composition, further comprising (or consisting essentially of or consisting of) at least one member of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S, 10S)-10,11-epoxy-1-bisabolen-3-ol, and mixtures thereof.

The above composition, further comprising (or consisting essentially of or consisting of) at least two members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S, 10S)-10,11-epoxy-1-bisabolen-3-ol, and mixtures thereof.

The above composition, further comprising (or consisting essentially of or consisting of) at least three members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S, 10S)-10,11-epoxy-1-bisabolen-3-ol, and mixtures thereof.

The above composition, further comprising (or consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol.

The above composition, further comprising (or consisting essentially of or consisting of) methyl (2E,4E,6Z)-decatrieonate.

The above composition, further comprising (or consisting essentially of or consisting of) at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (or consisting essentially of or consisting of):

a. first attractant comprised of the above composition on a first carrier, and b. a second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(40) A composition comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R, 10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof, and optionally a carrier material or carrier.

The above composition, comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R, 10R)-10,11-epoxy-1-bisabolen-3-ol, and mixtures thereof.

The above composition, comprising (or consisting essentially of or consisting of) at least two members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R, 10R)-10,11-epoxy-1-bisabolen-3-ol, and mixtures thereof.

The above composition, comprising (or consisting essentially of or consisting of) at least three members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R, 10R)-10,11-epoxy-1-bisabolen-3-ol, and mixtures thereof.

The above composition, comprising (or consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, and (3S,6S, 7R,10R)-10,11-epoxy-1-bisabolen-3-ol.

The above composition, comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R, 7R,10R)-10,11-epoxy-1-bisabolen-3-ol, and mixtures thereof. The above composition, comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) at least one member of the group consisting of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S, 10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof.

The above composition, further comprising (or consisting essentially of or consisting of) at least one member of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S, 10R)-10,11-epoxy-1-bisabolen-3-ol, and mixtures thereof.

The above composition, further comprising (or consisting essentially of or consisting of) at least two members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S, 10R)-10,11-epoxy-1-bisabolen-3-ol and mixtures thereof.

The above composition, further comprising (or consisting essentially of or consisting of) at least three members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, further comprising (or consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, and (3S,6S,7S,10R)-10,11-epoxy-1-bisabolen-3-ol.

The above composition, further comprising (or consisting essentially of or consisting of) at least one member of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) at least two members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) at least three members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol.

The above composition, further comprising (or consisting essentially of or consisting of) methyl (2E,4E,6Z)-decatrieonate.

The above composition, further comprising at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (or consisting essentially of or consisting of):
a. first attractant comprised of the above composition on a first carrier, and
b. a second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(65) A composition comprising (or consisting essentially of or consisting of) at least one member of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof, and optionally a carrier material or carrier. The above composition, comprising (or consisting essentially of or consisting of) at least two members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, comprising (or consisting essentially of or consisting of) at least three members of the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, comprising (or consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, and (3S,6S,7S,10R)-10,11-epoxy-1-bisabolen-3-ol.

The above composition, further comprising (or consisting essentially of or consisting of) at least one member selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) at least two members selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) at least three members selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, further comprising (or consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least two members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least three members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, and (3S,6S,7R,10R)-10,11-epoxy-1-bisabolen-3-ol.

The above composition, further comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) methyl (2E,4E,6Z)-decatrieonate.

The above composition, further comprising (or consisting essentially of or consisting of) at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (or consisting essentially of or consisting of):

a. first attractant comprised of the above composition on a first carrier, and b. second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(89) A composition comprising (or consisting essentially of or consisting of) at least one member of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof, and optionally a carrier material or carrier. The above composition, comprising (or consisting essentially of or consisting of) at least two members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, comprising (or consisting essentially of or consisting of) at least three members of the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, comprising (or consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol.

The above composition, further comprising (or consisting essentially of or consisting of) at least one member of the group consisting of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and mixtures thereof. The above composition, further comprising (or consisting essentially of or consisting of) at least two members of the group consisting of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and mixtures thereof. The above composition, further comprising (or consisting essentially of or consisting of) at least three members of the group consisting of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and mixtures thereof. The above composition, further comprising (or consisting essentially of or consisting of) (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, and 3S,6S,7S,10R)-10,11-epoxy-1-bisabolen-3-ol.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least two members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least three members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11- epoxy-1-bisabolen-3-ol, (3S,6S,7R,10R)-10,11-epoxy-1-bisabolen-3-ol, and mixtures thereof. The above composition, further comprising (or consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, and (3S,6S,7R,10R)-10,11-epoxy-1-bisabolen-3-ol.

The above composition, further comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) methyl (2E,4E,6Z)-decatrienoate.

The above composition, further comprising (or consisting essentially of or consisting of) at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (or consisting essentially of or consisting of):
a. first attractant comprised of the above composition on a first carrier, and
b. a second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(113) A composition comprising (or consisting essentially of or consisting of) at least one member selected from the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof.

The above composition, comprising (or consisting essentially of or consisting of) at least one member selected from the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, comprising (or consisting essentially of or consisting of) at least two members selected from the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, comprising (or consisting essentially of or consisting of) at least three members selected from the group consisting of (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, and mixtures thereof. The above composition, comprising (or consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, and (3S,6S,7S,10R)-10,11-epoxy-1-bisabolen-3-ol.

The above composition, comprising (or consisting essentially of or consisting of) at least one member selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, comprising (or consisting essentially of or consisting of) at least two members selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, comprising (or consisting essentially of or consisting of) at least three members selected from the group consisting of (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and mixtures thereof. The above composition, comprising (or consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof.

The above composition, further comprising (or consisting essentially of or consisting of) at least one member selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least two members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) at least three members selected from the group consisting of (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and mixtures thereof. The above composition, further comprising (or consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, and (3S,6S,7R,10R)-10,11-epoxy-1-bisabolen-3-ol.

The above composition, further comprising (or consisting essentially of or consisting of) at least one member selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least two members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition, further comprising (or consisting essentially of or consisting of) at least three members selected from the group consisting of (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, and mixtures thereof. The above composition according to claim 113, further comprising (or consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol.

The above composition, further comprising (or consisting essentially of or consisting of) methyl (2E,4E,6Z)-decatrieonate.

The above composition, further comprising (or consisting essentially of or consisting of) at least one member of the group consisting of 10,11-epoxy-1,3(15)-bisaboladiene, 10,11-epoxy-1,3-bisaboladiene, 10,11-epoxy-1,3,5-bisabotriene, (3S,6S,7S,10R)-10,11-epoxy-1-bisabolen-3-ol, and mixtures thereof.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (or consisting essentially of or consisting of):
a. first attractant comprised of the above composition on a first carrier, and
b. a second attractant comprised of methyl (2E,4E,6Z)-decatrieonate on a second carrier or on said first carrier.

The above kit, further comprising (or consisting essentially of or consisting of) an insect trap for housing said first and second carriers.

The above kit, further comprising (or consisting essentially of or consisting of) written instructions directed to deploying the attractants at separate seasonal times.

The above kit, further comprising (or consisting essentially of or consisting of) a third carrier and one or more insecticides on the third carrier.

(138) A method of making a mixture of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, and (3S,6R,7S,10S)-10,11-epoxy-1-bisabolen-3-ol, comprising (or consisting essentially of or consisting of) reacting (S)-citronellal with formaldehyde in the presence of piperidine to form (S)-2-methylenecitronellal, reacting (S)-2-methylenecitronellal with methyl acetoacetonate to form (7S)-7,11-dimethyl-1,10-bisaboladien-3-one, reacting (7S)-7,11-dimethyl-1,10-bisaboladien-3-one with methyl lithium to form trans-(7S)-3,7,11-trimethyl-1,10-bisaboladien-3-ols and cis-(7S)-3,7,11-trimethyl-1,10-bisaboladien-3-ols; separating trans-(7S)-3,7,11-trimethyl-1,10-bisaboladien-3-ols and cis-(7S)-3,7,11-trimethyl-1,10-bisaboladien-3-ols; and reacting trans-(7S)-3,7,11-trimethyl-1,10-bisaboladien-3-ols with m-chloroperbenzoic acid to form trans-10,11-epoxy-1-bisabolen-3-ols 1; and reacting cis-(7S)-3,7,1'-trimethyl-1,10-bisaboladien-3-ols with m-chloroperbenzoic acid to form cis-10,11-epoxy-1-bisabolen-3-ols.

(139) A method of making (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, and (3S,6R,7R,10R)-10,11-epoxy-1-bisabolen-3-ol, comprising (or consisting essentially of or consisting of) reacting (R)-citronellal with formaldehyde in the presence of piperidine to form (R)-2-methylenecitronellal, reacting (R)-2-methylenecitronellal with methyl acetoacetonate to form (7R)-7,11-dimethyl-1,10-bisaboladien-3-one, reacting (7R)-7,11-dimethyl-1,10-bisaboladien-3-one with methyl lithium to form trans-(7R)-3,7,11-trimethyl-1,10-bisaboladien-3-ols and cis-(7R)-3,7,11-trimethyl-1,10-bisaboladien-3-ols; separating trans-(7R)-3,7,11-trimethyl-1,10-bisaboladien-3-ols and cis-(7R)-3,7,11-trimethyl-1,10-bisaboladien-3-ols; and reacting trans-(7R)-3,7,11-trimethyl-1,10-bisaboladien-3-ols with m-chloroperbenzoic acid to produce trans-epoxybisabolenols; and reacting cis-(7R)-3,7,11-trimethyl-1,10-bisaboladien-3-ols with m-chloroperbenzoic acid to produce cis-epoxybisabolenols.

A composition comprising (consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, and optionally a carrier material or carrier. The above composition, further comprising (consisting essentially of or consisting of) methyl (2E,4E,6Z)-decatrieonate.

The above composition, wherein said composition further comprises (consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol. The above composition, wherein said composition contains about 21% cis-epoxybisabolenols 7 and about 41% trans-epoxybisabolenols 8. The above composition, wherein said composition further contains 1,2,10,11-diepoxybisabolan-3-ols. The above composition according to claim 9, containing about 37% 1,2,10,11-diepoxybisabolan-3-ols. The above composition, further comprising (consisting essentially of or consisting of) methyl (2E,4E,6Z)-decatrieonate.

The above composition, wherein said composition contains a 3:1 ratio of cis-epoxybisabolenols:trans-epoxybisabolenols produced from (R)-citronellal.

The above composition, wherein said composition further comprises (consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol.

The above composition, wherein said composition further comprises (consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol.

The above composition, wherein said composition further comprises (consisting essentially of or consisting of) (3R,6R,7S,10S)-10,11-epoxy-1-bisabolen-3-ol, (3R,6R,7S,10R)-10,11-epoxy-1-bisabolen-3-ol, (3S,6S,7S,10S)-10,11-epoxy-1-bisabolen-3-ol, (3S,6S,7S,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol. The above composition, wherein said composition contains a 3:1 ratio of cis-epoxybisabolenols:trans-epoxybisabolenols produced from (S)-citronellal.

The above composition according to claim 1, further comprising (consisting essentially of or consisting of) methyl (2E,4E,6Z)-decatrieonate.

A method for attracting *Halyomorpha halys* to an object or area, comprising (consisting essentially of or consisting of) treating said object or area with a *Halyomorpha halys* attracting composition comprising (or consisting essentially of or consisting of) a *Halyomorpha halys* attracting effective amount of the above composition.

A kit for attracting *Halyomorpha halys*, comprising (consisting essentially of or consisting of):
 a. first attractant comprised (consisting essentially of or consisting of) of the above composition on a first carrier, and
 b. a second attractant comprised (consisting essentially of or consisting of) of methyl (2E,4E,6Z)-decatrieonate on a second carrier or on said first carrier.

The above kit, further comprising (consisting essentially of or consisting of) an insect trap for housing said first and second carriers.

The above kit, further comprising (consisting essentially of or consisting of) written instructions directed to deploying the attractants at separate seasonal times.

The above kit, further comprising (consisting essentially of or consisting of) one or more insecticides.

A composition comprising (consisting essentially of or consisting of) (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and optionally a carrier material or carrier.

The above composition, wherein said composition further comprises (consisting essentially of or consisting of) (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol.

The above composition, wherein said composition contains a 3:1 ratio of cis-epoxybisabolenols:trans-epoxybisabolenols produced from (S)-citronellal.

The above composition, further comprising (consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol.

The above composition, wherein said composition further comprises (consisting essentially of or consisting of) (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol. The above composition, wherein said composition contains a 3:1 ratio of cis-epoxybisabolenols:trans-epoxybisabolenols produced from (R)-citronellal.

The above composition, further comprising (consisting essentially of or consisting of) methyl (2E,4E,6Z)-decatrieonate.

A method for attracting *Halyomorpha halys* to an object or area, comprising (consisting essentially of or consisting of) treating said object or area with a *Halyomorpha halys* attracting composition comprising (consisting essentially of or consisting of) a *Halyomorpha halys* attracting effective amount of the above composition.

A kit for attracting *Halyomorpha halys*, comprising (consisting essentially of or consisting of):
 a. first attractant comprised (consisting essentially of or consisting of) of the above composition on a first carrier, and
 b. a second attractant comprised (consisting essentially of or consisting of) of methyl (2E,4E,6Z)-decatrieonate on a second carrier or on said first carrier.

The above kit, further comprising (consisting essentially of or consisting of) an insect trap for housing said first and second carriers.

The above kit, further comprising (consisting essentially of or consisting of) written instructions directed to deploying the attractants at separate seasonal times.

The above kit, further comprising (consisting essentially of or consisting of) one or more insecticides.

A composition comprising (consisting essentially of or consisting of) (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, (3R,6R,7S,10S)-10,11-epoxy-1-bisabolen-3-ol (19), 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-ol, (3R,6S,7S,10S)-10,11-epoxy-1-bisabolen-3-ol, (3S,6R,7S,10S)-10,11-epoxy-1-bisabolen-3-ol, and optionally a carrier material or carrier.

The above composition, wherein said composition contains a 3:1 ratio of cis-epoxybisabolenols:trans-epoxybisabolenols produced from (R)-citronellal and said composition contains a 3:1 ratio of cis-epoxybisabolenols:trans-epoxybisabolenols produced from (S)-citronellal.

The above composition, further comprising (consisting essentially of or consisting of) methyl (2E,4E,6Z)-decatrieonate.

A method for attracting *Halyomorpha halys* to an object or area, comprising (consisting essentially of or consisting of) treating said object or area with a *Halyomorpha halys* attracting composition comprising (consisting essentially of or consisting of) a *Halyomorpha halys* attracting effective amount of the above composition.

A kit for attracting *Halyomorpha halys*, comprising (consisting essentially of or consisting of):
a. first attractant comprised (consisting essentially of or consisting of) of the above composition on a first carrier, and
b. a second attractant comprised (consisting essentially of or consisting of) of methyl (2E,4E,6Z)-decatrieonate on a second carrier or on said first carrier.

The above kit, further comprising (consisting essentially of or consisting of) an insect trap for housing said first and second carriers.

The above kit, further comprising (consisting essentially of or consisting of) written instructions directed to deploying the attractants at separate seasonal times.

The above kit, further comprising (consisting essentially of or consisting of) one or more insecticides.

A composition comprising (consisting essentially of or consisting of) (3S,6S,7R,10S)-10,11-epoxy-1-bisabolen-3-ol (1) and optionally a carrier material or carrier A composition comprising (consisting essentially of or consisting of) (3R,6S,7R,10S)-10,11-epoxy-1-bisabolen-3-ol (3) and optionally a carrier material or carrier.

A composition comprising (consisting essentially of or consisting of) (3S,6S,7R,10S)-10,11-epoxy-1-bisabolen-3-ol (1), (3R,6S,7R,10S)-10,11-epoxy-1-bisabolen-3-ol (3), and optionally a carrier material or carrier.

A method to synthesize eight stereoisomers of 1,10-bisaboladien-3-ol, comprising (consisting essentially of or consisting of) reacting (ketone 10) (7R)-1,10-bisaboladien-3-one and/or (ketone 14) (7S)-1,10-bisaboladien-3-one with trimethylaluminum in the presence of chloro(1,5-cyclooctadiene) rhodium(I)dimer and (R) and/or (S)-2,2'-bis(diphenylphosphino)-1,1'-binaphthalene.

A method of preparing a composition containing (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol,
said method comprising (consisting essentially of or consisting of) reacting (cyclohexenone 10) (7R)-1,10-bisaboladien-3-one with methyl lithium (at about −15° C. to about −20° C. (e.g., −15° C. to −20° C.)) (in dry ether) to form cis- and trans-1,10-bisaboladien-3-ols mixture, and further epoxidizing said cis- and trans-1,10-bisaboladien-3-ols mixture (bisaboladienols mixture 11 and 12) with meta-chloroperbenzoic acid (at about 0° C. to about 5° C. (e.g., 0° C. to 5° C.)); said method does not utilize chromatographic separation.

The above method, wherein said composition contains about 21% cis-epoxybisabolenols 7 and about 41% trans-epoxybisabolenols 8.

The above method, wherein said composition further comprises (consisting essentially of or consisting of) 1,2,10,11-diepoxybisabolan-3-ols. The above method, wherein said composition further comprises (consisting essentially of or consisting of) 37% 1,2,10,11-diepoxybisabolan-3-ols.

The above composition, wherein said composition contains (3R,6S,7R,10S)-10,11-epoxy-1-bisabolen-3-ol.

The above composition, wherein said composition does not contain (3R,6S,7R,10S)-10,11-epoxy-1-bisabolen-3-ol.

The above composition, wherein said composition contains (3R,6S,7R,10R)-10,11-epoxy-1-bisabolen-3-ol.

The above composition, wherein said composition does not contain (3R,6S,7R,10R)-10,11-epoxy-1-bisabolen-3-ol.

The above composition, wherein said composition contains (3S,6R,7R,10S)-10,11-epoxy-1-bisabolen-3-ol.

The above composition, wherein said composition does not contain (3S,6R,7R,10S)-10,11-epoxy-1-bisabolen-3-ol.

The above composition, wherein said composition contains (3S,6R,7R,10R)-10,11-epoxy-1-bisabolen-3-ol.

The above composition, wherein said composition does not contain (3S,6R,7R,10R)-10,11-epoxy-1-bisabolen-3-ol.

The above composition, wherein said composition contains (3R,6R,7S,10S)-10,11-epoxy-1-bisabolen-3-ol.

The above composition, wherein said composition does not contain (3R,6R,7S,10S)-10,11-epoxy-1-bisabolen-3-ol.

The above composition, wherein said composition contains (3R,6R,7S,10R)-10,11-epoxy-1-bisabolen-3-ol.

The above composition, wherein said composition does not contain (3R,6R,7S,10R)-10,11-epoxy-1-bisabolen-3-ol.

The above composition, wherein said composition contains (3S,6S,7S,10S)-10,11-epoxy-1-bisabolen-3-ol.

The above composition, wherein said composition does not contain (3S,6S,7S,10S)-10,11-epoxy-1-bisabolen-3-ol.

The above composition, wherein said composition contains (3S,6S,7S,10R)-10,11-epoxy-1-bisabolen-3-ol.

The above composition, wherein said composition does not contain (3S,6S,7S,10R)-10,11-epoxy-1-bisabolen-3-ol.

The above composition, wherein said composition contains (3R,6S,7S,10R)-10,11-epoxy-1-bisabolen-3-ol.

The above composition, wherein said composition does not contain (3R,6S,7S,10R)-10,11-epoxy-1-bisabolen-3-ol.

The above composition, wherein said composition contains (3S,6R,7S,10R)-10,11-epoxy-1-bisabolen-3-ol.

The above composition, wherein said composition does not contain (3S,6R,7S,10R)-10,11-epoxy-1-bisabolen-3-ol.

The above composition, wherein said composition contains (3R,6S,7S,10S)-10,11-epoxy-1-bisabolen-3-ol.

The above composition, wherein said composition does not contain (3R,6S,7S,10S)-10,11-epoxy-1-bisabolen-3-ol.

The above composition, wherein said composition contains (3S,6R,7S,10S)-10,11-epoxy-1-bisabolen-3-ol.

The above composition, wherein said composition does not contain (3S,6R,7S,10S)-10,11-epoxy-1-bisabolen-3-ol.

A method of preparing a composition containing (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6R,7R,10R)-10,11-epoxy-1-bisabolen-3-ol, said method comprising reacting (7R)-1,10-bisaboladien-3-one with methyl lithium at about −15° C. to about −20° C. in dry ether to form cis- and trans-1,10-bisaboladien-3-ols mixture, and further epoxidizing said cis- and trans-1,10-bisaboladien-3-ols mixture with meta-chloroperbenzoic acid at about 0° C. to about 5° C.; said method does not utilize chromatographic separation.

A method for attracting *Halyomorpha halys* to an object or area, comprising (or consisting essentially of or consisting of) treating said object or area with a *Halyomorpha halys* attracting composition comprising (or consisting essentially of or consisting of) a *Halyomorpha halys* attracting effective amount of at least one compound described herein (or one of the compositions described herein). The compound(s) or composition(s) are used to treat an object or area in amounts effective to attract *Halyomorpha halys* to the object or area. As used herein "a *Halyomorpha halys* attracting effective amount" refers to an amount which attracts *Halyomorpha halys* compared to objects or areas which were not treated according to methods described herein. Any accurate method for measuring attraction may be used for such comparisons, as would be apparent to those skilled in the art. As used herein "in amounts effective" or "an effective amount" refers to the amount of the compounds(s) or composition(s) wherein the effect of the treatment acts to attract *Halyomorpha halys* to the object or area.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Chemical ionization GC/MS results of H. halys male-specific compounds in natural volatile extract on a 60m DB-WAXETR capillary column (50° C. for 2 min, then heated to 230° C. at 15° C./min and held for 15 min) using ammonia ($NH_3$) and deuteroammonia ($ND_3$) as the reagent gases (relative intensities in parentheses).

| Compounds | RT (min) | m/z |
|---|---|---|
| Compound 5 | 15.21 | 221 $[M + H]^+$ (100), 238 $[M + NH_4]^+$ (22) 222 $[M + D]^+$ (100), 242 $[[M + ND_4]^+$ (35) |
| Compound 4 | 15.75 | 221 $[M + H]^+$ (100), 238 $[M + NH_4]^+$ (19) 222 $[M + D]^+$ (100), 242 $[[M + ND_4]^+$ (44) |
| Compound A | 19.61 | 238 $[M]^+$ (16), 256 $[M + NH_4]^+$ (4) 241 $[M + D + H/D]^+$ (20), 261 $[M + ND_4 + H/D]^+$ (7) |
| Compound B | 20.61 | 238 $[M]^+$ (20), 256 $[M + NH_4]^+$ (2) 241 $[M + D + H/D]^+$ (33), 261 $[M + ND_4 + H/D]^+$ (1) |

TABLE 2

Chemicals tested in 2011-2012 field trials against BMSB

| Lure # | Description | Loading, mg[1] |
|---|---|---|
| 1 | (3R,6R,1S,10S)-10,11-Epoxy-1-bisabolen-3-ol (19) | 2 |
| 2 | cis-Epoxybisabolenol mixture 17 | 8 |
| 3 | Methyl (2E,4E,6Z)-decatrienoate, MDT[2,3] | 60[2], 119[3] |
| 4 | Control, unloaded septa | |
| 5 | Lure #1 plus trans-epoxybisabolenol mixture 18 | 2/2.7 |
| 6 | Mixture of Lure #2 and 18 | 8/2.7 |
| 7 | Mixture of 19, 44, and 18 | 2/2.7/0.1 |
| 8 | Mixture of 19 and 44 | 8/0.3 |
| 9 | Mixture of Lure #6 and mixture 43 | 10.7/0.8 |
| 10 | Mixture of 7 and 8 | 8/2.7 |
| 11 | Mixture of 2 and 40 | 2/2 |
| 12 | Mixture 7, 4 cis isomers with 7R configuration | 8 |
| 13 | Mixture 8, 4 trans isomers with 7R configuration | 8 |
| 14 | Lure #10 plus MDT[4] | 10.7/119 |
| 15 | Crude #10 | 18[5] |
| 16 | Mixture of #10 and #6 | 10.7/10.7 |
| 17 | (3R,6R,1R,10S)-10,11-Epoxy-1-bisabolen-3-ol (40) | 2 |
| 18 | (3R,6S,1R,10S)-10,11-Epoxy-1-bisabolen-3-ol (3) | 2 |
| 19 | Mixture of Lures #17 and #18 | 2/0.7 |
| 20 | Crude mixture of 7 and 8 (see Material and Methods) with a ratio 1:2 and containing 21% of 7 | 38[5] |
| 21 | Mixture of 7 and 8 utilizing only one chromatographic separation (see Material and Methods) | 8/2.7 |
| 22 | (3S,6S,7S,10S)-10,11-Epoxy-1-bisabolen-3-ol (1) | 2 |
| 23 | (3R,6R,7R,10R-10,11-Epoxy-1-bisabolen-3-ol (2) | 2 |
| 24-L | Mixture of Lures #22 and #23 | 2/2 |

TABLE 2-continued

Chemicals tested in 2011-2012 field trials against BMSB

| Lure # | Description | Loading, mg[1] |
|---|---|---|
| 24-H | Mixture of Lures #22 and #23 | 4/4 |
| 25 | Mixture of Lures #22, #23, and #18 | 2/2/1.3 |

[1]Rubber septa
[2]In 2011, AgBio commercial MDT formulated in a plastic membrane;
[3]In 2012, Sterling International Inc. Rescue MDT lure formulated in a plastic membrane;
[4]#10 and Rescue MDT were hung as separate lures in the same trap
[5]Contained 8 mg of 7

TABLE 3

Mean number BMSB adults and nymphs (±SE) captured per trap per sample in trials conducted in 2011 at APRS.

| Trial | Treatment | Adults[1] | Nymphs[2] |
|---|---|---|---|
| One 19 April-10 May | #1 | 0.03 ± 0.03 | 0.00 ± 0.00 |
| | #2 | 0.07 ± 0.07 | 0.00 ± 0.00 |
| | #3 (MDT) | 0.00 ± 0.00 | 0.00 ± 0.00 |
| | #4 (Control) | 0.00 ± 0.00 | 0.00 ± 0.00 |
| Two 10-24 May | #2 | 0.30 ± 0.13 | 0.00 ± 0.00 |
| | #4 (Control) | 0.05 ± 0.05 | 0.00 ± 0.00 |
| | #5 | 0.00 ± 0.00 | 0.00 ± 0.00 |
| | #6 | 0.10 ± 0.07 | 0.00 ± 0.00 |
| Three 24 May-24 June | #2 | 0.62 ± 0.14ab | 0.04 ± 0.03 |
| | #4 (Control) | 0.24 ± 0.07b | 0.20 ± 0.14 |
| | #6 | 0.92 ± 0.17a | 0.22 ± 0.16 |
| | #7 | 0.22 ± 0.16b | 0.07 ± 0.07 |
| Four 24 June-5 July | #2 | 0.67 ± 0.29 | 0.86 ± 0.41 |
| | #4 (Control) | 0.40 ± 0.16 | 0.53 ± 0.35 |
| | #6 | 0.67 ± 0.27 | 0.80 ± 0.37 |
| | #7(4x) | 0.53 ± 0.35 | 0.27 ± 0.21 |
| Five 8 July-2 August | #2 | 0.75 ± 0.16ab | 8.75 ± 4.30 |
| | #4 (Control) | 0.18 ± 0.06c | 4.23 ± 1.04 |
| | #6 | 1.03 ± 0.24a | 6.70 ± 2.52 |
| | #8 | 0.43 ± 0.11bc | 5.48 ± 1.46 |
| Six 29 July-10 August | #6 (2 mg) | 0.13 ± 0.06b | 10.63 ± 3.98b |
| | #6 (8 mg) | 0.21 ± 0.08ab | 11.45 ± 3.57ab |
| | #6 (50 mg) | 0.63 ± 0.22a | 18.79 ± 5.34a |
| | #4 (Control) | 0.13 ± 0.07b | 7.92 ± 2.77b |
| Seven 8-19 August | #3 (MDT) | 1.97 ± 0.37a | 34.55 ± 5.85a |
| | #4 (Control) | 0.76 ± 0.15b | 17.06 ± 3.29b |
| | #6 (50 mg) | 2.97 ± 0.44a | 34.07 ± 5.50a |
| Eight 11 August-6 Sept. | #1 | 3.08 ± 0.55b | 14.63 ± 6.06 |
| | #2 | 12.93 ± 2.45a | 26.73 ± 9.53 |
| | #4 (Control) | 2.50 ± 0.57b | 9.85 ± 2.29 |
| | #6 | 14.08 ± 2.30a | 23.43 ± 7.28 |
| | #9 | 15.08 ± 2.52a | 24.55 ± 6.07 |
| Nine 6-30 September | #2 | 22.71 ± 3.37b | 0.77 ± 0.24 |
| | #4 (Control) | 7.09 ± 1.85c | 0.88 ± 0.35 |
| | #6 | 28.74 ± 5.38b | 7.80 ± 3.73 |
| | #9 | 27.97 ± 5.65b | 1.11 ± 0.40 |
| | #10 | 1038.34 ± 14.43a | 1.02 ± 0.33 |
| Ten 19 Sept.-4 Oct. | #3 (MDT) | 22.76 ± 4.41a | 1.24 ± 0.34a |
| | #4 (Control) | 4.28 ± 1.06b | 0.20 ± 0.08b |
| | #6 | 10.04 ± 2.32b | 0.16 ± 0.10b |
| | #10 | 31.56 ± 7.94a | 0.72 ± 0.15ab |
| | #11 | 7.76 ± 1.84b | 0.20 ± 0.13b |
| Eleven 12-16 September | #4 (Control) | 11.67 ± 3.72 | 0.67 ± 0.22 |
| | #6 (2 mg) | 15.83 ± 2.92 | 0.67 ± 0.14 |
| | #6 (8 mg) | 18.17 ± 4.78 | 0.50 ± 0.23 |
| | #6 (48 mg) | 26.50 ± 5.38 | 0.67 ± 0.28 |
| Twelve 30 Sept.-20 Oct. | #4 (Control) | 1.17 ± 0.45b | 0.00 ± 0.00 |
| | #10 | 8.57 ± 2.92a | 0.13 ± 0.06 |
| | #12 | 10.00 ± 4.35a | 0.17 ± 0.14 |
| | #13 | 1.23 ± 0.42b | 0.03 ± 0.03 |
| | #14 | 23.63 ± 5.46a | 0.17 ± 0.10 |
| Thirteen 7-20 October | #4 (Control) | 1.84 ± 0.59 | 0.08 ± 0.06 |
| | #10 (2 mg) | 2.84 ± 0.54 | 0.28 ± 0.11 |
| | #10 (8 mg) | 2.84 ± 0.72 | 0.20 ± 0.08 |
| | #10 (48 mg) | 5.24 ± 1.55 | 0.20 ± 0.13 |
| Fourteen 7-20 October | #4 (Control) | 1.53 ± 0.45 | 0.20 ± 0.15 |
| | #10 | 2.33 ± 0.84 | 0.53 ± 0.34 |

TABLE 3-continued

Mean number BMSB adults and nymphs (±SE) captured
per trap per sample in trials conducted in 2011 at APRS.

| Trial | Treatment | Adults[1] | Nymphs[2] |
|---|---|---|---|
|  | #15 | 1.60 ± 0.41 | 0.13 ± 0.09 |
|  | #16 | 2.47 ± 0.52 | 0.93 ± 0.28 |

[1]Adult values in the same column and from a single trial and followed by a different letter are significantly different according to Tukey's HSD ($P \leq 0.05$)
[2]Nymphal values in the same column and from a single trial and followed by a different letter are significantly different according to Tukey's HSD ($P \leq 0.05$)

TABLE 4

Mean number BMSB adults and nymphs (±SE) captured per
treatment in all trials conducted in 2011 in Beltsville.

| Trial | Treatment | Adults[1] | Nymphs[2] |
|---|---|---|---|
| One | #1 | 0.00 ± 0.20b | 0.00 ± 0.00 |
| 19 April-10 May | #2 | 0.10 ± 0.05a | 0.00 ± 0.00 |
|  | #3 | 0.02 ± 0.02ab | 0.00 ± 0.00 |
|  | #4 (Control) | 0.00 ± 0.00b | 0.00 ± 0.00 |
| Two | #2 | 0.08 ± 0.04 | 0.00 ± 0.00 |
| 10-24 May | #4 (Control) | 0.03 ± 0.03 | 0.00 ± 0.00 |
|  | #5 | 0.03 ± 0.03 | 0.00 ± 0.00 |
|  | #6 | 0.08 ± 0.08 | 0.00 ± 0.00 |
| Three | #2 | 0.45 ± 0.11a | 0.11 ± 0.08 |
| 24 May-24 June | #4 (Control) | 0.09 ± 0.04b | 0.10 ± 0.06 |
|  | #6 | 0.38 ± 0.08a | 0.15 ± 0.07 |
|  | #7 | 0.20 ± 0.07ab | 0.13 ± 0.07 |
| Four | #2 | 0.43 ± 0.12ab | 2.33 ± 0.93ab |
| 24 June-5 July | #4 (Control) | 0.10 ± 0.05b | 0.28 ± 0.14b |
|  | #6 | 0.85 ± 0.19a | 4.10 ± 2.11a |
|  | #7(4x) | 0.40 ± 0.11ab | 0.63 ± 0.34b |
| Five | #2 | 0.74 ± 0.14ab | 6.43 ± 1.45 |
| 8 July-2 August | #4 (Control) | 0.37 ± 0.11b | 3.23 ± 0.72 |
|  | #6 | 1.03 ± 0.17a | 7.52 ± 2.18 |
|  | #8 | 0.53 ± 0.09b | 5.97 ± 1.82 |
| Eight | #1 | 0.55 ± 0.13ab | 3.49 ± 0.67 |
| 11 August-6 Sept. | #2 | 1.28 ± 0.19b | 6.07 ± 1.83 |
|  | #4 (Control) | 0.48 ± 0.12b | 14.01 ± 1.62 |
|  | #6 | 2.05 ± 0.40a | 13.18 ± 1.52 |
|  | #9 | 1.78 ± 0.24a | 8.19 ± 2.50 |
| Nine | #2 | 1.95 ± 0.38b | 0.34 ± 0.10 |
| 6-30 September | #4 (Control) | 0.58 ± 0.13b | 0.22 ± 0.08 |
|  | #6 | 1.34 ± 0.25b | 0.29 ± 0.11 |
|  | #9 | 1.65 ± 0.27b | 0.42 ± 0.19 |
|  | #10 | 10.89 ± 2.00a | 0.56 ± 0.18 |
| Twelve | #4 (Control) | 0.06 ± 0.04b | 0.00 ± 0.00 |
| 30 Sept.-20 Oct. | #10 | 0.60 ± 0.19b | 0.01 ± 0.01 |
|  | #12 | 0.99 ± 0.29b | 0.01 ± 0.01 |
|  | #13 | 0.11 ± 0.06b | 0.01 ± 0.01 |
|  | #14 | 2.75 ± 0.79a | 0.00 ± 0.00 |

[1]Adult values in the same column and from a single trial and followed by a different letter are significantly different according to Tukey's HSD ($P \leq 0.05$)
[2]Nymphal values in the same column and from a single trial and followed by a different letter are significantly different according to Tukey's HSD ($P \leq 0.05$)

TABLE 5

Mean number BMSB adults (±SE) captured
per treatment in all trials at AFRS in 2012.

| Trial | Treatment | Adults | Nymphs |
|---|---|---|---|
| One | #10 | 1.93 ± 0.71a | 0.00 ± 0.00 |
| 20 March-17 April | #4 (Control) | 0.20 ± 0.10b | 0.00 ± 0.00 |
| Two | #10 | 1.60 ± 0.39a | 19.3 ± 7.84a |
| 31 July-14 August | #12 | 2.75 ± 0.66a | 4.80 ± 0.97ab |
|  | #13 | 0.70 ± 0.21bc | 3.95 ± 1.12b |
|  | #17 | 0.40 ± 0.40bc | 7.15 ± 2.65ab |
|  | #18 | 0.90 ± 0.38bc | 6.50 ± 2.08ab |
|  | #19 | 1.30 ± 0.40ab | 9.35 ± 6.46b |
|  | #4 (Control) | 0.05 ± 0.05c | 2.65 ± 1.29b |
| Three | #10 | 10.55 ± 1.35a | 17.13 ± 3.23a |
| 14 August- | #12 | 9.53 ± 1.48ab | 17.83 ± 3.62a |

TABLE 5-continued

Mean number BMSB adults (±SE) captured
per treatment in all trials at AFRS in 2012.

| Trial | Treatment | Adults | Nymphs |
|---|---|---|---|
| 13 September | #13 | 2.93 ± 0.39cd | 8.65 ± 2.03ab |
|  | #22 | 2.73 ± 0.50d | 7.30 ± 2.02bc |
|  | #23 | 0.75 ± 0.29e | 2.50 ± 0.53c |
|  | #24L | 5.95 ± 0.91bc | 11.1 ± 2.72ab |
|  | #4 (Control) | 0.70 ± 0.19e | 3.90 ± 1.03c |
| Four | #12 | 3.52 ± 1.12ab | 1.28 ± 0.77 |
| 22 September- | #18 | 2.48 ± 0.70abc | 0.60 ± 0.37 |
| 10 October | #22 | 1.36 ± 0.59bc | 0.80 ± 0.57 |
|  | #24L | 1.48 ± 0.36bc | 0.36 ± 0.18 |
|  | #24H | 6.92 ± 1.90a | 1.60 ± 0.90 |
|  | #25 | 2.28 ± 0.63abc | 0.28 ± 0.14 |
|  | #4 (Control) | 0.36 ± 0.11c | 0.04 ± 0.04 |

Means in the same column and from a single trial and followed by a different letter are significantly different according to Tukey's HSD ($P \leq 0.05$)

TABLE 6

Mean number BMSB adults (±SE) captured per
treatment in all trials at Beltsville in 2012.

| Trial | Treatment | Adults | Nymphs |
|---|---|---|---|
| Two | #10 | 0.60 ± 0.20ab | 18.90 ± 8.42 |
| 1-14 August | #12 | 0.80 ± 0.32a | 27.75 ± 10.13 |
|  | #13 | 0.20 ± 0.12ab | 16.00 ± 8.85 |
|  | #17 | 0.20 ± 0.12ab | 20.30 ± 8.61 |
|  | #18 | 0.35 ± 0.13ab | 23.45 ± 9.95 |
|  | #19 | 0.20 ± 0.12ab | 14.45 ± 6.20 |
|  | #4 (Control) | 0.10 ± 0.07b | 3.80 ± 1.72 |
| Three | #10 | 6.55 ± 1.41a | 17.60 ± 5.67ab |
| 14 August- | #12 | 5.38 ± 1.27a | 28.10 ± 6.41a |
| 11 September | #13 | 2.83 ± 0.55b | 14.90 ± 3.84abc |
|  | #22 | 2.65 ± 0.44a | 21.90 ± 6.49ab |
|  | #23 | 0.90 ± 0.26b | 8.38 ± 2.90bc |
|  | #24L | 3.50 ± 0.68a | 21.15 ± 6.05ab |
|  | #4 (Control) | 0.25 ± 0.09b | 4.60 ± 1.70c |
| Four | #12 | 5.05 ± 0.98a | 0.05 ± 0.05 |
| 17 September- | #18 | 4.15 ± 1.17a | 0.05 ± 0.05 |
| 2 October | #22 | 5.05 ± 1.01a | 0.15 ± 0.11 |
|  | #24L | 7.85 ± 1.90a | 0.05 ± 0.05 |
|  | #24H | 8.55 ± 2.11a | 0.15 ± 0.08 |
|  | #25 | 10.70 ± 2.94a | 0.30 ± 0.15 |
|  | #4 (Control) | 0.70 ± 0.19b | 0.00 ± 0.00 |

Means in the same column and from a single trial and followed by a different letter are significantly different according to Tukey's HSD ($P \leq 0.05$)

TABLE 7

Mean number BMSB adults (±SE) captured per trap per
sample date in all trials at Kearneysville from 14 May-7
June and from 8 May-5 June in Beltsville in 2012.

| Trial | Treatment | Adults |
|---|---|---|
| Kearneysville, WV | #10 | 1.57 ± 0.46a |
|  | #20 | 1.51 ± 0.32a |
|  | #21 | 1.57 ± 0.339a |
|  | #4 (Control) | 0.14 ± 0.55b |
| Beltsville, MD | #10 | 0.87 ± 0.27a |
|  | #20 | 1.50 ± 0.32a |
|  | #21 | 1.23 ± 0.36a |
|  | #4 (Control) | 0.03 ± 0.03b |

Adult values in the same column and from a single trial and followed by a different letter are significantly different according to Tukey's HSD ($P \leq 0.05$)

TABLE 8

Mean number of BMSB adults and nymphs (±SE) captured per trap per sample date in dose response trials conducted in Shepherdstown, WV, and Keedysville, MD, from 17 June to 12 July 2012, and in Beltsville, MD from 5 June to 3 July 2012.

| Location | Dose | Adults | Nymphs |
|---|---|---|---|
| Shepherdstown, WV | 100 mg | 8.94 ± 2.32a | 43.63 ± 10.53a |
| | 10 mg | 4.97 ± 1.39ab | 16.34 ± 3.75b |
| | 1 mg | 0.94 ± 0.29b | 4.94 ± 1.29b |
| | 0.1 mg | 0.78 ± 0.25b | 5.72 ± 2.17b |
| | (0 mg) Control | 0.44 ± 0.13b | 3.41 ± 0.99b |
| Keedysville, MD | 100 mg | 9.03 ± 1.57a | 43.94 ± 9.94a |
| | 10 mg | 3.56 ± 0.75b | 16.09 ± 5.14b |
| | 1 mg | 1.84 ± 0.40bc | 9.84 ± 2.73b |
| | 0.1 mg | 0.38 ± 0.11c | 0.96 ± 0.32b |
| | (0 mg) Control | 0.10 ± 0.05c | 7.56 ± 6.53b |
| Beltsville, MD | 100 mg | 2.28 ± 0.60a | 5.56 ± 2.13a |
| | 10 mg | 0.47 ± 0.17b | 2.75 ± 1.19a |
| | 1 mg | 0.13 ± 0.07b | 1.16 ± 0.46ab |
| | 0.1 mg | 0.00 ± 0.00b | 0.13 ± 0.10ab |
| | (0 mg) Control | 0.00 ± 0.00b | 1.84 ± 0.98b |

Adult and nymphal values in the same column and from a single trial and followed by a different letter are significantly different according to Tukey's HSD ($P \leq 0.05$)

TABLE 9

Season-long total captures of BMSB

| | BMSB Adults | | BMSB Nymphs | |
|---|---|---|---|---|
| lure | Beltsville* | Arden* | Beltsville | Arden |
| MDT + #10 | 3783 a | 4231 a | 3688 a | 1404 a |
| MDT | 1203 b | 999 b | 1823 b | 386 b |
| #10 | 822 b | 304 b | 718 bc | 185 b |
| Control | 94 b | 38 b | 207 c | 121 b |
| TOTAL | 5902 | 5572 | 6436 | 2096 |
| MDT + #10 | 64.1% | 75.9% | 57.3% | 67.0% |
| MDT | 20.4% | 17.9% | 28.3% | 18.4% |
| #10 | 13.9% | 5.5% | 11.2% | 8.8% |
| Control | 1.6% | 0.7% | 3.2% | 5.8% |

Based on 4 replicates for 6 April through 23 Oct. 2012, Beltsville, MD, and 3 replicates for 20 May through 23 Oct. 2012, Arden, WV. Within each column, totals followed by a common letter do not differ by Tukey's HSD test, $p < 0.05$.
Asterisk indicates significant interaction (positive synergism) between lure types for the season-long totals.

TABLE 10

Summary of captures by approximate fortnightly collection periods, 6 April through 23 October 2012, Beltsville, MD. Within each row, totals followed by a common letter do not differ by Tukey's HSD test, $p < 0.05$, for that sample period. Asterisk at end of row indicates significant interaction (positive synergism) between lure types for that sample period.

ADULT BMSB Beltsville, MD

| 2012 DATES | capture for 4 traps/trtmt | Control adults captured (% of total) | | #10 adults captured (% of total) | | MDT adults captured (% of total) | | MDT + 10 adults captured (% of total) | | |
|---|---|---|---|---|---|---|---|---|---|---|
| 6-20 April | 14-day total | 2 | 3.40% | 9 | 15.30% | 6 | 10.20% | 42 | 71.20% | |
| 20 April-4 May | 14-day total | 2 | 6.30% | 3 | 9.40% b | 7 | 21.90% ab | 20 | 62.50% a | |
| 4-22 May | 18-day total | 1 | 1.00% b | 16 | 16.50% b | 2 | 2.10% b | 78 | 80.40% a | * |
| 22 May-5 June | 14-day total | 0 | 0.00% b | 27 | 26.50% b | 3 | 2.90% b | 72 | 70.60% a | * |
| 5-19 June | 14-day total | 1 | 0.70% b | 18 | 12.50% b | 6 | 4.20% b | 119 | 82.60% a | * |
| 19-29 June | 14-day total | 0 | 0.00% b | 2 | 9.10% b | 0 | 0.00% b | 20 | 90.90% a | * |
| 29 June-13 July | 14-day total | 0 | 0.00% b | 13 | 22.40% ab | 5 | 8.60% b | 40 | 60.00% a | |
| 13-27 July | 14-day total | 0 | 0.00% b | 24 | 30.00% | 0 | 0.00% | 56 | 70.00% | |
| 27 July-10 Aug | 14-day total | 7 | 3.10% b | 18 | 7.90% b | 14 | 6.10% b | 190 | 83.00% a | * |
| 10-24 Aug | 14-day total | 1 | 0.70% b | 38 | 24.80% ab | 7 | 4.60% b | 107 | 69.50% a | |
| 24Aug-7Sept | 14-day total | 18 | 1.00% b | 218 | 12.30% b | 393 | 22.20% b | 1143 | 64.50% a | |
| 7-21 Sept | 14-day total | 40 | 2.60% b | 291 | 18.90% ab | 314 | 20.30% ab | 898 | 58.20% a | |
| 21Sep-5 Oct | 14-day total | 21 | 1.30% b | 142 | 9.00% b | 440 | 27.90% b | 974 | 51.89% a | |
| 5-23Oct | 18-day total | 1 | 2.90% b | 3 | 8.80% b | 6 | 17.50% ab | 24 | 70.60% a | |
| 6APR-23OCT | Total | 94 | 1.60% b | 822 | 13.90% b | 1203 | 10.40% b | 3783 | 64.10% a | * |

NYMPHAL BMSB Beltsville, MD

| 2012 DATES | capture for 4 traps/trtmt | Control nymphs captured (% of total) | | #10 nymphs captured (% of total) | | MDT nymphs captured (% of total) | | MDT + 10 nymphs caputed (% of total) | | |
|---|---|---|---|---|---|---|---|---|---|---|
| 6-20 April | 14-day total | 0 | | 0 | | 0 | | 0 | | |
| 20 April-4 May | 14-day total | 0 | | 0 | | 0 | | 0 | | |
| 4-22 May | 18-day total | 0 | | 0 | | 0 | | 0 | | |
| 22May-5June | 14-day total | 0 | 0% | 4 | 22.20% | 7 | 38.90% | 7 | 38.90% | |
| 5-19 June | 14-day total | 5 | 2.00% b | 32 | 12.70% ab | 63 | 25.10% ab | 151 | 60.20% a | |
| 19-29 June | 14-day total | 3 | 0.60% b | 38 | 8.10% b | 6 | 1.30% b | 425 | 90.00% a | * |
| 29 June-13 July | 14-day total | 0 | 0% b | 27 | 10.00% ab | 40 | 14.50% ab | 202 | 79.10% a | |
| 13-27 July | 14-day total | 2 | 3.10% | 13 | 20.30% | 13 | 20.30% | 36 | 56.10% | |
| 27 July-10 Aug | 14-day total | 41 | 3.10% b | 38 | 2.90% b | 406 | 30.80% ab | 833 | 63.20% a | |
| 10-24 Aug | 14-day total | 113 | 7.90% b | 140 | 16.70% ab | 212 | 14.80% b | 870 | 60.60% a | |
| 24Aug-7Sept | 14-day total | 36 | 1.50% | 311 | 12.80% | 1018 | 41.80% | 1068 | 48.90% | |

TABLE 10-continued

Summary of captures by approximate fortnightly collection periods, 6 April through 23 October 2012, Beltsville, MD. Within each row, totals followed by a common letter do not differ by Tukey's HSD test, p < 0.05, for that sample period. Asterisk at end of row indicates significant interaction (positive synergism) between lure types for that sample period.

| | | | | | | | | | | |
|---|---|---|---|---|---|---|---|---|---|---|
| 7-21 Sept | 14-day total | 5 | 4.20% b | 10 | 8.30% b | 36 | 30.00% ab | 69 | 57.50% a | |
| 21Sep-5 Oct | 14-day total | 2 | 4.80% | 5 | 11.90% | 17 | 40.50% | 18 | 42.90% | |
| 5-23Oct | 18-day total | 0 | 0% | 0 | 0% | 5 | 35.70% | 9 | 64.30% | |
| 6APR-23OCT | TOTAL | 207 | 3.20% c | 718 | 21.20% bc | 1823 | 28.30% b | 3688 | 57.30% a | * |

TABLE 11

Summary of captures by approximate fortnightly collection periods, 16 May through 23 October 2012, Arden, WV. Within each row, totals followed by a common letter do not differ by Tukey's HSD test, p < 0.05, for that sample period. Asterisk at end of row indicates significant interaction (positive synergism) between lure types for tht sample period.

ADULT BMSB
Arden, WV

| 2012 DATES | capture for 4 traps/trtmt | Control adults captured | (% of total) | #10 adults captured | (% of total) | MDT adults captured | (% of total) | MDT + 10 adults captured | (% of total) | |
|---|---|---|---|---|---|---|---|---|---|---|
| May 16-23 | 7-day total | 0 | 0% | 0 | 0% | 0 | 0% | 8 | 100% | |
| May23-Jun4 | 14-day total | 0 | 0% b | 3 | 25% ab | 0 | 0% b | 9 | 75% a | |
| June4-19 | 15-day total | 0 | 0% | 1 | 50% | 0 | 0% | 1 | 50% | |
| June19-July2 | 13-day total | 0 | 0% | 0 | 0% | 0 | 0% | 1 | 100% | |
| July2-17 | 15-day total | 0 | 0% | 1 | 20% | 0 | 0% | 4 | 80% | |
| July17-Aug2 | 16-day total | 0 | 0% | 2 | 11.8% | 0 | 0% | 15 | 88.20% | |
| Aug2-13 | 11-day total | 7 | 10.4% | 5 | 7.5% | 7 | 10.40% | 48 | 71.50% | |
| Aug13-27 | 14-day total | 1 | 0.8% | 30 | 23.3% | 4 | 3.10% | 94 | 72.90% | |
| Aug27-Sep10 | 14-day total | 4 | 2.1% | 63 | 33.2% | 3 | 1.60% | 120 | 63.20% | |
| Sep10-24 | 14-day total | 1 | 0% b | 68 | 2.6% b | 333 | 12.70% b | 2210 | 84.60% a | * |
| Sep24-Oct9 | 17-day total | 8 | 0.4% c | 101 | 4.8% c | 532 | 25.20% b | 1473 | 69.70% a | * |
| Oct9-23 | 14-day total | 17 | 4.1% | 30 | 7.2% | 120 | 28.90% | 248 | 99.80% | |
| 15 May-23 Oct | TOTAL | 38 | 0.7% b | 304 | 5.5% b | 999 | 17.9% b | 4231 | 75.9% a | * |

NYMPHAL BMSB
Arden, WV

| 2012 DATES | capture for 4 traps/trtmt | Control nymphs captured | (% of total) | #10 nymphs captured | (% of total) | MDT nymphs captured | (% of total) | MDT + 10 nymphs captured | (% of total) | |
|---|---|---|---|---|---|---|---|---|---|---|
| May 16-23 | 7-day total | 0 | | 0 | | 0 | | 0 | | |
| May23-Jun4 | 14-day total | 0 | | 0 | | 0 | | 0 | | |
| June4-19 | 15-day total | 0 | | 0 | | 0 | | 0 | | |
| June19-July2 | 13-day total | 1 | 14.3% | 0 | 0% | 0 | 0% | 6 | 89.7% | |
| July2-17 | 15-day total | 2 | 1.3% b | 11 | 6.9% b | 8 | 5.0% b | 139 | 86.9% a | * |
| July17-Aug2 | 16-day total | 10 | 27.8% | 13 | 36.1% | 8 | 22.2% | 5 | 13.9% | |
| Aug2-13 | 11-day total | 15 | 3.8% | 15 | 3.8% | 38 | 9.5% | 331 | 83.0% | |
| Aug13-27 | 14-day total | 53 | 10.4% | 73 | 24.3% | 51 | 10.0% | 334 | 65.4% | |
| Aug27-Sep10 | 14-day total | 36 | 22.6% | 31 | 19.5% | 68 | 42.8% | 24 | 15.1% | |
| Sep10-24 | 14-day total | 2 | 0.4% b | 12 | 2.1% b | 135 | 23.9% b | 416 | 73.6% a | * |
| Sep24-Oct9 | 17-day total | 1 | 0.4% | 27 | 21.9% | 58 | 25.7% | 140 | 61.9% | |
| Oct9-23 | 14-day total | 1 | 3.0% | 3 | 9.1% | 20 | 60.5% | 9 | 27.3% | |
| 15May-23 Oct | TOTAL | 121 | 5.8% b | 185 | 8.8% b | 386 | 18.4% b | 1404 | 67.0% a | |

TABLE 12

Isolated yields, specific rotations, low-resolution and high-resolution mass spectra data for individual triols and epoxybisabolenols including *H. halys* suspected pheromone components 1, 2 and 3.

| Compd. No. | Absolute configuration | Yield, % | $[\alpha]_D^{20}$ (c, CH$_2$Cl$_2$) | HRMS | LRMS, m/z (%)[b] |
|---|---|---|---|---|---|
| 33 | 3S,6S,7R,10S | 91 | −19.4 (4.0) | 279.1927[a] | 238(3), 223(5), 220(4), 205(8), 180(12), 179(12), 162(19), 147(23), 138(37), 134(74), 132(63), 121(86), 94(94), 93(86), 79(56), 59(100), 43(97), 41(33) |
| 34 | 3S,6S,7R,10R | 75 | +26.5 (1.5) | 279.1932[a] | 238(1), 223(3), 220(2), 205(6), 180(12), 162(21), 147(20), 138(40), 134(59), 132(46), 121(73), 94(100), 93(62), 79(47), 59(93), 43(84), 41(27) |
| 35 | 3R,6R,7R,10S | 83 | −21.3(1.9) | 279.1930[a] | 238(1), 223(4), 220(4), 205(5), 180(15), 162(18), 147(21), 138(30), 134(66), 132(57), 121(87), 94(95), 93(81), 79(50), 59(100), 43(91), 41(30) |
| 36 | 3R,6R,7R,10R | 92 | +17.3 (2.1) | 279.1930[a] | 238(1), 223(3), 220(2), 205(5), 180(15), 162(18), 147(21), 138(27), 134(60), 132(50), 121(85), 94(96), 93(71), 79(49), 59(100), 43(88), 41(29) |
| 37 | 3R,6S,7R,10R | 70[c] | +66.6 (2.6) | 279.1940[a] | 238(1), 223(5), 220(3), 205(7), 180(12), 179(12), 162(11), 159 (12), 147(18), 138(25), 134(65), 132(74), 121(83), 94(45), 93(68), 79(31), 59(100), 43(80), 41(25) |
| 38 | 3R,6R,7S,10R | 71 | +17.0(0.5) | 279.1933[a] | 238(2), 223(4), 220(1), 205(5), 180(10), 179(7), 162(17), 147(16), 138(37), 134(49), 132(38), 121(67), 94(100), 93(51), 79(47), 59(92), 43(85), 41(26) |
| 39 | 3S,6S,7R,10R | 66 | +8.2(1.2) | 261.1838[d] | 220(2), 205(6), 187(4), 165(28), 147(19), 138(28), 134(48), 132(36), 123(28), 121(37), 119(41), 109(37), 105(29), 94(48), 93(61), 91(43), 79(40), 71(51), 59(27), 55(29), 43(100), 41(41) |
| 1 | 3S,6S,7R,10S | 60 | −1.6(1.2) | 261.1828[d] | 220(2), 205(6), 187(3), 165(29), 147(18), 138(33), 134(46), 132(32), 123(30), 121(35), 119(36), 109(39), 105(25), 94(50), 93(53), 91(35), 79(39), 71(49), 59(27), 55(28), 43(100), 41(40) |
| 2 | 3R,6R,7R,10R | 73 | +0.1(5.2) | 261.1836[d] | 220(2), 205(7), 187(5), 165(28), 147(22), 138(32), 134(52), 132(42), 123(35), 121(42), 119(44), 109(43), 105(31), 94(54), 93(62), 91(42), 79(42), 71(52), 59(29), 55(29), 43(100), 41(41) |
| 40 | 3R,6R,7R,10S | 64 | −9.6(1.1) | 261.1825[d] | 220(3), 205(6), 187(4), 165(21), 147(19), 138(25), 134(47), 132(39), 123(28), 121(37), 119(40), 109(38), 105(29), 94(49), 93(61), 91(42), 79(39), 71(49), 59(27), 55(28), 43(100), 41(42) |
| 3 | 3R,6S,7R,10S | 51 | +35.8(0.9) | 261.1823[d] | 223(1), 220(1), 205(6), 187(5), 165(38), 147(17), 138(19), 134(53), 132(63), 123(39), 121(38), 119(47), 109(46), 105(30), 95(39), 93(52), 91(35), 79(29), 71(47), 59(26), 55(29), 43(100), 41(39) |
| 19 | 3R,6R,7S,10S | 69 | −8.1 (1.0) | 261.1824[d] | 220(2), 205(5), 187(4), 165(26), 147(18), 138(27), 134(47), 132(35), 123(28), 121(36), 119(41), 109(38), 105(30), 94(50), 93(65), 91(47), 79(43), 71(53), 59(29), 55(31), 43(100), 41(45) |

[a]HRESIMS; calcd for C$_{15}$H$_{28}$O$_3$Na 279.1936;
[b]Mass spectra data from GC-MS analysis;
[c]after 32 h run;
[d]HRESIMS; calcd for C$_{15}$H$_{26}$O$_2$Na 261.1831

TABLE 13

¹H NMR data of *H. halys* suspected pheromone components 1, 2 and 3 and other individual triols and epoxybisabolenols Table 13: ¹H NMR Chemical shifts (ppm), multiplicities, J coupling constants, Hz Position

| Compd. | 1 | 2 | 4 | 5 | 6 | 7 | 8 | 9 | 10 | 12 | 13 | 14 | 15 |
|---|---|---|---|---|---|---|---|---|---|---|---|---|---|
| 33 | 5.63 dt, 10.1, 1.5 | 5.68, dt, 10.1, 2.0 | 1.83, m 1.56, m | 1.57, m 1.49, m | 2.08, m | 1.58, m | 1.71, m 1.21, m | 1.57, m 1.22, m | 3.32, dd, 9.8, 1.8 | 1.15, s | 1.21, s | 0.88, d, 6.9 | 1.26, s |
| 34 | 5.67, m | 5.67, m | 1.83, m 1.54, m | 1.58, m 1.49, m | 2.06, m | 1.57, m | 1.45, m 1.45, m | 1.46, m 1.36, m | 3.34, d, 10.0 | 1.15, s | 1.20, s | 0.89, d, 6.8 | 1.26, s |
| 35 | 5.69, s | 5.69, s | 1.83, m 1.56, m | 1.60, m 1.55, m | 2.07, m | 1.54, m | 1.70, m 1.19, m | 1.57, m 1.22, m | 3.31, dd, 9.9, 1.8 | 1.15, s | 1.21, s | 0.93, d, 6.8 | 1.27, s |
| 36 | 5.69, s | 5.69, s | 1.85, m 1.55, m | 1.62, m 1.53, m | 2.04, m | 1.55, m | 1.45, m 1.42, m | 1.45, m 1.36, m | 3.33, d, 9.8 | 1.15, s | 1.20, s | 0.92, d, 6.7 | 1.26, s |
| 37 | 5.56, ddd, 10.2, 2.2, 1.1 | 5.62, ddd, 10.2, 2.5, 1.5 | 1.87, d, 12.2, 1.64, m | 1.71, m 1.43, m | 2.14, m | 1.54, m | 1.44, m 1.44, m | 1.45, m 1.36, m | 3.33, d, 9.9 | 1.15, s | 1.20, s | 0.86, d, 6.7 | 1.27, s |
| 38 | 5.63, dt, 10.1, 1.5 | 5.68, ddd, 10.1, 2.4, 1.7 | 1.83, m 1.56, m | 1.57, m 1.49, m | 2.08, m | 1.58, m | 1.71, m 1.21, m | 1.57, m 1.22, m | 3.32, dd, 9.9, 1.8 | 1.15, s | 1.20, s | 0.88, d, 6.8 | 1.26, s |
| 39 | 5.64, dt, 10.1, 1.2 | 5.69, dt, 10.1, 1.9 | 1.83, m 1.55, m | 1.56, m 1.49, m | 2.08, m | 1.60, m | 1.50, m 1.38, m | 1.59, m 1.50, m | 2.69, t, 6.0 | 1.27, s | 1.30, s | 0.89, d, 6.8 | 1.26, s |
| 1 | 5.64, dt, 10.0, 1.3 | 5.69, dt, 10.0, 1.9 | 1.83, m 1.54, m | 1.57, m 1.49, m | 2.07, m | 1.60, m | 1.59, m 1.28, m | 1.58, m 1.50, m | 2.69, t, 6.0 | 1.26, s | 1.30, s | 0.89, d, 6.7 | 1.26, s |
| 2 | 5.67, m | 5.68, m | 1.83, m 1.56, m | 1.62, m 1.54, m | 2.05, m | 1.56, m | 1.49, m 1.37, m | 1.60, m 1.48, m | 2.68, t, 6.0 | 1.26, s | 1.30, s | 0.93, d, 6.8 | 1.27, s |
| 40 | 5.68, m | 5.69, m | 1.83, m 1.56, m | 1.61, m 1.53, m | 2.05, m | 1.57, m | 1.58, m 1.27, m | 1.58, m 1.49, m | 2.68, m | 1.26, s | 1.30, s | 0.93, d, 6.7 | 1.27, s |
| 3 | 5.55, ddd, 10.2, 2.2, 1.1 | 5.62, ddd, 10.2, 2.5, 1.5 | 1.87, m 1.64, m | 1.70, m 1.42, m | 2.15, m | 1.56, m | 1.57, m 1.26, m | 1.57, m 1.48, m | 2.68, dd, 6.3, 5.3 | 1.26, s | 1.30, s | 0.87, d, 6.6 | 1.26, s |
| 19 | 5.64, dt, 10.2, 1.5 | 5.69, ddd, 10.1, 2.5, 1.7 | 1.83, m 1.54, m | 1.56, m 1.49, m | 2.08, m | 1.60, m | 1.50, m 1.38, m | 1.59, m 1.50, m | 2.69, t, 5.9 | 1.26, s | 1.30, s | 0.89, d, 6.8 | 1.26, s |

TABLE 14

¹³C NMR data of *H. halys* suspected pheromone components 1, 2 and 3 and other individual triols and epoxybisabolenols ¹³C NMR Chemical shifts (ppm), multiplicities Position

| Compd. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 33 | 133.9, CH | 133.6, CH | 67.0, C | 37.3, $CH_2$ | 20.0, $CH_2$ | 40.3, CH | 36.9, CH | 31.3, $CH_2$ | 29.8, $CH_2$ | 79.0, CH | 72.9, C | 23.0, $CH_3$ | 26.3, $CH_3$ | 15.7, $CH_3$ | 29.6, $CH_3$ |
| 34 | 133.6, CH | 133.6, CH | 67.0, C | 37.3, $CH_2$ | 20.4, $CH_2$ | 40.8, CH | 36.7, CH | 31.0, $CH_2$ | 29.5, $CH_2$ | 78.6, CH | 72.8, C | 23.0, $CH_3$ | 26.3, $CH_3$ | 15.5, $CH_3$ | 29.6, $CH_3$ |
| 35 | 132.6, CH | 134.0, CH | 67.1, C | 37.4, $CH_2$ | 22.0, $CH_2$ | 41.0, CH | 37.0, CH | 30.8, $CH_2$ | 29.9, $CH_2$ | 79.2, CH | 72.9, C | 23.0, $CH_3$ | 26.3, $CH_3$ | 16.5, $CH_3$ | 29.6, $CH_3$ |
| 36 | 132.7, CH | 134.0, CH | 67.1, C | 37.4, $CH_2$ | 21.9, $CH_2$ | 41.3, CH | 36.7, CH | 30.5, $CH_2$ | 29.6, $CH_2$ | 78.6, CH | 72.8, C | 23.0, $CH_3$ | 26.3, $CH_3$ | 16.2, $CH_3$ | 29.6, $CH_3$ |
| 37 | 131.5, CH | 134.9, CH | 69.4, C | 38.2, $CH_2$ | 22.5, $CH_2$ | 40.4, CH | 36.7, CH | 31.0, $CH_2$ | 29.5, $CH_2$ | 78.6, CH | 72.8, C | 23.0, $CH_3$ | 26.3, $CH_3$ | 15.4, $CH_3$ | 28.2, $CH_3$ |
| 38 | 133.8, CH | 133.6, CH | 67.0, C | 37.3, $CH_2$ | 20.0, $CH_2$ | 40.3, CH | 36.9, CH | 31.3, $CH_2$ | 29.8, $CH_2$ | 79.0, CH | 72.9, C | 23.0, $CH_3$ | 26.3, $CH_3$ | 15.7, $CH_3$ | 29.6, $CH_3$ |
| 39 | 133.6, CH | 133.7, CH | 67.0, C | 37.3, $CH_2$ | 20.1, $CH_2$ | 40.3, CH | 36.6, CH | 30.7, $CH_2$ | 26.9, $CH_2$ | 64.2, CH | 57.9, C | 18.5, $CH_3$ | 24.6, $CH_3$ | 15.5, $CH_3$ | 29.6, $CH_3$ |
| 1 | 133.5, CH | 133.8, CH | 67.0, C | 37.3, $CH_2$ | 20.2, $CH_2$ | 40.6, CH | 36.7, CH | 30.8, $CH_2$ | 27.1, $CH_2$ | 64.3, CH | 57.8, C | 18.4, $CH_3$ | 24.6, $CH_3$ | 15.5, $CH_3$ | 29.6, $CH_3$ |
| 2 | 132.4, CH | 134.1, CH | 67.1, C | 37.4, $CH_2$ | 22.0, $CH_2$ | 41.0, CH | 36.6, CH | 30.2, $CH_2$ | 27.0, $CH_2$ | 64.2, CH | 57.9, C | 23.0, $CH_3$ | 26.3, $CH_3$ | 16.2, $CH_3$ | 29.6, $CH_3$ |
| 40 | 132.5, CH | 134.1, CH | 67.1, C | 37.4, $CH_2$ | 21.9, $CH_2$ | 41.2, CH | 36.7, CH | 30.2, $CH_2$ | 27.2, $CH_2$ | 64.3, CH | 57.7, C | 18.4, $CH_3$ | 24.6, $CH_3$ | 16.2, $CH_3$ | 29.6, $CH_3$ |
| 3 | 131.4, CH | 135.0, CH | 69.4, C | 38.2, $CH_2$ | 22.4, $CH_2$ | 40.2, CH | 36.6, CH | 30.8, $CH_2$ | 27.0, $CH_2$ | 64.3, CH | 57.7, C | 18.4, $CH_3$ | 24.6, $CH_3$ | 15.4, $CH_3$ | 28.2, $CH_3$ |
| 19 | 133.6, CH | 133.7, CH | 67.0, C | 37.3, $CH_2$ | 20.1, $CH_2$ | 40.3, CH | 36.6, CH | 30.7, $CH_2$ | 26.9, $CH_2$ | 64.2, CH | 57.9, C | 18.5, $CH_3$ | 24.6, $CH_3$ | 15.5, $CH_3$ | 29.6, $CH_3$ |

We claim:

1. A composition comprising (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and optionally a carrier material or carrier.

2. A method for attracting *Halyomorpha halys* to an object or area, comprising treating said object or area with a *Halyomorpha halys* attracting composition comprising a *Halyomorpha halys* attracting effective amount of the composition according to claim 1.

3. The composition according to claim 1, said composition consisting essentially of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S, 10R)-10,11-epoxy-1-bisabolen-3-ol, and optionally methyl (2E,4E,6Z)-decatrieonate, and optionally a carrier material or carrier.

4. The composition according to claim 1, said composition consisting of (3R,6R,7S,10S)-10,11-epoxy-1-bisabolen-3-ol, 3R,6R,7S,10R)-10,11-epoxy-1-bisabolen-3-ol, 3S,6S,7S, 10S)-10,11-epoxy-1-bisabolen-3-ol, 3S,6S,7S,10R)-10,11-epoxy-1-bisabolen-3-ol, and optionally methyl (2E,4E,6Z)-decatrieonate, and optionally a carrier material or carrier.

5. A method for attracting *Halyomorpha halys* to an object or area, comprising treating said object or area with a *Halyomorpha halys* attracting composition consisting essentially of a *Halyomorpha halys* attracting effective amount of a composition consisting essentially of (3R,6R,7S,10S)-10,11-epoxy-1-bisabolen-3-ol, 3R,6R,7S,10R)-10,11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, and optionally methyl (2E,4E,6Z)-decatrieonate, and optionally a carrier material or carrier.

6. A method for attracting *Halyomorpha halys* to an object or area, comprising treating said object or area with a *Halyomorpha halys* attracting composition consisting of a *Halyomorpha halys* attracting effective amount of a composition consisting of (3R,6R,7S,10S)-10,11-epoxy-1-bisabolen-3-ol, 3R,6R,7S,10R)-10,11-epoxy-1-bisabolen-3-ol, 3S,6S,7S, 10S)-10,11-epoxy-1-bisabolen-3-ol, 3S,6S,7S,10R)-10,11-epoxy-1-bisabolen-3-ol, and optionally methyl (2E,4E,6Z)-decatrieonate, and optionally a carrier material or carrier.

7. The composition according to claim 1, wherein said composition does not contain (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-ol, (3S,6S,7R,10R)-10,11-epoxy-1-bisabolen-3-ol, (3R,6R,7R,10S)-10,11-epoxy-1-bisabolen-3-ol, (3R,6R,7R,10R)-10,11-epoxy-1-bisabolen-3-ol, (3S,6S,7R,10S)-10,11-epoxy-1-bisabolen-3-ol, (3S,6S,7R,10R)-10,11-epoxy-1-bisabolen-3-ol, (3R,6S,7R,10R)-10,11-epoxy-1-bisabolen-3-ol, (3S,6R,7S,10R)-10,11-epoxy-1-bisabolen-3-ol, (3R,6S,7S, 10S)-10,11-epoxy-1-bisabolen-3-ol, and (3S,6R,7S,10S)-10,11-epoxy-1-bisabolen-3-ol.

8. A method of preparing a composition containing 3R,6R, 7S,10S)-10,11-epoxy-1-bisabolen-3-ol, 3R,6R,7S,10R)-10, 11-epoxy-1-bisabolen-3-ol, 3S,6S,7S,10S)-10,11-epoxy-1-bisabolen-3-ol, 3S,6S,7S,10R)-10,11-epoxy-1-bisabolen-3-ol, said method comprising reacting cyclohexenone 14 with methyl lithium at about −15° C. to about −20° C. in dry ether to form cis- and trans-1,10-bisaboladien-3-ols mixture, separating said mixture into individual cis-1,10-bisaboladien-3-ols mixture (15) and trans-1,10-bisaboladien-3-ols mixture (16) by chromatography on silica gel, and further epoxidizing said cis-1,10-bisaboladien-3-ols mixture (15) with meta-chloroperbenzoic acid at about 0° C. to about 5° C. in dichloromethane in the presence of sodium acetate.

9. A method for attracting *Halyomorpha halys* to an object or area, comprising treating said object or area with a *Halyomorpha halys* attracting composition comprising a *Halyomorpha halys* attracting effective amount of a composition comprising (3R,6R,7S,10S)-10,11-epoxy-1-bisabolen-3-ol, 3R,6R,7S,10R)-10,11-epoxy-1-bisabolen-3-ol, 3S,6S,7S, 10S)-10,11-epoxy-1-bisabolen-3-ol, 3S,6S,7S,10R)-10,11-epoxy-1-bisabolen-3-ol, and optionally methyl (2E,4E,6Z)-decatrieonate, and optionally a carrier material or carrier; wherein said composition does not contain (3R,6S,7R,10S)-10,11-epoxy-1-bisabolen-3-ol, (3R,6S,7R,10R)-10,11-epoxy-1-bisabolen-3-ol, (3S,6R,7R,10S)-10,11-epoxy-1-bisabolen-3-01, (3S,6R,7R,10R)-10,11-epoxy-1-bisabolen-3-ol, (3R,6R,7R,10S)-10,11-epoxy-1-bisabolen-3-ol, (3R,6R, 7R,10R)-10,11-epoxy-1-bisabolen-3-ol, (3S,6S,7R,10S)-10, 11-epoxy-1-bisabolen-3-ol, (3S,6S,7R,10R)-10,11-epoxy-1-bisabolen-3-ol, (3R,6S,7S,10R)-10,11-epoxy-1-bisabolen-3-ol, (3S,6R,7S,10R)-10,11-epoxy-1-bisabolen-3-01, (3R,6S,7S,10S)-10,11-epoxy-1-bisabolen-3-ol, and (3S,6R,7S,10S)-10,11-epoxy-1-bisabolen-3-ol.

10. The composition according to claim 1, further comprising methyl (2E,4E,6Z)- decatrieonate.

11. The method according to claim 2, wherein said composition further comprises methyl (2E,4E,6Z)-decatrieonate.

12. The method according to claim 9, wherein said composition further comprises methyl (2E,4E,6Z)-decatrieonate.

* * * * *